(12) United States Patent
Ekema et al.

(10) Patent No.: US 8,460,894 B2
(45) Date of Patent: Jun. 11, 2013

(54) CALCIUM-SENSING RECEPTOR 2 (CAR2) AND METHODS FOR USING

(75) Inventors: George Mbella Ekema, Lakewood, OH (US); Pieter W. Faber, Westlake, OH (US); Benjamin Philip Faga, University Heights, OH (US); Gregory B. Foust, Euclid, OH (US); John Joseph Harrington, Mentor, OH (US); Paul David Jackson, Shaker Heights, OH (US); Robert W. Mays, Cleveland Heights, OH (US)

(73) Assignee: ABT Holding Company, Cleveland, OH (US)

( * ) Notice: Subject to any disclaimer, the term of this patent is extended or adjusted under 35 U.S.C. 154(b) by 445 days.

(21) Appl. No.: 12/482,702

(22) Filed: Jun. 11, 2009

(65) Prior Publication Data

US 2009/0285801 A1 Nov. 19, 2009

Related U.S. Application Data

(63) Continuation of application No. 11/784,976, filed on Apr. 10, 2007, now abandoned, which is a continuation of application No. 10/283,842, filed on Oct. 29, 2002, now abandoned.

(60) Provisional application No. 60/421,941, filed on Oct. 28, 2002.

(51) Int. Cl.
*C12P 21/06* (2006.01)
*C12N 15/06* (2006.01)
*C07K 1/00* (2006.01)
*C07H 21/02* (2006.01)

(52) U.S. Cl.
USPC .................. 435/69.1; 435/320.1; 530/350

(58) Field of Classification Search
None
See application file for complete search history.

(56) References Cited

U.S. PATENT DOCUMENTS

2009/0178153 A1* 7/2009 Gaitanaris et al. .............. 800/18

* cited by examiner

*Primary Examiner* — Olga N Chernyshev
(74) *Attorney, Agent, or Firm* — Tarolli, Sundheim, Covell & Tummino LLP

(57) ABSTRACT

The current disclosure provide a novel human calcium sensing receptor named CaR2 and the nucleotide sequence that encodes the receptor. The disclosure further provides antibodies specific for CaR2. Also disclosed are methods of identifying modulators of the receptor and methods of using the identified modulators to treat calcium receptor mediated conditions.

11 Claims, 7 Drawing Sheets

FIGURE 1A

167B12 cDNA. (2778 bp ORF)

```
                  aatactgagtgtttctggcctttgacactgtcctataccttataaggtgtttacaggtgaaataggtg      -79
aaataggaatcttgctggcactccgtgcacttaatgattcctaagaactcacatgaactgagcaaatgagatagaaac      -1
ATG CCA TTC TTA ATT ATA CTA ATT ACC TGC TTT GTG ATT ATT CTT GCT ACT TCA CAG CCT       60
TGC CAG ACC CCT GAT GAC TTT GTG GCT GCC ACT TCT CCG GGA CAT ATC ATA ATT GGA GGT      120
TTG TTT GCT ATT CAT GAA AAA ATG TTG TCC TCA GAA GAC TCT CCC AGA CGA CCA CAA ATC      180
CAG GAG TGT GTT GGC TTT GAA ATA TCA GTT TTT CTT CAA ACT CTT GCC ATG ATA CAC AGC      240
                        Δ
ATT GAG ATG ATC AAC AAT TCA ACA CTC TTA tCT CGA GTC AAA CTG GGG TAT GAA ATC TAT      300
GAC ACT TGT ACA GAA GTC ACA GTG GCA ATG GCg GCC ACT CTG AGG TTT CTT TCT AAA TTC      360
AAC TGC TCC AGA GAA ACT GTG GAG TTT AAG TGT GAC TAT TCC AGC TAC ATG CCA AGA GTT      420
AAG GCT GTC ATA GGT TCT GGG TAC TCA GAA ATA ACT ATG GCT GTC TCC AGG ATG TTG AAT      480
TTA CAG CTC ATG CCA CAC GTG GGT TAT GAA TCA ACT GCA GAA ATC CTG AGT GAC AAA ATT      540
                            Δ
CGC TTT CCT TCA TTT TTA CGG ACT GTG CCC AGT GAC TTC CAT CAA ATT AAA GCA ATG GCT      600
CAC CTG ATT CAG AAA TCT GGT TGG AAC TGG ATT GGC ATC ATA ACC ACA GAT GAT GAC TAT      660
GGA CGA TTG CTT AAC ACT TTT ATA ATT CAG GCT GAA GCA AAT AAC GTG TGC ATA GCC      720
TTC AAA GAG GTT CTT CCA GCC TTT CTT TCA GAT AAT ACC ATT GAA GTC AGA ATC AAT CGG      780
ACA CTG AAG AAA ATC ATT TTA GAA GCC CAG GTT AAT GTC ATT GTG GTA TTT CTG AGG CAA      840
TTC CAT GTT TTT GAT CTC TTC AAT AAA GCC ATT GAA ATG AAT ATA AAT AAG ATG TGG ATT      900
GCT AGT GAT AAT TGG TCA ACT GCC ACC AAG ATT ACC ACC ATT CCT AAT GTT AAA AAG ATT      960
GGC AAA GTT GTA GGG TTT GCC TTT AGA AGA GGG AAT ATA TCC TCT TTC ATT CCT TTC TT     1020
CAA AAT CTG CAC TTG CTT CCC AGT GAC AGT CAC AAA CTC TTA CAT GAA TAT GCC ATG CAT     1080
TTA TCT GCC TGC GCA TAT GTC AAG GAC ACT GAT TTG AGT CAA TGC ATA TTC AAT CAT TCT     1140
CAA AGG ACT TTG GCC TAC AAG GCT AAC AAG GCT ATA GAA AGG AAC TTC GTC ATG AGA AAT     1200
GAC TTC CTC TGG GAC TAT GCT GAG CCA GGA CTC ATT CAT AGT ATT CAG CTT GCA GTG TTT     1260
GCC CTT GGT TAT GCC ATT CGG GAT CTG TGT CAA GCT CGT GAC TGT CAG AAC CCC AAC GCC     1320
TTT CAA CCA TGG GAG TTA CTT GGT GTG CTA AAA AAT GTG ACA TTC ACT GAT GGA TGG AAT     1380
                    Δ
TCA TTT CAT TTT GAT GCT CAt GGG GAT TTA AAT ACT GGA TAT GAT GTT GTG CTC TGG AAG     1440
GAG ATC AAT GGA CAC ATG ACT GTC ACT AAG ATG GCA GAA TAT GAC CTA CAG AAT GAT GTC     1500
TTC ATC ATC CCA GAT CAG GAA ACA AAA AAT GAG TTC AGG AAT CTT AAG CAA ATT CAA TCT     1560
                                                                Δ
AAA TGC TCC AAG GAA TGC AGT CCT GGG CAA ATG AAG AAA ACT ACA AGA AGT CAA CAC ATC     1620
TGT TGC TAT GAA TGT CAG AAC TGT CCT GAA AAT CAT TAC ACT AAT CAG ACA GAT ATG CCT     1680
                                                             Δ
CAT TGC CTT TTA TGC AAC AAC AAA ACT CAC TGG GCC CCT GTT AGG AGC ACT ATG TGC TTT     1740
GAA AAG GAA GTG GAA TAT CTC AAC TGG AAT GAC TCC TTG CCA TCC TAC TC CTG ATT CTC     1800
TCC CTA CTG GGA ATC ATA TTT GTT CTG GTT GTT GGC ATA ATA TTT ACA AGA AAC CTG AAC     1860
ACt CCc GTT GTG AAA TCA TCC GGG GGA TTA AGA GTC TGC TAT GTG ATC CTT CTC TGT CAT     1920
TTC CTC AAT TTT GCC AGC ACG AGC TTT TCA TTG GAA CCA CAA GAC TTC ACA TGT AAA     1980
ACC AGG CAG ACA ATG TTT GGA GTG AGC TTT ACT CTT TGC ATC TCC TGC ATT TGG ACG AAG     2040
TCT CTG AAA ATT TTG CTA GCt TTC AGC TTT GAT CCC AAA TTA CAG AAA TTT CTG AAG TGC     2100
CTC TAT AGA CCG ATC CTT ATT ATC TTC ACT TGC ACG GGC ATC CAG GTT GTC ATT TGC ACA     2160
CTC TGG CTA ATC TTT GCA GCA CCT ACT GTA GAG GTG AAT GTC TCC TTC CCC AGA GTC ATC     2220
ATC CTG GAG TGT GAG GAG GGA TCC ATA CTT GCA TTT GGC ACC ATG CTG GGC TAC ATT GCC     2280
ATC CTG GCC TTC ATT GCT TCA TAT ATT GCT TTC AAA GGC AAA TAT GAG AAT TAC AAT GAA     2340
GCC AAA TTC ATT ACA TTT GGC ATG CTC ATT TAC TTC ATA GCT TGG ATC ACA TTC ATC CCT     2400
ATC TAT GCT ACC ACA TTT GGC AAA TAT GTA CCg GCT GTG GAG ATT ATT GTC ATA TTA ATA     2460
```

```
TCT AAC TAT GGA ATC CTG TAT TGC ACA TTC ATC CCC AAA TGC TAT GTT ATT ATT TGT AAG  2520
CAA GAG ATT AAC ACA AAG TCT GCC TTT CTC AAG ATG ATC TAC AGT TAT TCT TCC CAT AGT  2580
GTG AGC AGC ATT GCC CTG AGT CCT GCT TCA CTG GAC TCC ATG AGC GGC AAT GTC ACA ATG  2640
ACC AAT CCC AGC TCT AGT GGC AAG TCa GCA ACC TGG CAG AAA AGC AAA GAT CTT CAG GCA  2700
CAA GCA TTT GCA CAC ATA TGC AGG GAA AAT GCC ACA AGT GTA TCT AAA ACT TTG CCT CGA  2760
AAA AGA ATG TCA AGT ATA TGAataagccttaggagagatgcuacattccagaataaaatgtttccagggtctt  2833
tgcatctaagatataaatttactttcccagcaaatatgtcatatatatttccttgccaccatctttaccaagtttagt  2906
tgaacagtcactctgttcaatcacctatttaacaaatagaattgagccttcagcctgaagct                  2968
```

FIGURE 1B

Amino Acid Sequence of 167B12 Polypeptide

MAFLIILITCFVIILATSQPCQTPDDFVAATSPGHIIIGGLFAIHEKMLSSEDSPRRPQI 60

QECVGFEISVFLQTLAMIHSIEMINNSTLLSGVKLGYEIYDTCTEVTVAMAATLRFLSKF 120
            Δ

NCSRETVEFKCDYSSYMPRVKAVIGSGYSEITMAVSRMLNLQLMPQVGYESTAEILSDKI 180
                                                          Δ

RFPSFLRTVPSDFHQIKAMAHLIQKSGWNWIGIITTDDDYGRLALNTFIIQAEANNVCIA 240

FKEVLPAFLSDNTIEVRINRTLKKIILEAQVNVIVVFLRQFHVFDLFNKAIEMNINKMWI 300

ASDNWSTATKITTIPNVKKIGKVVGPAFRRGNISSFHSFLQNLHLLPSDSHKLLHEYAMH 360

LSACAYVKDTDLSQCIFNHSQRTLAYKANKAIERNFVMRNDFLWDYAEPGLIHSIQLAVF 420

ALGYAIRDLCQARDCQNPNAFQPWELLGVLKNVTFTDGWNSFHFDAHGDLNTGYDVVLWK 480
                                            Δ

EINGHMTVTKMAEYDLQNDVFIIPDQETKNEFRNLKQIQSKCSKECSPGQMKKTTRSQHI 540
                                                          Δ

CCYECQNCPENHYTNQTDMPHCLLCNNKTHWAPVRSTMCFEKEVEYLNWNDSLAILLLIL 600
     Δ

SLLGIIFVLVVGIIFTRNLNTPVVKSSGGLRVCYVILLCHFLNFASTSFFIGEPQDFTCK 660

TRQTMFGVSFTLCISCILTKSLKILLAFSFDPKLQKFLKCLYRPILIIFTCTGIQVVICT 720

LWLIFAAPTVEVNVSLPRVIILECEEGSILAFGTMLGYIAILAFICFIFAFKGKYENYNE 780

AKFITFGMLIYFIAWTTFIPIYATTFGKYVPAVEIIVILISNYGILYCTFIPKCYVIICK 840

QEINTKSAFLKMIYSYSSHSVSSIALSPASLDSMSGNVTMTNPSSSGKSATWQKSKDLQA 900

QAFAHICRENATSVSKTLPRKRMSSI 926

FIGURE 4: Dose-dependent enhancement by osteocalcin of $Ca^{++}$-mediated activation of CaR2
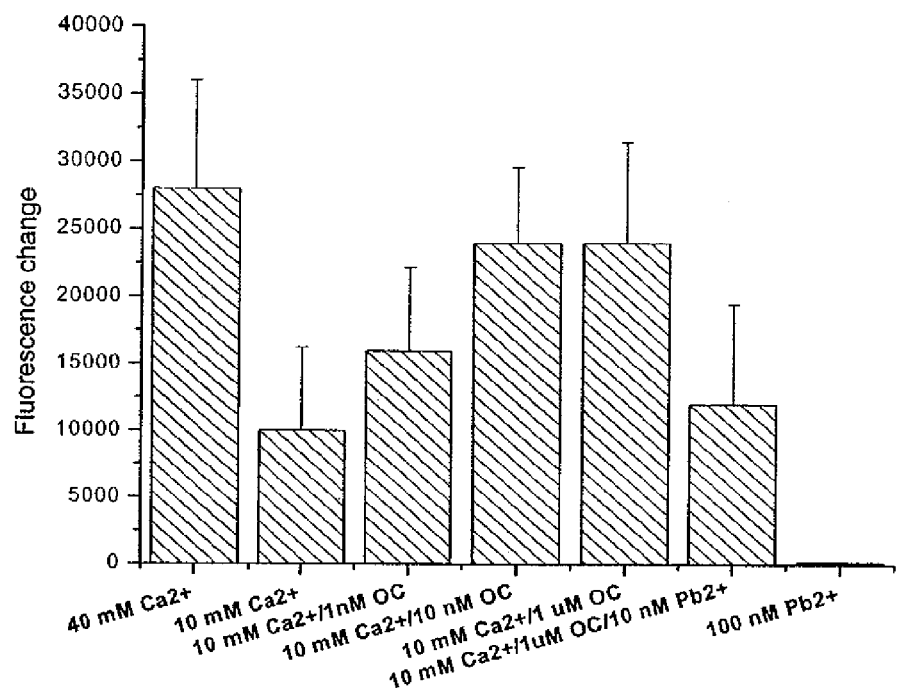

SEQUENCE LISTING

<160> NUMBER OF SEQ ID NOS: 4

<210> SEQ ID NO 1
<211> LENGTH: 3120
<212> TYPE: DNA
<213> ORGANISM: Homo sapiens
<220> FEATURE:
<221> NAME/KEY: CDS
<222> LOCATION: (147)...(2927)

<400> SEQUENCE: 1

```
aatactgagt gtttctggcc tttgacactg tcctatacct tataaggtgt ttacaggtga      60
aataggtgaa ataggaatct tgctggcact ccgtgcactt aatgattcct aagaactcac     120
atgaactgag caaatgagat agaaac atg gca ttc tta att ata cta att acc      173
                              Met Ala Phe Leu Ile Ile Leu Ile Thr
                               1               5 tgc ttt gtg att att ctt gct act tca cag cct tgc cag acc cct gat      221
Cys Phe Val Ile Ile Leu Ala Thr Ser Gln Pro Cys Gln Thr Pro Asp
 10                  15                  20                  25 gac ttt gtg gct gcc act tct ccg gga cat atc ata att gga ggt ttg      269
Asp Phe Val Ala Ala Thr Ser Pro Gly His Ile Ile Ile Gly Gly Leu
                 30                  35                  40 ttt gct att cat gaa aaa atg ttg tcc tca gaa gac tct ccc aga cga      317
Phe Ala Ile His Glu Lys Met Leu Ser Ser Glu Asp Ser Pro Arg Arg
             45                  50                  55 cca caa atc cag gag tgt gtt ggc ttt gaa ata tca gtt ttt ctt caa      365
Pro Gln Ile Gln Glu Cys Val Gly Phe Glu Ile Ser Val Phe Leu Gln
         60                  65                  70 act ctt gcc atg ata cac agc att gag atg atc aac aat tca aca ctc      413
Thr Leu Ala Met Ile His Ser Ile Glu Met Ile Asn Asn Ser Thr Leu
     75                  80                  85 tta tct gga gtc aaa ctg ggg tat gaa atc tat gac act tgt aca gaa      461
Leu Ser Gly Val Lys Leu Gly Tyr Glu Ile Tyr Asp Thr Cys Thr Glu
 90                  95                 100                 105 gtc aca gtg gca atg gcg gcc act ctg agg ttt ctt tct aaa ttc aac      509
Val Thr Val Ala Met Ala Ala Thr Leu Arg Phe Leu Ser Lys Phe Asn
                110                 115                 120 tgc tcc aga gaa act gtg gag ttt aag tgt gac tat tcc agc tac atg      557
Cys Ser Arg Glu Thr Val Glu Phe Lys Cys Asp Tyr Ser Ser Tyr Met
            125                 130                 135 cca aga gtt aag gct gtc ata ggt tct ggg tac tca gaa ata act atg      605
Pro Arg Val Lys Ala Val Ile Gly Ser Gly Tyr Ser Glu Ile Thr Met
        140                 145                 150 gct gtc tcc agg atg ttg aat tta cag ctc atg cca cag gtg ggt tat      653
Ala Val Ser Arg Met Leu Asn Leu Gln Leu Met Pro Gln Val Gly Tyr
    155                 160                 165 gaa tca act gca gaa atc ctg agt gac aaa att cgc ttt cct tca ttt      701
Glu Ser Thr Ala Glu Ile Leu Ser Asp Lys Ile Arg Phe Pro Ser Phe
170                 175                 180                 185 tta cgg act gtg ccc agt gac ttc cat caa att aaa gca atg gct cac      749
Leu Arg Thr Val Pro Ser Asp Phe His Gln Ile Lys Ala Met Ala His
                190                 195                 200 ctg att cag aaa tct ggt tgg aac tgg att ggc atc ata acc aca gat      797
Leu Ile Gln Lys Ser Gly Trp Asn Trp Ile Gly Ile Ile Thr Thr Asp
            205                 210                 215 gat gac tat gga cga ttg gct ctt aac act ttt ata att cag gct gaa      845
Asp Asp Tyr Gly Arg Leu Ala Leu Asn Thr Phe Ile Ile Gln Ala Glu
        220                 225                 230 gca aat aac gtg tgc ata gcc ttc aaa gag gtt ctt cca gcc ttt ctt      893
```

```
Ala Asn Asn Val Cys Ile Ala Phe Lys Glu Val Leu Pro Ala Phe Leu
        235                 240                 245 tca gat aat acc att gaa gtc aga atc aat cgg aca ctg aag aaa atc      941
Ser Asp Asn Thr Ile Glu Val Arg Ile Asn Arg Thr Leu Lys Lys Ile
250                 255                 260                 265 att tta gaa gcc cag gtt aat gtc att gtg gta ttt ctg agg caa ttc      989
Ile Leu Glu Ala Gln Val Asn Val Ile Val Val Phe Leu Arg Gln Phe
                270                 275                 280 cat gtt ttt gat ctc ttc aat aaa gcc att gaa atg aat ata aat aag     1037
His Val Phe Asp Leu Phe Asn Lys Ala Ile Glu Met Asn Ile Asn Lys
            285                 290                 295 atg tgg att gct agt gat aat tgg tca act gcc acc aag att acc acc     1085
Met Trp Ile Ala Ser Asp Asn Trp Ser Thr Ala Thr Lys Ile Thr Thr
        300                 305                 310 att cct aat gtt aaa aag att ggc aaa gtt gta ggg ttt gcc ttt aga     1133
Ile Pro Asn Val Lys Lys Ile Gly Lys Val Val Gly Phe Ala Phe Arg
315                 320                 325 aga ggg aat ata tcc tct ttc cat tcc ttt ctt caa aat ctg cac ttg     1181
Arg Gly Asn Ile Ser Ser Phe His Ser Phe Leu Gln Asn Leu His Leu
330                 335                 340                 345 ctt ccc agt gac agt cac aaa ctc tta cat gaa tat gcc atg cat tta     1229
Leu Pro Ser Asp Ser His Lys Leu Leu His Glu Tyr Ala Met His Leu
                350                 355                 360 tct gcc tgc gca tat gtc aag gac act gat ttg agt caa tgc ata ttc     1277
Ser Ala Cys Ala Tyr Val Lys Asp Thr Asp Leu Ser Gln Cys Ile Phe
            365                 370                 375 aat cat tct caa agg act ttg gcc tac aag gct aac aag gct ata gaa     1325
Asn His Ser Gln Arg Thr Leu Ala Tyr Lys Ala Asn Lys Ala Ile Glu
        380                 385                 390 agg aac ttc gtc atg aga aat gac ttc ctc tgg gac tat gct gag cca     1373
Arg Asn Phe Val Met Arg Asn Asp Phe Leu Trp Asp Tyr Ala Glu Pro
395                 400                 405 gga ctc att cat agt att cag ctt gca gtg ttt gcc ctt ggt tat gcc     1421
Gly Leu Ile His Ser Ile Gln Leu Ala Val Phe Ala Leu Gly Tyr Ala
410                 415                 420                 425 att cgg gat ctg tgt caa gct cgt gac tgt cag aac ccc aac gcc ttt     1469
Ile Arg Asp Leu Cys Gln Ala Arg Asp Cys Gln Asn Pro Asn Ala Phe
                430                 435                 440 caa cca tgg gag tta ctt ggt gtg cta aaa aat gtg aca ttc act gat     1517
Gln Pro Trp Glu Leu Leu Gly Val Leu Lys Asn Val Thr Phe Thr Asp
            445                 450                 455 gga tgg aat tca ttt cat ttt gat gct cat ggg gat tta aat act gga     1565
Gly Trp Asn Ser Phe His Phe Asp Ala His Gly Asp Leu Asn Thr Gly
        460                 465                 470 tat gat gtt gtg ctc tgg aag gag atc aat gga cac atg act gtc act     1613
Tyr Asp Val Val Leu Trp Lys Glu Ile Asn Gly His Met Thr Val Thr
475                 480                 485 aag atg gca gaa tat gac cta cag aat gat gtc ttc atc atc cca gat     1661
Lys Met Ala Glu Tyr Asp Leu Gln Asn Asp Val Phe Ile Ile Pro Asp
490                 495                 500                 505 cag gaa aca aaa aat gag ttc agg aat ctt aag caa att caa tct aaa     1709
Gln Glu Thr Lys Asn Glu Phe Arg Asn Leu Lys Gln Ile Gln Ser Lys
                510                 515                 520 tgc tcc aag gaa tgc agt cct ggg caa atg aag aaa act aca aga agt     1757
Cys Ser Lys Glu Cys Ser Pro Gly Gln Met Lys Lys Thr Thr Arg Ser
            525                 530                 535 caa cac atc tgt tgc tat gaa tgt cag aac tgt cct gaa aat cat tac     1805
Gln His Ile Cys Cys Tyr Glu Cys Gln Asn Cys Pro Glu Asn His Tyr
        540                 545                 550 act aat cag aca gat atg cct cat tgc ctt tta tgc aac aac aaa act     1853
```

```
                Thr Asn Gln Thr Asp Met Pro His Cys Leu Leu Cys Asn Asn Lys Thr
                    555                 560                 565 cac tgg gcc cct gtt agg agc act atg tgc ttt gaa aag gaa gtg gaa          1901
His Trp Ala Pro Val Arg Ser Thr Met Cys Phe Glu Lys Glu Val Glu
570                 575                 580                 585 tat ctc aac tgg aat gac tcc ttg gcc atc cta ctc ctg att ctc tcc          1949
Tyr Leu Asn Trp Asn Asp Ser Leu Ala Ile Leu Leu Leu Ile Leu Ser
                590                 595                 600 cta ctg gga atc ata ttt gtt ctg gtt gtt ggc ata ata ttt aca aga          1997
Leu Leu Gly Ile Ile Phe Val Leu Val Val Gly Ile Ile Phe Thr Arg
            605                 610                 615 aac ctg aac act ccc gtt gtg aaa tca tcc ggg gga tta aga gtc tgc          2045
Asn Leu Asn Thr Pro Val Val Lys Ser Ser Gly Gly Leu Arg Val Cys
        620                 625                 630 tat gtg atc ctt ctc tgt cat ttc ctc aat ttt gcc agc acg agc ttt          2093
Tyr Val Ile Leu Leu Cys His Phe Leu Asn Phe Ala Ser Thr Ser Phe
    635                 640                 645 ttc att gga gaa cca caa gac ttc aca tgt aaa acc agg cag aca atg          2141
Phe Ile Gly Glu Pro Gln Asp Phe Thr Cys Lys Thr Arg Gln Thr Met
650                 655                 660                 665 ttt gga gtg agc ttt act ctt tgc atc tcc tgc att ttg acg aag tct          2189
Phe Gly Val Ser Phe Thr Leu Cys Ile Ser Cys Ile Leu Thr Lys Ser
                670                 675                 680 ctg aaa att ttg cta gct ttc agc ttt gat ccc aaa tta cag aaa ttt          2237
Leu Lys Ile Leu Leu Ala Phe Ser Phe Asp Pro Lys Leu Gln Lys Phe
            685                 690                 695 ctg aag tgc ctc tat aga ccg atc ctt atc ttc act tgc acg ggc              2285
Leu Lys Cys Leu Tyr Arg Pro Ile Leu Ile Phe Thr Cys Thr Gly
        700                 705                 710 atc cag gtt gtc att tgc aca ctc tgg cta atc ttt gca gca cct act          2333
Ile Gln Val Val Ile Cys Thr Leu Trp Leu Ile Phe Ala Ala Pro Thr
    715                 720                 725 gta gag gtg aat gtc tcc ttg ccc aga gtc atc atc ctg gag tgt gag          2381
Val Glu Val Asn Val Ser Leu Pro Arg Val Ile Ile Leu Glu Cys Glu
730                 735                 740                 745 gag gga tcc ata ctt gca ttt ggc acc atg ctg ggc tac att gcc atc          2429
Glu Gly Ser Ile Leu Ala Phe Gly Thr Met Leu Gly Tyr Ile Ala Ile
                750                 755                 760 ctg gcc ttc att tgc ttc ata ttt gct ttc aaa ggc aaa tat gag aat          2477
Leu Ala Phe Ile Cys Phe Ile Phe Ala Phe Lys Gly Lys Tyr Glu Asn
            765                 770                 775 tac aat gaa gcc aaa ttc att aca ttt ggc atg ctc att tac ttc ata          2525
Tyr Asn Glu Ala Lys Phe Ile Thr Phe Gly Met Leu Ile Tyr Phe Ile
        780                 785                 790 gct tgg atc aca ttc atc cct atc tat gct acc aca ttt ggc aaa tat          2573
Ala Trp Ile Thr Phe Ile Pro Ile Tyr Ala Thr Thr Phe Gly Lys Tyr
    795                 800                 805 gta ccg gct gtg gag att att gtc ata tta ata tct aac tat gga atc          2621
Val Pro Ala Val Glu Ile Ile Val Ile Leu Ile Ser Asn Tyr Gly Ile
810                 815                 820                 825 ctg tat tgc aca ttc atc ccc aaa tgc tat gtt att att tgt aag caa          2669
Leu Tyr Cys Thr Phe Ile Pro Lys Cys Tyr Val Ile Ile Cys Lys Gln
                830                 835                 840 gag att aac aca aag tct gcc ttt ctc aag atg atc tac agt tat tct          2717
Glu Ile Asn Thr Lys Ser Ala Phe Leu Lys Met Ile Tyr Ser Tyr Ser
            845                 850                 855 tcc cat agt gtg agc agc att gcc ctg agt cct gct tca ctg gac tcc          2765
Ser His Ser Val Ser Ser Ile Ala Leu Ser Pro Ala Ser Leu Asp Ser
        860                 865                 870 atg agc ggc aat gtc aca atg acc aat ccc agc tct agt ggc aag tca          2813
```

```
Met Ser Gly Asn Val Thr Met Thr Asn Pro Ser Ser Gly Lys Ser
875                 880                 885 gca acc tgg cag aaa agc aaa gat ctt cag gca caa gca ttt gca cac       2861
Ala Thr Trp Gln Lys Ser Lys Asp Leu Gln Ala Gln Ala Phe Ala His
890                 895                 900                 905 ata tgc agg gaa aat gcc aca agt gta tct aaa act ttg cct cga aaa       2909
Ile Cys Arg Glu Asn Ala Thr Ser Val Ser Lys Thr Leu Pro Arg Lys
                910                 915                 920 aga atg tca agt ata tga ataagcctta ggagagatgc cacattccag              2957
Arg Met Ser Ser Ile *
                925 aataaaatgt tccagggtc tttgcatcta agatataaat ttactttccc agcaaatatg      3017 tcatatatat ttccttgcca ccatctttac caagttttag ttgaacagtc actctgttca     3077 atcacctatt taacaaatag aattgagcct tcagcctgaa gct                       3120

<210> SEQ ID NO 2
<211> LENGTH: 926
<212> TYPE: PRT
<213> ORGANISM: Homo sapiens

<400> SEQUENCE: 2

Met Ala Phe Leu Ile Ile Leu Ile Thr Cys Phe Val Ile Leu Ala
1               5                   10                  15

Thr Ser Gln Pro Cys Gln Thr Pro Asp Asp Phe Val Ala Ala Thr Ser
                20                  25                  30

Pro Gly His Ile Ile Ile Gly Gly Leu Phe Ala Ile His Glu Lys Met
                35                  40                  45

Leu Ser Ser Glu Asp Ser Pro Arg Arg Pro Gln Ile Gln Glu Cys Val
        50                  55                  60

Gly Phe Glu Ile Ser Val Phe Leu Gln Thr Leu Ala Met Ile His Ser
65                  70                  75                  80

Ile Glu Met Ile Asn Asn Ser Thr Leu Leu Ser Gly Val Lys Leu Gly
                85                  90                  95

Tyr Glu Ile Tyr Asp Thr Cys Thr Glu Val Thr Val Ala Met Ala Ala
                100                 105                 110

Thr Leu Arg Phe Leu Ser Lys Phe Asn Cys Ser Arg Glu Thr Val Glu
        115                 120                 125

Phe Lys Cys Asp Tyr Ser Ser Tyr Met Pro Arg Val Lys Ala Val Ile
130                 135                 140

Gly Ser Gly Tyr Ser Glu Ile Thr Met Ala Val Ser Arg Met Leu Asn
145                 150                 155                 160

Leu Gln Leu Met Pro Gln Val Gly Tyr Glu Ser Thr Ala Glu Ile Leu
                165                 170                 175

Ser Asp Lys Ile Arg Phe Pro Ser Phe Leu Arg Thr Val Pro Ser Asp
        180                 185                 190

Phe His Gln Ile Lys Ala Met Ala His Leu Ile Gln Lys Ser Gly Trp
        195                 200                 205

Asn Trp Ile Gly Ile Ile Thr Thr Asp Asp Tyr Gly Arg Leu Ala
210                 215                 220

Leu Asn Thr Phe Ile Ile Gln Ala Glu Ala Asn Asn Val Cys Ile Ala
225                 230                 235                 240

Phe Lys Glu Val Leu Pro Ala Phe Leu Ser Asp Asn Thr Ile Glu Val
                245                 250                 255

Arg Ile Asn Arg Thr Leu Lys Lys Ile Ile Leu Glu Ala Gln Val Asn
        260                 265                 270
```

-continued

Val Ile Val Val Phe Leu Arg Gln Phe His Val Phe Asp Leu Phe Asn
    275                 280                 285

Lys Ala Ile Glu Met Asn Ile Asn Lys Met Trp Ile Ala Ser Asp Asn
    290                 295                 300

Trp Ser Thr Ala Thr Lys Ile Thr Thr Ile Pro Asn Val Lys Lys Ile
305                 310                 315                 320

Gly Lys Val Val Gly Phe Ala Phe Arg Arg Gly Asn Ile Ser Ser Phe
                325                 330                 335

His Ser Phe Leu Gln Asn Leu His Leu Leu Pro Ser Asp Ser His Lys
                340                 345                 350

Leu Leu His Glu Tyr Ala Met His Leu Ser Ala Cys Ala Tyr Val Lys
            355                 360                 365

Asp Thr Asp Leu Ser Gln Cys Ile Phe Asn His Ser Gln Arg Thr Leu
    370                 375                 380

Ala Tyr Lys Ala Asn Lys Ala Ile Glu Arg Asn Phe Val Met Arg Asn
385                 390                 395                 400

Asp Phe Leu Trp Asp Tyr Ala Glu Pro Gly Leu Ile His Ser Ile Gln
                405                 410                 415

Leu Ala Val Phe Ala Leu Gly Tyr Ala Ile Arg Asp Leu Cys Gln Ala
                420                 425                 430

Arg Asp Cys Gln Asn Pro Asn Ala Phe Gln Pro Trp Glu Leu Leu Gly
            435                 440                 445

Val Leu Lys Asn Val Thr Phe Thr Asp Gly Trp Asn Ser Phe His Phe
    450                 455                 460

Asp Ala His Gly Asp Leu Asn Thr Gly Tyr Asp Val Val Leu Trp Lys
465                 470                 475                 480

Glu Ile Asn Gly His Met Thr Val Thr Lys Met Ala Glu Tyr Asp Leu
                485                 490                 495

Gln Asn Asp Val Phe Ile Ile Pro Asp Gln Glu Thr Lys Asn Glu Phe
                500                 505                 510

Arg Asn Leu Lys Gln Ile Gln Ser Lys Cys Ser Lys Glu Cys Ser Pro
            515                 520                 525

Gly Gln Met Lys Lys Thr Thr Arg Ser Gln His Ile Cys Cys Tyr Glu
    530                 535                 540

Cys Gln Asn Cys Pro Glu Asn His Tyr Thr Asn Gln Thr Asp Met Pro
545                 550                 555                 560

His Cys Leu Leu Cys Asn Asn Lys Thr His Trp Ala Pro Val Arg Ser
                565                 570                 575

Thr Met Cys Phe Glu Lys Glu Val Glu Tyr Leu Asn Trp Asn Asp Ser
                580                 585                 590

Leu Ala Ile Leu Leu Leu Ile Leu Ser Leu Leu Gly Ile Ile Phe Val
            595                 600                 605

Leu Val Val Gly Ile Ile Phe Thr Arg Asn Leu Asn Thr Pro Val Val
    610                 615                 620

Lys Ser Ser Gly Gly Leu Arg Val Cys Tyr Val Ile Leu Leu Cys His
625                 630                 635                 640

Phe Leu Asn Phe Ala Ser Thr Ser Phe Phe Ile Gly Glu Pro Gln Asp
                645                 650                 655

Phe Thr Cys Lys Thr Arg Gln Thr Met Phe Gly Val Ser Phe Thr Leu
                660                 665                 670

Cys Ile Ser Cys Ile Leu Thr Lys Ser Leu Lys Ile Leu Leu Ala Phe
            675                 680                 685

Ser Phe Asp Pro Lys Leu Gln Lys Phe Leu Lys Cys Leu Tyr Arg Pro
    690                 695                 700

```
Ile Leu Ile Ile Phe Thr Cys Thr Gly Ile Gln Val Val Ile Cys Thr
705                 710                 715                 720

Leu Trp Leu Ile Phe Ala Ala Pro Thr Val Glu Val Asn Val Ser Leu
            725                 730                 735

Pro Arg Val Ile Ile Leu Glu Cys Glu Glu Gly Ser Ile Leu Ala Phe
            740                 745                 750

Gly Thr Met Leu Gly Tyr Ile Ala Ile Leu Ala Phe Ile Cys Phe Ile
            755                 760                 765

Phe Ala Phe Lys Gly Lys Tyr Glu Asn Tyr Asn Glu Ala Lys Phe Ile
            770                 775                 780

Thr Phe Gly Met Leu Ile Tyr Phe Ile Ala Trp Ile Thr Phe Ile Pro
785                 790                 795                 800

Ile Tyr Ala Thr Thr Phe Gly Lys Tyr Val Pro Ala Val Glu Ile Ile
            805                 810                 815

Val Ile Leu Ile Ser Asn Tyr Gly Ile Leu Tyr Cys Thr Phe Ile Pro
            820                 825                 830

Lys Cys Tyr Val Ile Ile Cys Lys Gln Glu Ile Asn Thr Lys Ser Ala
            835                 840                 845

Phe Leu Lys Met Ile Tyr Ser Tyr Ser Ser His Ser Val Ser Ser Ile
            850                 855                 860

Ala Leu Ser Pro Ala Ser Leu Asp Ser Met Ser Gly Asn Val Thr Met
865                 870                 875                 880

Thr Asn Pro Ser Ser Gly Lys Ser Ala Thr Trp Gln Lys Ser Lys
            885                 890                 895

Asp Leu Gln Ala Gln Ala Phe Ala His Ile Cys Arg Glu Asn Ala Thr
            900                 905                 910

Ser Val Ser Lys Thr Leu Pro Arg Lys Arg Met Ser Ser Ile
            915                 920                 925

<210> SEQ ID NO 3
<211> LENGTH: 20
<212> TYPE: PRT
<213> ORGANISM: Artificial Sequence
<220> FEATURE:
<223> OTHER INFORMATION: synthetic construct

<400> SEQUENCE: 3

Ser Lys Phe Asn Cys Ser Arg Glu Thr Val Glu Phe Lys Cys Asp Tyr
1               5                   10                  15

Ser Ser Tyr Met
            20

<210> SEQ ID NO 4
<211> LENGTH: 20
<212> TYPE: PRT
<213> ORGANISM: Artificial Sequence
<220> FEATURE:
<223> OTHER INFORMATION: synthetic construct

<400> SEQUENCE: 4

Met Ala Glu Tyr Asp Leu Gln Asn Asp Val Phe Ile Ile Pro Asp Gln
1               5                   10                  15

Glu Thr Lys Asn
            20
```

CALCIUM-SENSING RECEPTOR 2 (CAR2) AND METHODS FOR USING

CROSS-REFERENCE TO RELATED APPLICATIONS

The present application is a continuation of U.S. patent application Ser. No. 11/784,976, filed Apr. 10, 2007, which is a continuation of U.S. patent application Ser. No. 10/283,842, filed Oct. 29, 2002 (abandoned), which claims the benefit of priority of U.S. Provisional Patent Application No. 60/421,941, filed Oct. 28, 2002 and which is related to U.S. patent application Ser. No. 10/283,656, filed on Oct. 29, 2002, the entire contents of each of which are incorporated by reference herein.

BACKGROUND OF THE INVENTION

Calcium is one of the most important regulatory molecules in the body because of its diverse intracellular and extracellular roles (bone mineralization; cofactor for adhesion molecules, clotting factors and additional proteins) (Brown, E. M., et al. (1999) Vitamin. Horm. 55, 1-71). For example, intracellular calcium, particularly the cytosolic free calcium concentration, is an important second messenger and cofactor for proteins and enzymes regulating a diverse set of key cellular processes. Intracellular calcium is utilized in the regulation of neurotransmission, motility, hormonal secretion and cellular proliferation. Extracellular calcium serves as a cofactor for adhesion molecules, clotting factors, and other proteins; regulates neuronal excitability; and is an essential part of the mineral phase of bone. The skeleton provides a structural framework that protects critical bodily structures and facilitates locomotion.

As a consequence of its critical roles the level of extracellular calcium ($Ca^{++}_0$) needs to be precisely regulated. The essential mechanism through which the metabolism of $Ca^{++}_0$ is maintained is regulation of dietary intake and absorption, in combination with $Ca^{++}$ handling in the microenvironments of the renal tubules and the skeleton.

The relatively recent identification of a calcium sensing receptor from bovine parathyroid (CaR) provided important information as to the signaling mechanism through which the body maintains $Ca^{++}$ homeostasis. CaR is 1085 amino acid residues in length and is a member of the G-protein coupled receptor family. CaR is made up of three distinct domains; an amino terminal hydrophilic domain; a central core domain, containing 7 transmembrane helices; and a carboxy terminal hydrophobic domain (for a review see, Chattopadhyah, N. (2000) Int. J. Biochem. & Cell Biol. 32, 789-804).

Whereas CaR function can explain most $Ca^{++}_0$ sensing (based on an approximate physiological $Ca^{++}$ concentration of 1 mM and a CaR $EC_{50}$ of 4.1 mM), this molecule does not adequately explain $Ca^{++}_0$-sensing in the essential kidney and bone environments where local concentrations can be as high as 40 mM. In kidney, raising peritubular but not luminal $Ca^{++}_0$ diminishes $Ca^{++}$ reabsorption in the thick ascending limb of Henle's loop. In bone, raising $Ca^{++}$ stimulates the function of bone-forming osteoblasts (Quarles, L. D. (1997) J. Bone Miner. Res. 12, 1971-1974) and inhibits bone resorption by osteoclasts (Zaidi, M., et al. (1989) Biochem. Biophys. Res. Commun. 183, 1461-1465).

G-protein-coupled, seven transmembrane receptors (GPCRs or 7™ receptors) comprise the largest superfamily of proteins in the body (approximately 750 human members based on the analysis of the rough draft of the human genome). The diversity amongst endogenous ligands is exceptional, including biogenic amines, peptides, glycoproteins, lipids, nucleotides, ions and proteases. As a consequence, GPCRs are potential targets for intervention in many disease areas and, not surprisingly, they represent the most important target class of proteins for drug discovery to date, with over 30% of clinically marketed drugs being active at this receptor family. As these drugs exhibit their activity upon less than 10% of all known GPCRs, it can be foreseen that this family has the potential to yield many more clinically relevant targets. Identification of the expression pattern and correct activating ligand are crucial in formulating hypotheses about biological function and pharmacological relevance of novel GPCRs.

GPCRs can be structurally classified into three major subfamilies that include the receptors related to the "light receptor" rhodopsin and the $\beta_2$-adrenergic receptor (family A), the receptors related to the glucagon receptor (family B) and the receptors related to the metabotropic neurotransmitter receptors (family C). Family C comprises three subgroups of GPCRs, with Group I including the metabotropic glutamate receptors 1-8, Group II including the Calcium-sensing receptor (CaR) and a multigene family of putative pheromone, taste and odorant receptors, and Group III including $GABA_B$ receptors. Generally, these subgroups show $\geq 20\%$ homology in their seven-transmembrane regions and posses extracellular ligand-binding domains (ECD) that are homologous to the bacterial periplasmic nutrient-binding proteins (PBPs).

OC is a vitamin K-dependent bone calcium binding protein also called bone gla protein (BGP). OC is a unique non collagenous protein of the extra cellular matrix of bone that is synthesized by the bone forming cells, the osteoblasts. Human OC is a relatively small protein composed of 49 amino acids and having a molecular weight of 5,800 daltons. OC was first discovered in the bones of chicken and bovine. Over 20 years ago, the human OC was isolated and its amino acid sequence was determined ((1980) The Journal of Biological Chemistry, Vol 255, No. 18, pp. 8685-8691). OC inhibits hydroxyapatite formation in vitro and is modulated by the calcium regulating hormone 1,25-dihydroxyvitamin D, but until the current study, its precise physiological functions remained unknown.

In view of the importance of calcium in both normal and pathological conditions, there is a ongoing need for the identification and biological characterization of additional members of the GPCR family in order to elucidate those members which are valuable drug targets, as well as prognostic and diagnostic markers for a variety of pathological processes.

SUMMARY OF THE INVENTION

The present invention is based, at least in part, on the identification and characterization of a novel human GPCR that structurally belongs to family C Group II. Following ectopic expression in mammalian cells, this GPCR was exposed to a wide variety of potential ligands and found to be activated by $Ca^{++}$. The receptor was termed Calcium-sensing Receptor 2 (CaR2).

CaR2 has been found to be expressed in environments where there are high levels of calcium. Immunohistochemical analysis has shown expression of CaR2 in bone, kidney, prostate, salivary, glands, testis, thymus, brain, trachea and thyroid. The present invention shows that OC synergistically activates CaR2.

Accordingly, OC is a novel drug target for conditions associated with CaR2. Therefore, the methods disclosed herein are useful for treatment of conditions associated with the above-mentioned tissues, including, but not limited to, extracellular calcium concentration, metabolic conditions associated with CaR2 or OC, osteoporosis, sperm motility and viability, regulation of calcium flux in the kidneys, kidney stone formation, regulation of calcium flux in the prostate, promotion of osteoblast proliferation, e.g., for the production of osteoblasts for medical use, metastasis of cancers, cancers, e.g., breast, renal, prostate and bone cancers, regulation of bone mineralization, bone overgrowth modulation of bone healing, e.g., dental caries, osteoporosis) and other bone formation diseases, and detection of a subset of cells, e.g., for forensic analysis.

The invention is also based, at least in part, on the discovery that CaR2 is modulated by OC(OC). OC is the most abundant non-collagenous protein of the extracellular matrix and is synthesized primarily by osteoblasts. Accordingly, CaR2 is a target for conditions associated with the formation and breakdown of the extracellular matrix, and conditions associated with aberrant expression of OC.

Accordingly, in one aspect, this invention provides isolated nucleic acid molecules encoding CaR2 polypeptides or biologically active portions thereof, as well as nucleic acid fragments suitable as primers or hybridization probes for the detection of CaR2-encoding nucleic acids.

In one embodiment, the invention features an isolated nucleic acid molecule that includes the nucleotide sequence set forth in SEQ ID NO:1. In another embodiment, the invention features an isolated nucleic acid molecule that encodes a polypeptide including the amino acid sequence set forth in SEQ ID NO:2.

In still other embodiments, the invention features isolated nucleic acid molecules including nucleotide sequences that are substantially identical (e.g., 30%, 35%, 40%, 45%, 50%, 55%, 60%, 65%, 70%, 75%, 80%, 85%, 90%, 91%, 92%, 93%, 94%, 95%, 96%, 97%, 98%, 99% identical) to the nucleotide sequence set forth as SEQ ID NO: 1. The invention further features isolated nucleic acid molecules including at least 50, 100, 150, 200, 300, 400, 500, 600, 700, 800, 900, 1000, 1500, 2000, 2500, 2600, 2700, 2800, or 2900 contiguous nucleotides of the nucleotide sequence set forth as SEQ ID NO:1. In another embodiment, the invention features isolated nucleic acid molecules which encode a polypeptide including an amino acid sequence that is substantially identical (e.g., 60% identical) to the amino acid sequence set forth as SEQ ID NO:2. The present invention also features nucleic acid molecules which encode allelic variants of the polypeptide having the amino acid sequence set forth as SEQ ID NO:2. In addition to isolated nucleic acid molecules encoding full-length polypeptides, the present invention also features nucleic acid molecules which encode fragments, for example, biologically active or antigenic fragments, of the full-length polypeptides of the present invention (e.g., fragments including at least 10 contiguous amino acid residues of the amino acid sequence of SEQ ID NO:2). In still other embodiments, the invention features nucleic acid molecules that are complementary to, antisense to, or hybridize under stringent conditions to the isolated nucleic acid molecules described herein.

In another aspect, the invention provides vectors including the isolated nucleic acid molecules described herein (e.g., CaR2-encoding nucleic acid molecules). Such vectors can optionally include nucleotide sequences encoding heterologous polypeptides. Also featured are host cells including such vectors (e.g., host cells including vectors suitable for producing CaR2 nucleic acid molecules and polypeptides).

The invention further provides nucleic acid constructs comprising the nucleic acid molecules described herein. In a preferred embodiment, the nucleic acid molecules of the invention are operatively linked to a regulatory sequence.

In another aspect, the invention features isolated CaR2 polypeptides and/or biologically active or antigenic fragments thereof. Exemplary embodiments feature a polypeptide including the amino acid sequence set forth as of SEQ ID NO:2, a polypeptide including an amino acid sequence at least 30%, 35%, 40%, 45%, 50%, 55%, 60%, 65%, 70%, 75%, 80%, 90%, 95%, 96%, 97%, 98%, 99% identical to the amino acid sequence set forth as of SEQ ID NO:2, a polypeptide encoded by a nucleic acid molecule including a nucleotide sequence at least 30%, 35%, 40%, 45%, 50%, 55%, 60%, 65%, 70%, 75%, 80%, 85%, 90%, 95%, 96%, 97%, 98%, 99% identical to the nucleotide sequence set forth as SEQ ID NO:1. Also featured are fragments of the full-length polypeptides described herein (e.g., fragments including at least 10, 25, 50, 100, 150, 200, 250, 300, 350, 400, 450, 500, 600, 700, 800, or 900 contiguous amino acid residues of the sequence set forth as of SEQ ID NO:2) as well as allelic variants of the polypeptide having the amino acid sequence set forth as SEQ ID NO:2.

The CaR2 polypeptides and/or biologically active or antigenic fragments thereof are useful, for example, as reagents or targets in assays applicable to treatment and/or diagnosis of calcium associated conditions. In one embodiment, a CaR2 polypeptide or fragment thereof, has a CaR2 activity.

Accordingly, it is an object of the invention to provide methods wherein CaR2 polypeptides are useful as reagents or targets in calcium sensing receptor assays that are applicable to treatment and diagnosis of conditions related to calcium flux, or related to, CaR2.

It is a further object of the invention to provide methods wherein polynucleotides corresponding to the CaR2 polypeptides are useful as probes, targets or reagents that are applicable to treatment and diagnosis of conditions related CaR2.

A specific object of the invention is to identify compounds that act as agonists and antagonists and modulate the expression or activity of CaR2 in cells or tissues. Such compounds can be used to prevent, or treat conditions mediated by, or related to, CaR2.

Accordingly, in one aspect the invention provides methods of screening for compounds that modulate expression or activity of the CaR2 polypeptides or nucleic acids (RNA or DNA) in cells or tissues. In certain embodiments, the cells or tissues are derived from cells or tissues in which CaR2 expression or activity has been altered, e.g., from animals or individuals having a disorder mediated by or related to CaR2.

A further object of the invention is to provide compounds that modulate expression or activity of CaR2 for treatment and diagnosis of conditions mediated by or related to CaR2, such as the conditions disclosed herein.

The invention also utilizes vectors and host cells that express CaR2 and provides methods for expressing CaR2 nucleic acid molecules and polypeptides in cells, and particularly recombinant vectors and host cells.

The invention also utilizes methods of making the vectors and host cells and provides methods for using them to assay expression and cellular effects of expression of the CaR2 nucleic acid molecules and polypeptides in specific cell types and conditions.

The invention also utilizes antibodies or antigen-binding fragments thereof that selectively bind the CaR2 polypeptides and fragments.

A specific object of the invention is to identify compounds that act as agonists and antagonists and modulate the expression or activity of CaR2 in cells or tissues. Such compounds can be used to alter conditions mediated by, or related to, CaR2. Accordingly, in one aspect the invention provides methods of screening for compounds that modulate expression or activity of the CaR2 polypeptides or nucleic acids (RNA or DNA) in cells or tissues. In certain embodiments, the cells or tissues are derived from cells or tissues in which CaR2 expression or activity has been altered, e.g., from animals or individuals having a disorder mediated by or related to CaR2.

It is further an object of the invention to provide compounds that modulate the ability of CaR2 to bind OC for the treatment of conditions mediated by, or related to CaR2, e.g., metastasis of cancer.

A further object of the invention is to provide compounds that modulate expression or activity of CaR2 for treatment and diagnosis of conditions mediated by or related to CaR2, such as the conditions disclosed herein.

The invention also provides a process for modulating CaR2 polypeptides or nucleic acid expression or activity, especially using the screened compounds. Modulation can be used to treat conditions related to aberrant activity or expression of the CaR2 polypeptides or nucleic acids.

The invention further provides assays for determining the activity of, or the presence or absence of CaR2 polypeptides or nucleic acid molecules in biological samples, including for diagnosing conditions disclosed herein.

The invention also provides assays for determining the presence of a mutation in CaR2 polypeptides or nucleic acid molecules, including for diagnosing conditions disclosed herein.

The invention utilizes isolated CaR2 polypeptides, including a polypeptide having the amino acid sequence shown in SEQ ID NO 2.

The invention also utilizes isolated CaR2 nucleic acid molecule having the sequence shown in SEQ ID NO:1 or a complement thereof.

The invention also utilizes variant polypeptides having an amino acid sequence that is substantially homologous to the amino acid sequence shown in SEQ ID NO:2.

The invention also utilizes variant nucleic acid sequences that are substantially homologous to the nucleotide sequence shown in SEQ ID NO 1.

The invention also utilizes fragments of the polypeptide shown in SEQ ID NO:2 and nucleotide sequence shown in SEQ ID NO:1, complements of the nucleotide sequence shown in SEQ ID NO 1, as well as substantially homologous fragments of the polypeptide or nucleic acid.

The invention further utilizes nucleic acid constructs comprising the nucleic acid molecules described herein. In certain embodiments, the nucleic acid molecules of the invention are operatively linked to a regulatory sequence.

The invention also utilizes vectors and host cells that express CaR2 and provides methods for expressing CaR2 nucleic acid molecules and polypeptides in cells, and particularly recombinant vectors and host cells.

The invention also utilizes methods of making the vectors and host cells and provides methods for using them to assay expression and cellular effects of expression of the CaR2 nucleic acid molecules and polypeptides in specific cell types and conditions.

The invention also utilizes antibodies or antigen-binding fragments thereof that selectively bind the CaR2 polypeptides and fragments.

DESCRIPTION OF THE DRAWINGS

FIG. 1 shows the nucleotide (SEQ ID NO:1) and the deduced amino acid sequence (SEQ ID NO:2) of CaR2.

FIG. 4 shows CaR2 activation by $Ca^{++}$. CaR2 is robustly activated by 40 mM $Ca^{++}$, whereas there is modest activation by 10 mM $Ca^{++}$. OC(OC) activates CaR2 when pre-incubated with 10 mM $Ca^{++}$ in a dose-dependent manner. OC activation of CaR2 is reversed when OC and $Ca^{2+}$ are pre-incubated with $Pb^{2+}$, which is known to prevent the formation of OC/$Ca^{++}$ complexes.

FIG. 5A shows multiple well overlay showing activation by BMP-2 and CT of recombinant CaR2. FIG. 5B shows activation by BMP-2 and CT is delayed, and falls out of the range of direct GPCR activation as recorded by FLIPR.

DETAILED DESCRIPTION OF THE INVENTION

Figure 2:
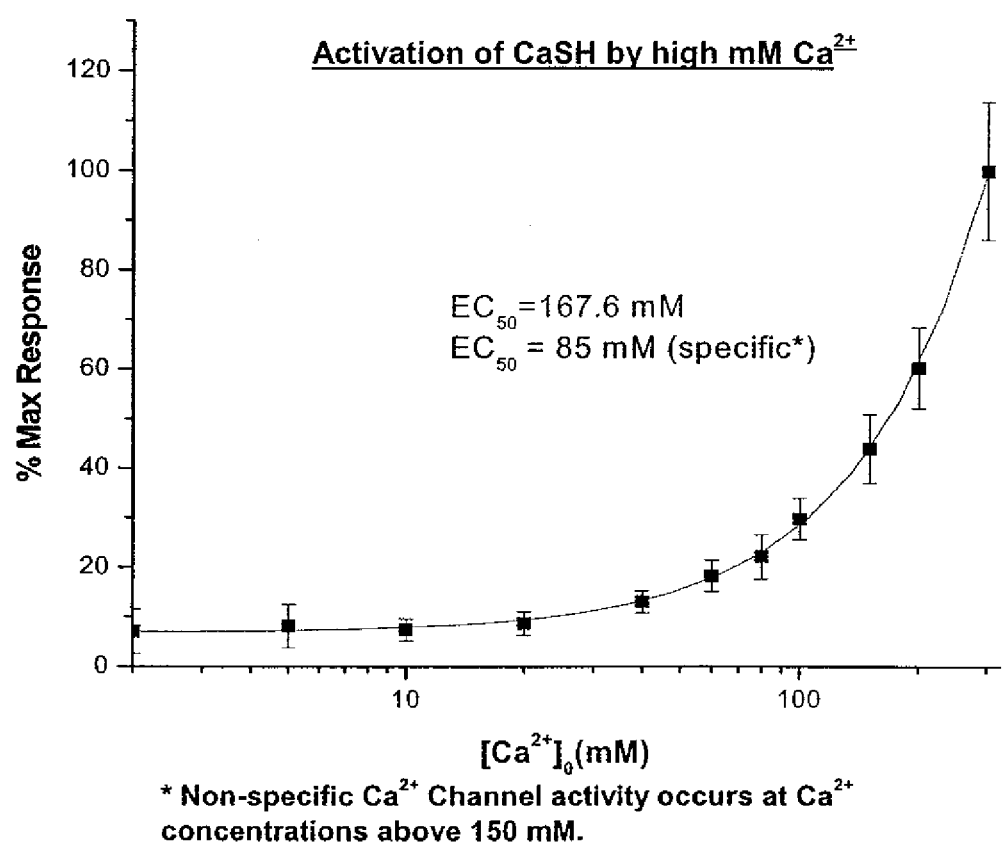
FIG. 2 shows recombinant CaR2 expressed in HEK 293 cells is activated by high concentrations of $Ca^{++}$.

Applicants have discovered a novel calcium-sensing receptor, designated CaR2, that is pharmacologically distinct from previously identified calcium receptors. CaR2 localizes to bone (osteoblasts), kidney (apical side of epithelial cells in the thick ascending limb of Henle's loop), and prostate (epithelial duct lining cells), as determined immunohistochemically. OC(OC) increases the sensitivity of CaR2 to $Ca^{++}$, while OC in the absence of calcium does not activate CaR2.

CaR2 is expressed prominently in kidney and prostate, tissues that show a high frequency of skeletal metastases (Brage M E and Simon M A. (1992) Orthopedics 15(5):589-96; Miric A, et al. (1998) J Surg Oncol (4):255-60). Unique among these metastatic tumors, skeletal metastasis of primary prostate cancers display osteoblastic, rather than osteolytic, functions and this osteoblastic character has been hypothesized to result from tumor expression of bone regulatory molecules (e.g. BMP6). CaR2 and OC expressing osteoblastic cells have a survival and proliferative advantage when challenged with the high concentration of free Ca++ that activates CaR2 and that is normally present in mineralizing bone. It is reasonably predictable that CaR2 expression in cells from other tissues confers on those cells a preference for and a survival advantage in high calcium environments. For example, the CaR2 expression that is seen in kidney and prostate epithelial cells would be expected to allow cancer cells from these epithelia a similar preference for and survival advantage in the bone environment, and this could explain the reported propensity to bone metastases for these primary cancers. In addition, the OC/Ca++ interaction with CaR2 could serve a chemoattractive function, fomenting the attraction of metastasizing kidney and prostate cancer cells toward the high OC/Ca++ signals that originate from bone.

CaR2 has been found to be expressed in environments where there are high levels of calcium. Immunohistochemical analysis has shown expression of CaR2 in bone, kidney, prostate, salivary, glands, testis, thymus, brain, trachea and thyroid.

The identification of CaR2 as a high concentration calcium sensor that is expressed in the epithelial ducts in kidney and prostate, and in bone tissue, allows for the physiological consequences expected to result from CaR2 hypo- and hyperactivity to be monitored. Normocalcemia in mammals and other tetrapods is believed to be maintained primarily through actions of CaR. Specific activating and inactivating mutations in CaR lead to hyper- and hypocalcemic disease states. In analogy with CaR, such mutations in CaR2 would be expected to strongly influence its specific microenvironments, such as kidney and bone. In kidney, CaR2 should respond to the $Ca^{++}$ concentration in fluids passing through the kidney tubules, resulting in either reabsorbtion of $Ca^{++}$ or its secretion in urine. Dysregulation leads to excessive calcium loss or the formation of kidney stones. Similarly, osteoblast CaR2 activation would be expected to affect bone formation and bone mass. Accordingly, using drugs to modulate CaR2 activity would be expected to have therapeutic benefit for conditions such as the conditions disclosed herein.

CaR2 dysfunction in prostate disrupts fertility by leading to abnormal $Ca^{++}$ levels in seminal fluid. Changes in CaR2 function also have pathological consequences in tissues in which CaR2 is not expressed. For example, CaR2 dysfunction leads to global disruption of $Ca^{++}_o$ homeostasis and influence the overall health and physiology of the organism by causing secondary pathology in distant organs and cells.

Activation of CaR2 by $Ca^{++}$ and the modulatory effect of OC, in combination with its cellular expression pattern, indicate a unique role for CaR2 in the pharmacology of $Ca^{++}$ homeostasis in microenvironments where $Ca^{++}$ levels are high. This role is expected to provide novel approaches for therapeutic intervention in key pathological processes. Moreover, this finding indicates a role of CaR2 in the metastasis of cancers to bone.

CaR2 is pharmacologically distinct from the previously identified Calcium-sensing Receptor (CaR) (for recent reviews see, Brown, E. M., et al., (1993) Nature 366, 575-580; Chattopadhyay N. (2000) Int. J. Biochem. & Cell Biol. 32, 789-804; Brown, E. M. (2000) Annu. Rev. Nutr. 20, 507-533) with an $EC_{50}$ value for $Ca^{++}$ (85 mM) that is much greater than that of CaR (4 mM). Consistent with a functional role in high $Ca^{++}$ environments, CaR2 localizes to bone (osteoblasts), kidney (apical side of epithelial cells in the thick ascending limb of Henle's loop), and prostate (epithelial duct lining cells), as determined immunohistochemically. Prior to the studies presented herein, OC thought to be only a structural protein. The present invention, for the first time, identifies the receptor associated with OC. OC increases the sensitivity of CaR2 to $Ca^{++}$, while OC in the absence of calcium does not activate CaR2. Genetic studies have indicated that OC functions as an inhibitor of osteoblast function, but no experimental evidence had implicated OC in signal transduction prior to the present invention.

The ability of OC to stimulate CaR2 signal transduction was unexpected and surprising. OC is a protein that is secreted by osteoblasts, and that has been identified as a structural component of the extracellular bone matrix (osteoid) and of mineralized bone. Secreted OC is thought to play an integral part in organizing the formation of osteoid and mineralized bone, both as a structural component of osteoid and as a nucleus for mineralization. In this role, OC remains in the osteoid matrix during bone mineralization to become an integral part of the mineralized bone matrix. However, OC is asymmetrically distributed in bone, with enrichment in highly mineralized and metabolically less active cortical bone, while trabecular bone is enriched in osteonectin. This asymmetry in the distribution of OC and other noncollagenous proteins has led to speculation that these proteins in bone might have regulatory functions in addition to their functions in bone structure and mineralization.

In addition to the likely influence of CaR2 on bone, kidney and prostate function, the receptor may also act as a survival factor in high calcium environments. In this role, CaR2 influences the cell cycle in response to $Ca^{++}$ or to other signals (e.g., protein ligands like OC). CaR2 regulation of cell proliferation, differentiation and cell survival in response to extracellular $Ca^{++}$ and/or protein ligands could help determine the tumorigenic potential of prostate, kidney or bone cells. Bone marrow is known to be a major homing site for metastasis of primary epithelial cancers of breast, colon, kidney and prostate. Clear cell renal carcinomas and epithelial prostate cancers show a particularly efficient ability to colonize bone. Numerous explanations for the bone tropism of these metastasis have been advanced, including suggestions that tumor cell survival rather than attraction is promoted by the environment in target tissues, that tumor cells can be trapped by favorable cell adhesive interactions within target tissues, and that chemokines could actively attract cancer cells to bone and other preferred metastases tissue destinations. CaR2 is expressed prominently in kidney and prostate, tissues that show a high frequency of skeletal metastasis. Unique among these metastatic tumors, skeletal metastasis of primary prostate cancers display osteoblastic, rather than osteolytic, functions.

Accordingly, in one aspect, the invention pertains to compositions that are able to inhibit CaR2 mediated conditions, e.g., the metastasis of tumors by interacting with CaR2. These compounds can be, for example, small molecules, peptides, e.g., calcium analogs, OC, a fragment of OC, or peptidomimetics.

In one aspect, the invention provides methods and reagents for diagnosing conditions associated with calcium receptors such as the conditions disclosed herein. The diagnostic and prognostic assays of this invention include methods involving antibody-based detection of CaR2 polypeptides, and nucleic acid-based detection of CaR2 mRNA and DNA.

In one embodiment, this invention provides a method for identifying conditions associated with CaR2 such as the conditions disclosed herein, comprising: assessing the level of CaR2 in a biological sample from the subject, wherein an elevation or reduction in the level of CaR2 is indicative of a disorder related to aberrant expression or activity of a calcium receptor.

In one embodiment, this invention provides a method for treating subjects with conditions caused by aberrant expression of OC. Since OC potentiates the response of CaR2 to Ca++, the current invention provides methods for treating individuals with conditions caused by aberrant expression of OC by modulating CaR2.

In another embodiment, this invention provides a method for identifying conditions associated with calcium receptors, such as the conditions disclosed herein, comprising: assessing the level of CaR2 in a biological sample from the subject, wherein an elevation in the level of CaR2 is indicative of a disorder related to calcium receptors.

In a further related embodiment, this invention provides a method for identifying metastatic cancer in a subject, comprising: assessing the level of CaR2 in a biological sample from the subject, wherein an elevation in the level of CaR2 is indicative of cancer, and wherein the subject was previously identified as having cancer, e.g., prostate or kidney cancer.

Further, provided by this invention are the above methods, wherein assessing the level of CaR2 in a biological sample from the subject includes contacting the biological sample with an antibody to CaR2 or a fragment thereof; determining the amount of binding of the antibody to the biological sample; and comparing the amount of antibody bound to the biological sample to a predetermined base level. The amount of binding of the antibody to the biological sample can be determined by the intensity of the signal emitted by the labeled antibody and/or by the number cells in the biological sample bound to the labeled antibody.

Also encompassed by this invention are the above methods wherein the level of CaR2 is assessed by detecting a level of CaR2 nucleic acid in a biological sample; and comparing the level of CaR2 in the biological sample with a level of CaR2 in a control sample. For example, in certain embodiments CaR2 nucleic acid is detected using hybridization probes and/or nucleic acid amplification methods.

The diagnostic and prognostic assays of this invention can be further used in combination with other methods of diagnosing conditions disclosed herein. Examples of diagnostic methods that can be used in combination with the assays of the invention include, but are not limited to, current diagnostic methods known to medical practitioners skilled in the art such as ultrasonography or magnetic resonance imaging (MRI), bone scanning, X-rays, skeletal survey, intravenous pyelography, CAT-scan, and biopsy.

The present invention also includes methods of determining whether a subject is likely to respond to a treatment regimen comprising agents, or modulators which have a stimulatory or inhibitory effect on CaR2 activity (e.g., CaR2 gene expression or enzyme activity). For example, CaR2 inhibitors can be administered to individuals, such as those identified using the diagnostic and prognostic methods of the invention as having elevated levels of CaR2, to treat (prophylactically or therapeutically) conditions associated with aberrant CaR2 activity or level.

The invention also provides methods for diagnosing active conditions, or predisposition to conditions, in a patient having a variant CaR2. Thus, CaR2 can be isolated from a biological sample and assayed for the presence of a genetic mutation that results in an aberrant protein. This includes amino acid substitution, deletion, insertion, rearrangement, (as the result of aberrant splicing events), and inappropriate post-translational modification. Analytic methods include altered electrophoretic mobility, altered tryptic peptide digest, altered activity in cell-based or cell-free assay, alteration in ligand binding, or antibody-binding pattern, altered isoelectric point, direct amino acid sequencing, and any other of the known assay techniques useful for detecting mutations in a protein in general or in a calcium sensing receptor specifically. Mutations resulting in aberrant levels of CaR2 expression can be further identified using standard nucleic acid detection techniques such as those described herein. Mutations resulting in aberrant CaR2 protein activity can be further identified by assays measuring the response of a cell to calcium, such as, but not limited to those described herein.

The invention also encompasses kits for detecting the presence of a CaR2 polypeptide or nucleic acid in a biological sample according to the methods described herein. For example, the kit can comprise a labeled compound or agent capable of detecting CaR2 polypeptide or an mRNA encoding a CaR2 in a biological sample and means for determining the amount of the CaR2 polypeptide or CaR2 mRNA in the sample (e.g., an antibody which binds the polypeptide or an oligonucleotide probe which binds to DNA or mRNA encoding CaR2). Kits can also include immunomagnetic beads that can be used to facilitate serum assays. Kits can further include instructions for carrying out the methods of the invention and/or for interpreting the results obtained from using the kit.

For example, antibody-based kits can comprise: (1) a first antibody (e.g., attached to a solid support) which binds to a CaR2 polypeptide; and, optionally, (2) a second, different antibody which binds to either the CaR2 polypeptide or the first antibody and is conjugated to a detectable label. Nucleic acid-based-kits can comprise, for example: (1) an oligonucleotide, e.g., a detectably labeled oligonucleotide, which hybridizes to a nucleic acid encoding CaR2 or (2) a pair of primers useful for amplifying a nucleic acid molecule encoding CaR2. Kits can also comprise a buffering agent, a preservative, or a protein stabilizing agent, components necessary for detecting the detectable label (e.g., an enzyme or a substrate), a control sample or a series of control samples which can be assayed and compared to the biological sample. Each component of the kit can also be enclosed within an individual container, and all of the various containers can be within a single package, along with instructions for interpreting the results of the assays performed using the kit.

In another aspect the invention provides methods for identifying modulators of CaR2 protein activity or CaR2 gene expression. These modulators can be used in the treatment of CaR2 and OC related conditions such as those described herein.

Accordingly, in certain embodiments, the invention provides methods for identifying agents that interact with the CaR2 protein. This interaction can be detected by functional assays, such as assays for calcium receptor activity. Determining the ability of the test compound to interact with CaR2 can also comprise determining the ability of the test compound to preferentially bind to the polypeptide as compared to the ability of a known binding molecule to bind the polypeptide.

In related embodiments, the invention provides methods to identify agents that modulate calcium receptor activity. Such agents, for example, can increase or decrease affinity or rate of binding to substrate, e.g., OC, calcium, G-protein, for binding to the CaR2, or displace the substrate bound to the calcium receptor. For example, both CaR2 and appropriate variants and fragments can be used in high-throughput screens to assay candidate compounds for the ability to bind to the receptor. These compounds can be further screened against a functional CaR2 to determine the effects of the compound on the receptor activity. Compounds can be identified that activate (agonist) or inactivate (antagonist) the receptor to a desired degree. Modulatory methods can be performed in vitro (e.g., by culturing the cell with the agent) or, alternatively, in vivo (e.g., by administering the agent to a subject). The subject can be a human subject, for example, a subject in a clinical trial or undergoing treatment or diagnosis, or a non-human transgenic subject, such as a transgenic animal or a non-human non-transgenic animal.

Accordingly, the invention provides methods to screen a compound for the ability to stimulate or inhibit interaction between the receptor protein and a target molecule that normally interacts with the receptor protein. The assay includes the steps of combining the receptor protein with a candidate compound under conditions that allow the receptor or fragment to interact with the target molecule, and to detect the formation of a complex between the receptor and the target, or to detect the biochemical consequence of the interaction with the receptor and the target.

In further related embodiments, the invention provides drug screening assays, in cell-based or cell-free systems. Cell-based systems can be native, i.e., cells that normally express the CaR2, as a biopsy, or expanded in cell culture. In one embodiment, cell-based assays involve recombinant host cells expressing CaR2. Accordingly, cells that are useful in this regard include, but are not limited to, cells differentially expressing CaR2 (e.g., metastasic cells). These include, but are not limited to, cells or tissues derived from an individual having an CaR2 disorder (e.g., cancerous tissue or tumors, bone). Such cells can naturally express the gene or can be recombinant. Recombinant cells include cells containing one or more copies of exogenously-introduced CaR2 sequences, or cells that have been genetically modified to modulate expression of the endogenous CaR2 sequence.

In these embodiments, the invention particularly relates to cells derived from subjects with conditions involving the tissues in which CaR2 is expressed or derived from tissues subject to conditions including, but not limited to, those disclosed herein. These conditions may naturally occur, as in populations of human subjects, or may occur in model systems such as in vitro systems or in vivo, such as in non-human transgenic organisms, particularly in non-human transgenic animals.

In yet another aspect of the invention, the invention provides methods to identify proteins that interact with the calcium receptor in the tissues and conditions disclosed. For example, the proteins of the invention can be used as "bait proteins" in a two-hybrid assay or three-hybrid assay (see, e.g., U.S. Pat. No. 5,283,317; Zervos et al. (1993) Cell 72:223-232; Madura et al. (1993) J. Blod. Chem. 268:12046-12054; Bartel et al. Biotechniques 14:920-924; Iwabuchi et al. (1993) Oncogene 8:1693-1696; and Brent, W O 94/10300), to identify other proteins (captured proteins) which bind to or interact with the proteins of the invention and modulate their activity.

I. CaR2 Reagents

A. CaR2 Polypeptides

"CaR2 polypeptide" or "CaR2 protein" refers to the polypeptide in SEQ ID NO:2 (FIG. 1). This protein contains 926 amino acids. Alignment of this sequence with sequences of the other members of the GPCR subfamily C indicates that CaR2 possesses all of the characteristic domains of the other GPCR subfamily C proteins including a large N-terminal ECD and a C-terminal transmembrane domain.

Accordingly, the term "CaR2 protein" or "CaR2 polypeptide", further includes fragments derived from the full-length CaR2s including various domains, as well as the numerous variants described herein.

The present invention thus utilizes an isolated or purified CaR2 polypeptide and variants and fragments thereof. As used herein, a polypeptide is said to be "isolated" or "purified" when it is substantially free of cellular material, when it is isolated from recombinant and non-recombinant cells, or free of chemical precursors or other chemicals when it is chemically synthesized. A polypeptide, however, can be joined to another polypeptide with which it is not normally associated in a cell and still be considered "isolated" or "purified."

The CaR2 polypeptides can be purified to homogeneity. It is understood, however, that preparations in which the polypeptide is not purified to homogeneity are useful and considered to contain an isolated form of the polypeptide. The critical feature is that the preparation allows for the desired function of the polypeptide, even in the presence of considerable amounts of other components. Thus, the invention encompasses various degrees of purity.

In one embodiment, the language "substantially free of cellular material" includes preparations of CaR2 having less than about 30% (by dry weight) other proteins (i.e., contaminating protein), less than about 20% other proteins, less than about 10% other proteins, or less than about 5% other proteins. When the polypeptide is recombinantly produced, it can also be substantially free of culture medium, i.e., culture medium represents less than about 20%, less than about 10%, or less than about 5% of the volume of the protein preparation.

A CaR2 polypeptide is also considered to be isolated when it is part of a membrane preparation or is purified and then reconstituted with membrane vesicles or liposomes.

The language "substantially free of chemical precursors or other chemicals" includes preparations of CaR2 polypeptide in which it is separated from chemical precursors or other chemicals that are involved in its synthesis. In one embodiment, the language "substantially free of chemical precursors or other chemicals" includes preparations of the polypeptide having less than about 30% (by dry weight) chemical precursors or other chemicals, less than about 20% chemical precursors or other chemicals, less than about 10% chemical precursors or other chemicals, or less than about 5% chemical precursors or other chemicals.

In one embodiment, the CaR2 polypeptide comprises the amino acid sequence shown in SEQ ID NO:2. However, the invention also encompasses sequence variants. Variants include a substantially homologous protein encoded by the same genetic locus in an organism, i.e., an allelic variant.

Variants also encompass proteins derived from other genetic loci in an organism, but having substantial homology to the CaR2 of SEQ ID NO:2. Variants also include proteins substantially homologous to CaR2 but derived from another organism, i.e., an ortholog. Variants also include proteins that are substantially homologous to CaR2 that are produced by chemical synthesis. Variants also include proteins that are substantially homologous to CaR2 that are produced by recombinant methods. It is understood, however, that variants exclude any amino acid sequences disclosed prior to the invention.

As used herein, two proteins (or a region of the proteins) are substantially homologous when the amino acid sequences are at least about 70-75%, typically at least about 80-85%, and most typically at least about 90-95%, 97%, 98% or 99% or more homologous. A substantially homologous amino acid sequence, according to the present invention, will be encoded by a nucleic acid sequence hybridizing to the nucleic acid sequence, or portion thereof, of the sequence shown in SEQ ID NO:1 under stringent conditions as more fully described below.

To determine the percent identity of two amino acid sequences or of two nucleic acid sequences, the sequences are aligned for optimal comparison purposes (e.g., gaps can be introduced in one or both of a first and a second amino acid or nucleic acid sequence for optimal alignment and non-homologous sequences can be disregarded for comparison purposes). In a preferred embodiment, the length of a reference sequence aligned for comparison purposes is at least 30%, preferably at least 40%, more preferably at least 50%, even more preferably at least 60%, and even more preferably at least 70%, 80%, or 90% or more of the length of the reference sequence. The amino acid residues or nucleotides at corresponding amino acid positions or nucleotide positions are then compared. When a position in the first sequence is occupied by the same amino acid residue or nucleotide as the corresponding position in the second sequence, then the molecules are identical at that position (as used herein amino acid or nucleic acid "Identity" is equivalent to amino acid or nucleic acid "homology"). The percent identity between the two sequences is a function of the number of identical positions shared by the sequences, taking into account the number of gaps, and the length of each gap, which need to be introduced for optimal alignment of the two sequences.

The invention also encompasses polypeptides having a lower degree of identity but having sufficient similarity so as to perform one or more of the same functions performed by CaR2. Similarity is determined by conserved amino acid substitution. Such substitutions are those that substitute a given amino acid in a polypeptide by another amino acid of like characteristics. Conservative substitutions are likely to be phenotypically silent. Typically seen as conservative substitutions are the replacements, one for another, among the aliphatic amino acids Ala, Val, Leu, and Ile; interchange of the hydroxyl residues Ser and Thr, exchange of the acidic residues Asp and Glu, substitution between the amide residues Asn and Gln, exchange of the basic residues Lys and Arg and replacements among the aromatic residues Phe, Tyr. Guidance concerning which amino acid changes are likely to be phenotypically silent are found in Bowie et al., Science 247: 1306-1310 (1990).

TABLE 1

Conservative Amino Acid Substitutions.

| | |
|---|---|
| Aromatic | Phenylalanine |
| | Tryptophan |
| | Tyrosine |
| Hydrophobic | Leucine |
| | Isoleucine |
| | Valine |
| Polar | Glutamine |
| | Asparagine |
| Basic | Arginine |
| | Lysine |
| | Histidine |
| Acidic | Aspartic Acid |
| | Glutamic Acid |
| Small | Alanine |
| | Serine |
| | Threonine |
| | Methionine Glycine |

The comparison of sequences and determination of percent identity and similarity between two sequences can be accomplished using a mathematical algorithm. (*Computational Molecular Biology*, Lesk, A. M., ed., Oxford University Press, New York, 1988; *Biocomputing: Informatics and Genome Projects*, Smith, D. W., ed., Academic Press, New York, 1993; *Computer Analysis of Sequence Data, Part 1*, Griffin, A. M., and Griffin, H G., eds., Humana Press, New Jersey, 1994; *Sequence Analysis in Molecular Biology*, van Heinje, G., Academic Press, 1987; and *Sequence Analysis Primer*, Gribskov, M. and Devereux, J., eds., M Stockton Press, New York, 1991).

A preferred, non-limiting example of such a mathematical algorithm is described in Karlin et al (1993) *Proc. Natl. Acad Sci*. USA 90:5873-5877. Such an algorithm is incorporated into the NBLAST and XBLAST programs (version 2.0) as described in Altschul et al (1997) *Nucleic Acids Res*. 25:3389-3402. When utilizing BLAST and Gapped BLAST programs, the default parameters of the respective programs (e.g., NBLAST) can be used. In one embodiment, parameters for sequence comparison can be set at score=100, wordlength=12, or can be varied (e.g., W=5 or W=20).

In a preferred embodiment, the percent identity between two amino acid sequences is determined using the Needleman et al. (1970) (*J. Mol. Biol*. 48:444-453) algorithm which has been incorporated into the GAP program in the GCG software package using either a BLOSUM 62 matrix or a PAM250 matrix, and a gap weight of 16, 14, 12, 10, 8, 6, or 4 and a length weight of 1, 2, 3, 4, 5, or 6. In yet another preferred embodiment, the percent identity between two nucleotide sequences is determined using the GAP program in the GCG software package (Devereux et al. (1984) *Nucleic Acids Res*. 12(1):387), using a NWSgapdna.CMP matrix and a gap weight of 40, 50, 60, 70, or 80 and a length weight of 1, 2, 3, 4, 5, or 6.

Another preferred, non-limiting example of a mathematical algorithm utilized for the comparison of sequences is the algorithm of Myers and Miller, CABIOS (1989). Such an algorithm is incorporated into the ALIGN program (version 2.0) which is part of the GCG sequence alignment software package. When utilizing the ALIGN program for comparing amino acid sequences, a PAM120 weight residue table, a gap length penalty of 12, and a gap penalty of 4 can be used. Additional algorithms for sequence analysis are known in the art and include ADVANCE and ADAM as described in Torellis et al. (1994) *Comput. Appl. Biosci*. 10:3-5, and FASTA described in Pearson et al. (1988) *PNAS* 85:2444-8.

A variant polypeptide can differ in amino acid sequence by one or more substitutions, deletions, insertions, inversions, fusions, and truncations or a combination of any of these. Variant polypeptides can be fully functional or can lack function in one or more activities. Thus, in the present case, variations can affect the function, for example, of one or more of the regions corresponding to the prodomain, the extracellular domain, the extracellular loops, the transmembrane domain or the C-terminal domain. Fully functional variants typically contain only conservative variation or variation in non-critical residues or in non-critical regions. Functional variants can also contain substitution of similar amino acids, which results in no change or an insignificant change in function. Alternatively, such substitutions may positively or negatively affect function to some degree. The activity of such functional variants can be determined using assays that are standard in the art, such as those described herein.

Non-functional variants typically contain one or more non-conservative amino acid substitutions, deletions, insertions, inversions, or truncation or a substitution, insertion, inversion, or deletion in a critical residue or critical region.

As indicated, variants can be naturally-occurring or can be made by recombinant means or chemical synthesis to provide useful and novel characteristics for CaR2 polypeptide. This includes preventing immunogenicity from pharmaceutical formulations by preventing protein aggregation.

Useful variations further include alteration of catalytic activity. For example, one embodiment involves a variation at the binding site that results in binding but not calcium receptor activity. A further useful variation at the same site can result in altered affinity for substrate. Another useful variation provides a fusion protein in which one or more domains or subregions are operationally fused to one or more domains or subregions from another CaR2 isoform or family.

Amino acids that are essential for function can be identified by methods known in the art, such as site-directed mutagenesis or alanine scanning mutagenesis (Cunningham et al. (1995) *Science* 244:1081-85). The later procedure introduces single alanine mutations at every residue in the molecule. The relusting mutant is then tested for biological activity. Sites that are critical for activity for calcium binding or interaction with OC can be determined by structural analysis such as crystallization, nuclear magnetic resonance or photoaffinity labeling (Smith et al. (1992) *J. Mol. Biol*. 224:899-904; de Vos et al. (1992) *Science* 255:306-312).

Substantial homology can be to the entire nucleic acid or amino acid sequence or to fragments of these sequences. The invention thus also includes polypeptide fragments of CaR2. Fragments can be derived from the amino acid sequence shown in SEQ ID NO-2. However, the invention also encompasses fragments of the variants of CaR2 as described herein.

Accordingly, a fragment can comprise at least about 10, 15, 20, 25, 30, 35, 40, 45, 50, 100, 200, 300, 400, 500, 600, 700, 800, 900 or more contiguous amino acids. Fragments can retain one or more of the biological activities of the protein.

The fragments to which the invention pertains, however, are not to be construed as encompassing fragments that may be disclosed prior to the present invention.

Fragments can also be used as an immunogen to generate CaR2 antibodies. Preferred antigenic regions of CaR2 protein are set forth, for example, in FIG. 6.

Biologically active fragments (peptides which are, for example, 5, 7, 10, 12, 15, 20, 30, 35, 36, 37, 38, 39, 40, 50, 100, 200, 250, 300, 350, 400, 450, 500, 550, 600, 650, 700, 750, 800, 850, 900 or more amino acids in length) can comprise a domain or motif, e.g., a catalytic site, calcium binding domain, OC binding domain, G-protein binding domain, transmembrane domain, extracellular domain, or the extracellular loops.

Such domains or motifs can be identified by means of routine computerized homology searching procedures.

Accordingly useful fragments of CaR2, for example, can extend in one or both directions from the functional sites or regions of the protein described herein to encompass 5, 10, 15, 20, 30, 40, 50, or up to 100 amino acids. Further, fragments can include sub-fragments of the specific domains mentioned above, which sub-fragments retain the function of the domain from which they are derived.

Figure 6:
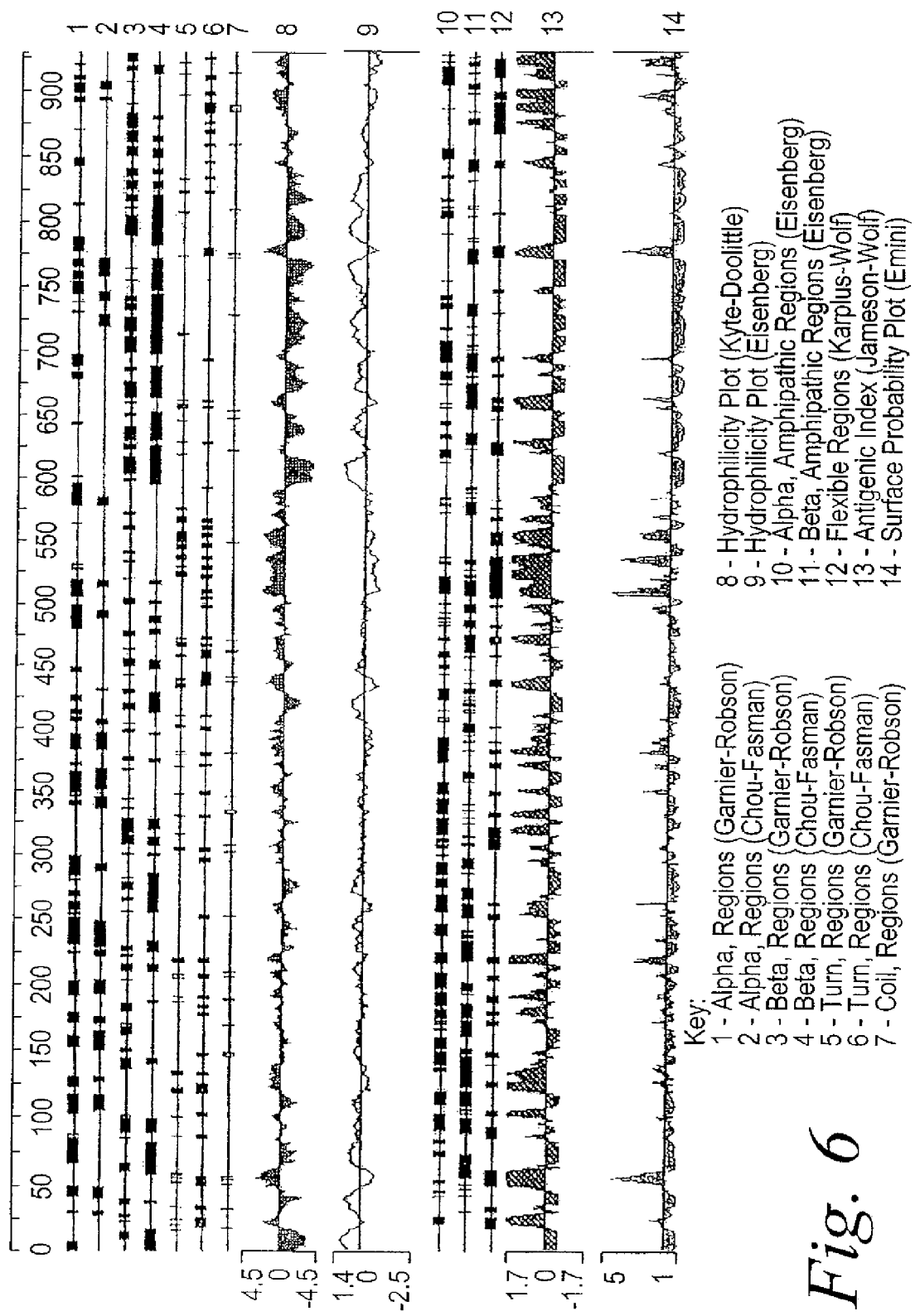
FIG. 6 shows a structural, hydrophobicity, hydrophilicity, amphipathic region, antigenic index, and surface probability prediction for SEQ ID NO:2.

The invention also provides fragments with immunogenic properties. These contain an epitope-bearing portion of CaR2 and variants. These epitope-bearing peptides are useful to raise antibodies that bind specifically to a CaR2 polypeptide or region or fragment. These peptides can contain at least 10, 12, at least 14, or between at least about 15 to about 30 amino acids, and can be generated, for example, using the antigenic index profile of CaR2 (FIG. 6).

Non-limiting examples of antigenic polypeptides that can be used to generate antibodies include but are not limited to peptides derived from an extracellular site. However, intracellularly-made antibodies ("intrabodies") are also encompassed, which would recognize intracellular peptide regions.

The epitope-bearing CaR2 polypeptides can be produced by any conventional means (Houghten, R. A. (1985) *Proc. Natl. Acad Sci. USA* 82.5131-5135). Simultaneous multiple peptide synthesis is described in U.S. Pat. No. 4,631,211.

Fragments can be discrete (not fused to other amino acids or polypeptides) or can be within a larger polypeptide. Further, several fragments can be comprised within a single larger polypeptide. In one embodiment a fragment designed for expression in a host can have heterologous pre- and pro-polypeptide regions fused to the amino terminus of the CaR2 fragment and an additional region fused to the carboxyl terminus of the fragment.

The invention thus provides chimeric or fusion proteins. These comprise a CaR2 peptide sequence operatively linked to a heterologous peptide having an amino acid sequence not substantially homologous to the CaR2. "Operatively linked" indicates that the CaR2 peptide and the heterologous peptide are fused in-frame. The heterologous peptide can be fused to the N-terminus or C-terminus of CaR2 or can be internally located.

In one embodiment the fusion protein does not affect CaR2 function per se. For example, the fusion protein can be a GST-fusion protein in which the CaR2 sequences are fused to the N- or C-terminus of the GST sequences. Other types of fusion proteins include, but are not limited to, enzymatic fusion proteins, for example beta-galactosidase fusions, yeast two-hybrid GAL-4 fusions, poly-His fusions and Ig fusions. Such fusion proteins, particularly poly-His fusions, can facilitate the purification of recombinant CaR2. In certain host cells (e.g., mammalian host cells), expression and/or secretion of a protein can be increased by using a heterologous signal sequence. Therefore, in another embodiment, the fusion protein contains a heterologous signal sequence at its N-terminus.

EP-A-0 464533 discloses fusion proteins comprising various portions of immunoglobulin constant regions. The Fc is useful in therapy and diagnosis and thus results, for example, in improved pharmacokinetic properties (EP-A 0232 262). In drug discovery, for example, human proteins have been fused with Fc portions for the purpose of high-throughput screening assays to identify antagonists (Bennett et al. (1995) J: *Mol. Recog.* 8:52-58 (1995) and Johanson et al. J: *Biol. Chem.* 270:9459-9471). Thus, this invention also utilizes soluble fusion proteins containing a CaR2 polypeptide and various portions of the constant regions of heavy or light chains of immunoglobulins of various subclass (IgG, IgM, IgA, IgB). Preferred as immunoglobulin is the constant part of the heavy chain of human IgG, particularly IgG1, where fusion takes place at the hinge region. For some uses it is desirable to remove the Fc after the fusion protein has been used for its intended purpose, for example when the fusion protein is to be used as antigen for immunizations. In a particular embodiment, the Fc part can be removed in a simple way by a cleavage sequence, which is also incorporated and can be cleaved with factor Xa.

A chimeric or fusion protein can be produced by standard recombinant DNA techniques. For example, DNA fragments coding for the different protein sequences are ligated together in-frame in accordance with conventional techniques. In another embodiment, the fusion gene can be synthesized by conventional techniques including automated DNA synthesizers. Alternatively, PCR amplification of gene fragments can be carried out using anchor primers which give rise to complementary overhangs between two consecutive gene fragments which can subsequently be annealed and re-amplified to generate a chimeric gene sequence (see Ausubel et al. (1992) *Current Protocols in Molecular Biology*). Moreover, many expression vectors are commercially available that already encode a fusion moiety (e.g., a GST protein). A CaR2-encoding nucleic acid can be cloned into such an expression vector such that the fusion moiety is linked in-frame to CaR2.

Another form of fusion protein is one that directly affects CaR2 functions. Accordingly, a CaR2 polypeptide is encompassed by the present invention in which one or more of the CaR2 domains (or parts thereof) has been replaced by homologous domains (or parts thereof) from another calcium receptor family member. Accordingly, various permutations are possible. For example, the aminoterminal domain, or subregion thereof, can be replaced with the domain or subregion from another isoform or calcium receptor family. As a further example, the catalytic domain or parts thereof, can be replaced; the carboxyterminal domain or subregion can be replaced. Thus, chimeric CaR2s can be formed in which one or more of the native domains or subregions has been replaced by another.

Additionally, chimeric CaR2 proteins can be produced in which one or more functional sites is derived from a different isoform, or from another calcium receptor family. It is understood, however, that sites could be derived from calcium receptor families that occur in the mammalian genome but which have not yet been discovered or characterized.

The isolated CaR2 can be purified from cells that naturally express it, purified from cells that naturally express it but have been modified to overproduce CaR2, e.g., purified from cells that have been altered to express it (recombinant), synthesized using known protein synthesis methods, or by modifying cells that naturally encode CaR2 to express it.

In one embodiment, the protein is produced by recombinant DNA techniques For example, a nucleic acid molecule encoding the CaR2 polypeptide is cloned into an expression vector, the expression vector introduced into a host cell and the protein expressed in the host cell. The protein can then be isolated from the cells by an appropriate purification scheme using standard protein purification techniques.

In other embodiments, the recombinant cell has been manipulated to activate expression of the endogenous CaR2 gene. For example, WO 99/15650, WO 00/49162, U.S. Pat. No. 6,361,972 and U.S. Pat. No. 6,410,266 describe a method of expressing endogenous genes termed, random activation of gene expression (RAGE), that can be used to activate or increase expression of endogenous CaR2. The RAGE methodology involves non-homologous recombination of a regulatory sequence to activate expression of a downstream endogenous gene. Alternatively, WO 94//12650, WO 95/31560, WO 96/129411, U.S. Pat. No. 5,733,761 and U.S. Pat. No. 6,270,985 describe a method of increasing expression of an endogenous gene that involves homologous recombination of a DNA construct that includes a targeting sequence, a regulatory sequence, an exon, and a splice-donor site. Upon homologous recombination a downstream endogenous gene is expressed. The methods of expressing endogenous genes described in the forgoing patents are hereby expressly incorporated by reference.

Polypeptides often contain amino acids other than the 20 amino acids commonly referred to as the 20 naturally-occurring amino acids. Further, many amino acids, including the terminal amino acids, may be modified by natural processes, such as processing and other post-translational modifications, or by chemical modification techniques well known in the art. Common modifications that occur naturally in polypeptides are described in basic texts, detailed monographs, and the research literature, and they are well known to those of skill in the art.

Accordingly, the polypeptides also encompass derivatives or analogs in which a substituted amino acid residue is not one encoded by the genetic code, in which a substituent group is included, in which the mature polypeptide is fused with another compound, such as a compound to increase the half-life of the polypeptide (for example, polyethylene glycol), or in which the additional amino acids are fused to the mature polypeptide, such as a leader or secretory sequence or a sequence for purification of the mature polypeptide or a pro-protein sequence.

Known modifications include, but are not limited to, acetylation, acylation, ADP-ribosylation, amidation, covalent attachment of flavin, covalent attachment of a heme moiety, covalent attachment of a nucleotide or nucleotide derivative, covalent attachment of a lipid or lipid derivative, covalent attachment of phosphatidylinositol, cross-linking, cyclization, disulfide bond formation, demethylation, formation of covalent crosslinks, formation of cystine, formation of pyroglutamate, formylation, gamma carboxylation, glycosylation, GPI anchor formation, hydroxylation, iodination, methylation, myristoylation, oxidation, proteolytic processing, phosphorylation, prenylation, racemization, selenoylation, sulfation, transfer-RNA mediated addition of amino acids to proteins such as arginylation, and ubiquitination.

Such modifications are well-known to those of skill in the art and have been described in great detail in the scientific literature. Several particularly common modifications, glycosylation, lipid attachment, sulfation, gamma-carboxylation of glutamic acid residues, hydroxylation and ADP-ribosylation, for instance, are described in most basic texts, such as *Proteins—Structure and Molecular Properties*, 2nd ed., T. E. Creighton, W. H. Freeman and Company, New York (1993). Many detailed reviews are available on this subject, such as by Wold, F., *Posttranslational Covalent Modification of Proteins*, B. C. Johnson, Ed., Academic Press, New York 1-12 (1983); Seifter et al (1990) *Meth. Enzymol.* 182: 626-646) and Rattan et al. (1992) *Ann. NY: Acad. Sci.* 663:48-62).

As is also well known, polypeptides are not always entirely linear. For instance, polypeptides may be branched as a result of ubiquitination, and they may be circular, with or without branching, generally as a result of post-translation events, including natural processing events and events brought about by human manipulation which do not occur naturally. Circular, branched and branched circular polypeptides may be synthesized by non-translational natural processes and by synthetic methods.

Modifications can occur anywhere in a polypeptide, including the peptide backbone, the amino acid side-chains and the amino or carboxyl termini. Blockage of the amino or carboxyl group in a polypeptide, or both, by a covalent modification, is common in naturally-occurring and synthetic polypeptides. For instance, the aminoterminal residue of polypeptides made in *E. coli*, prior to proteolytic processing, almost invariably will be N-formylmethionine.

The modifications can be a function of how the protein is made. For recombinant polypeptides, for example, the modifications will be determined by the host cell posttranslational modification capacity and the modification signals in the polypeptide amino acid sequence. Accordingly, when glycosylation is desired, a polypeptide should be expressed in a glycosylating host, generally a eukaryotic cell. Insect cells often carry out the same posttranslational glycosylations as mammalian cells, and, for this reason, insect cell expression systems have been developed to efficiently express mammalian proteins having native patterns of glycosylation. Similar considerations apply to other modifications. The same type of modification may be present in the same or varying degree at several sites in a given polypeptide. Also, a given polypeptide may contain more than one type of modification.

B. CaR2 Antibodies

The methods for using antibodies described herein are based on the generation of antibodies that specifically bind to CaR2 or its variants or fragments.

To generate antibodies, an isolated CaR2 polypeptide is used as an immunogen to generate antibodies using standard techniques for polyclonal and monoclonal antibody preparation. Either the full-length protein, or one or more antigenic peptide fragments can be used.

Antibodies are preferably prepared from various regions of CaR2 described herein, or from discrete fragments in these regions. However, antibodies can be prepared from any region of the peptide as described herein. A preferred fragment produces an antibody that diminishes or completely prevents binding of, for example, Ca++ or OC Antibodies can be developed against the entire CaR2 or domains of CaR2 as described herein. Antibodies can also be developed against specific functional sites as disclosed herein.

Antibody Uses

The antibodies can be used to isolate a CaR2 by standard techniques, such as affinity chromatography or immunoprecipitation. The antibodies can facilitate the purification of the natural CaR2 from cells and recombinantly produced CaR2 expressed in host cells.

The antibodies are useful to detect the presence of CaR2 in cells or tissues to determine the pattern of expression of the CaR2 among various tissues in an organism and over the course of normal development.

The antibodies can be used to detect CaR2 in situ, in vitro, or in a cell lysate or supernatant in order to evaluate the abundance and pattern of expression.

The antibodies can be used to assess abnormal tissue distribution or abnormal expression during development.

The antigenic peptide can comprise a contiguous sequence of at least 8, 9, 10, 12, 14, 15, or 30 amino acid residues. In one embodiment, fragments correspond to regions that are located on the surface of the protein, e.g., hydrophilic regions (see FIG. 6). These fragments are not to be construed, however, as encompassing any fragments, which may be disclosed prior to the invention.

"Antibody" includes immunoglobulin molecules and immunologically active determinants of immunoglobulin molecules, i.e., molecules that contain an antigen binding site which specifically binds (immunoreacts with) an antigen. Structurally, the simplest naturally occurring antibody (e.g., IgG) comprises four polypeptide to chains, two copies of a heavy (H) chain and two of a light (L) chain, all covalently linked by disulfide bonds. Specificity of binding in the large and diverse set of antibodies is found in the variable (V) determinant of the H and L chains; regions of the molecules that are primarily structural are constant (C) in this set. Antibody includes polyclonal antibodies, monoclonal antibodies, whole immunoglobulins, and antigen binding fragments of the immunoglobulins.

The binding sites of the proteins that comprise an antibody, i.e., the antigen-binding functions of the antibody, are localized by analysis of fragments of a naturally-occurring antibody. Thus, antigen-binding fragments are also intended to be designated by the term "antibody." Examples of binding fragments encompassed within the term antibody include: a Fab fragment consisting of the $V_L$, $V_H$, $C_L$ and $C_{H1}$ domains; an $F_d$ fragment consisting of the $V_H$ and $C_{H1}$ domains; an $F_v$ fragment consisting of the $V_L$ and $V_H$ domains of a single arm of an antibody; a dAb fragment (Ward et al., 1989 Nature 341: 544-546) consisting of a $V_H$ domain; an isolated complementarity determining region (CDR); and an $F(ab')_2$ fragment, a bivalent fragment comprising two Fab' fragments linked by a disulfide bridge at the hinge region. These antibody fragments are obtained using conventional techniques well-known to those with skill in the art, and the fragments are screened for utility in the same manner as are intact antibodies. The term "antibody" is further intended to include bispecific and chimeric molecules having at least one antigen binding determinant derived from an antibody molecule.

In the diagnostic and prognostic assays of the invention, the antibody can be a polyclonal antibody or a monoclonal antibody and in a preferred embodiment is a labeled antibody.

Polyclonal antibodies are produced by immunizing animals, usually a mammal, by multiple subcutaneous or intraperitoneal injections of an immunogen (antigen) and an adjuvant as appropriate. As an illustrative embodiment, animals are typically immunized against a protein, peptide or derivative by combining about 1 µg to 1 mg of protein capable of eliciting an immune response, along with an enhancing carrier preparation, such as Freund's complete adjuvant, or an aggregating agent such as alum, and injecting the composition intradermally at multiple sites. Animals are later boosted with at least one subsequent administration of a lower amount, as ⅕ to ⅒ the original amount of immunogen in Freund's complete adjuvant (or other suitable adjuvant) by subcutaneous injection at multiple sites. Animals are subsequently bled, serum assayed to determine the specific antibody titer, and the animals are again boosted and assayed until the titer of antibody no longer increases (i.e., plateaus).

Such populations of antibody molecules are referred to as "polyclonal" because the population comprises a large set of antibodies each of which is specific for one of the many differing epitopes found in the immunogen, and each of which is characterized by a specific affinity for that epitope. An epitope is the smallest determinant of antigenicity, which for a protein, comprises a peptide of six to eight residues in length (Berzofsky, J. and I. Berkower, (1993) in Paul, W., Ed., Fundamental Immunology, Raven Press, N.Y., p. 246). Affinities range from low, e.g. $10^{-6}$ M, to high, e.g., $10^{-11}$ M. The polygonal antibody fraction collected from mammalian serum is isolated by well known techniques, e.g. by chromatography with an affinity matrix that selectively binds immunoglobulin molecules such as protein A, to obtain the IgG fraction. To enhance the purity and specificity of the antibody, the specific antibodies may be further purified by immunoaffinity chromatography using solid phase-affixed immunogen. The antibody is contacted with the solid phase-affixed immunogen for a period of time sufficient for the immunogen to immunoreact with the antibody molecules to form a solid phase-affixed immunocomplex. Bound antibodies are eluted from the solid phase by standard techniques, such as by use of buffers of decreasing pH or increasing ionic strength, the eluted fractions are assayed, and those containing the specific antibodies are combined.

"Monoclonal antibody" or "monoclonal antibody composition" as used herein refers to a preparation of antibody molecules of single molecular composition. A monoclonal antibody composition displays a single binding specificity and affinity for a particular epitope. Monoclonal antibodies can be prepared using a technique which provides for the production of antibody molecules by continuous growth of cells in culture. These include but are not limited to the hybridoma technique originally described by Kohler and Milstein (1975, Nature 256:495-497; see also Brown et al. 1981 J. Immunol 127:539-46; Brown et al., 1980, J Biol Chem 255:4980-83; Yeh et al. 1976, PNAS 76:2927-31; and Yeh et al., 1982, Int. J. Cancer 29:269-75) and the more recent human B cell hybridoma technique (Kozbor et al., 1983, Immunol Today 4:72), EBV-hybridoma technique (Cole et al., 1985, Monoclonal Antibodies and Cancer Therapy, Alan R. Liss, Inc., pp. 77-96), and trioma techniques. The technology for producing hybridomas is well known (see generally Current Protocols in Immunology, Coligan et al. ed., John Wiley & Sons, New York, 1994). Hybridoma cells producing a monoclonal antibody of the invention are detected by screening the hybridoma culture supernatants for antibodies that bind the polypeptide of interest, e.g., using a standard ELISA assay.

A monoclonal antibody can be produced by the following steps. In all procedures, an animal is immunized with an antigen such as a protein (or peptide thereof) as described above for preparation of a polyclonal antibody. The immunization is typically accomplished by administering the immunogen to an immunologically competent mammal in an immunologically effective amount, i.e., an amount sufficient to produce an immune response. Preferably, the mammal is a rodent such as a rabbit, rat or mouse. The mammal is then maintained on a booster schedule for a time period sufficient for the mammal to generate high affinity antibody molecules as described. A suspension of antibody-producing cells is removed from each immunized mammal secreting the desired antibody. After a sufficient time to generate high affinity antibodies, the animal (e.g., mouse) is sacrificed and antibody-producing lymphocytes are obtained from one or more of the lymph nodes, spleens and peripheral blood. Spleen cells are preferred, and can be mechanically separated into individual cells in a physiological medium using methods well known to one of skill in the art. The antibody-producing cells are immortalized by fusion to cells of a mouse myeloma line. Mouse lymphocytes give a high percentage of stable fusions with mouse homologous myelomas, however rat, rabbit and frog somatic cells can also be used. Spleen cells of the desired antibody-producing animals are immortalized by fusing with myeloma cells, generally in the presence of a fusing agent such as polyethylene glycol. Any of a number of myeloma cell lines suitable as a fusion partner are used with to standard techniques, for example, the P3-NS1/1-Ag4-1, P3-x63-Ag8.653 or Sp2/O-Ag14 myeloma lines, available from the American Type Culture Collection (ATCC), Rockville, Md.

The fusion-product cells, which include the desired hybridomas, are cultured in selective medium such as HAT medium, designed to eliminate unfused parental myeloma or lymphocyte or spleen cells. Hybridoma cells are selected and are grown under limiting dilution conditions to obtain isolated clones. The supernatants of each clonal hybridoma is screened for production of antibody of desired specificity and affinity, e.g., by immunoassay techniques to determine the desired antigen such as that used for immunization. Monoclonal antibody is isolated from cultures of producing cells by conventional methods, such as ammonium sulfate precipitation, ion exchange chromatography, and affinity chromatography (Zola et al., Monoclonal Hybridoma Antibodies: Techniques And Applications, Hurell (ed.), pp. 51-52, CRC Press, 1982). Hybridomas produced according to these methods can be propagated in culture in vitro or in vivo (in ascites fluid) using techniques well known to those with skill in the art.

Alternative to preparing monoclonal antibody-secreting hybridomas, a monoclonal antibody directed against a polypeptide of the invention can be identified and isolated by screening a recombinant combinatorial immunoglobulin library (e.g., an antibody phage display library) with the polypeptide of interest. Kits for generating and screening phage display libraries are commercially available (e.g., the Pharmacia Recombinant Phage Antibody System, Catalog No. 27-9400-01; and the Stratagene SurfZAP Phage Display Kit, Catalog No. 240612). Additionally, examples of methods and reagents particularly amenable for use in generating and screening an antibody display library can be found in, for example, U.S. Pat. No. 5,223,409; PCT Publication No. WO 92/18619; PCT Publication No. WO 91/17271; PCT Publication No. WO 92/20791; PCT Publication No. WO 92/15679; PCT Publication No. WO 93/01288; PCT Publication No. WO 92/01047; PCT Publication No. WO 92/09690; PCT Publication No. WO 90/02809; Fuchs et. al. (1991) Bio/Technology 9:1370-1372; Hay et al. (1992) Hum. Antibod. Hybridomas 3:81-85; Huse et al. (1989) Science 246:1275-1281; Griffiths et al. (1993) EMBO J. 12:725-734.

Additionally, recombinant antibodies, such as chimeric and humanized monoclonal antibodies, comprising both human and non-human portions, which can be made using standard recombinant DNA techniques, are within the scope of the invention. Such chimeric and humanized monoclonal antibodies can be produced by recombinant DNA techniques known in the art, for example using methods described in PCT Publication No. WO 87/02671; European Patent Application 184,187; European Patent Application 171,496; European Patent Application 173,494; PCT Publication No. WO 86/01533; U.S. Pat. No. 4,816,567; European Patent Application 125,023; Better et al. (1988) Science 240:1041-1043; Liu et al. (1987) Proc. Natl. Acad. Sci. USA 84:3439-3443; Liu et al. (1987) J. Immunol. 139:3521-3526; Sun et al. (1987) Proc. Natl. Acad. Sci. USA 84:214-218; Nishimura et al. (1987) Cancer Res. 47:999-1005; Wood et al. (1985) Nature 314:446-449; and Shaw et al. (1988) J. Natl. Cancer Inst. 80:1553-1559); Morrison (1985) Science 229:1202-1207; Oi et al. (1986) Bio/Techniques 4:214; U.S. Pat. No. 5,225,539; Jones et al. (1986) Nature 321:552-525; Verhoeyan et al. (1988) Science 239:1534; and Beidler et al. (1988) J. Immunol. 141:4053-4060.

Fully human antibodies can also be generated using transgenic mice in which the endogenous immunoglobulin genes have been inactivated and replaced with genes encoding the human light and heavy chain immunoglobulins. Such mice, and methods for using these mice to generate human polyclonal and monoclonal antibodies to an antigen are described for example in U.S. Pat. Nos. 6,075,181, 6,091,001 and 6,300,129, and in Tomizuka et al. (2000) Proc. Natl. Acad. Sci. 97:722-727.

Human antibodies are particularly desirable for therapeutic treatment of human patients. For an overview of this technology for producing human antibodies, see Lonberg et al. (1995) Int. Rev. Immunol. 13:65-93. For a detailed discussion of this technology for producing human antibodies and human monoclonal antibodies and protocols for producing such antibodies, e.g., U.S. Pat. No. 5,625,126; U.S. Pat. No. 5,633,425; U.S. Pat. No. 5,569,825; U.S. Pat. No. 5,661,016; and U.S. Pat. No. 5,545,806.

The invention also encompasses kits for using antibodies to detect the presence of a CaR2 protein in a biological sample. The kit can comprise antibodies such as a labeled or labelable antibody and a compound or agent for detecting phosphodiesterase in a biological sample; means for determining the amount of CaR2 in the sample; and means for comparing the amount of CaR2 in the sample with a standard. The compound or agent can be packaged in a suitable container. The kit can further comprise instructions for using the kit to detect CaR2.

"Labeled antibody" as used herein includes antibodies that are labeled by a detectable means and includes enzymatically, radioactively, fluorescently, chemiluminescently, and/or bioluminescently labeled antibodies.

One of the ways in which an antibody can be detectably labeled is by linking the same to an enzyme. This enzyme, in turn, when later exposed to its substrate, will react with the substrate in such a manner as to produce a chemical moiety which can be detected, for example, by spectrophotometric, fluorometric or by visual means-Enzymes which can be used to detectably label the CaR2 specific antibody include, but are not limited to, malate dehydrogenase, staphylococcal nuclease, delta-V-steroid isomerase, yeast alcohol dehydrogenase, alpha-glycerophosphate dehydrogenase, triose phosphate isomerase, horseradish peroxidase, alkaline phosphatase, asparaginase, glucose oxidase, beta-galactosidase, ribonuclease, urease, catalase, glucose-VI-phosphate dehydrogenase, glucoamylase and acetylcholinesterase.

Detection may be accomplished using any of a variety of immunoassays. For example, by radioactively labeling an antibody, it is possible to detect the antibody through the use of radioimmune assays. A description of a radioimmune assay (RIA) may be found in Laboratory Techniques and Biochemistry in Molecular Biology, by Work, T. S., et al., North Holland Publishing Company, NY (1978), with particular reference to the chapter entitled "An Introduction to Radioimmune Assay and Related Techniques" by Chard, T.

The radioactive isotope can be detected by such means as the use of a gamma counter or a scintillation counter or by audioradiography. Isotopes which are particularly useful for the purpose of the present invention are: $^{3}H$, $^{131}I$, $^{35}S$, $^{14}C$, and preferably $^{125}I$.

It is also possible to label an antibody with a fluorescent compound. When the fluorescently labeled antibody is exposed to light of the proper wave length, its presence can then be detected due to fluorescence. Among the most commonly used fluorescent labeling compounds are fluorescein isothiocyanate, rhodamine, phycoerytherin, phycocyanin, allophycocyanin, o-phthaldehyde and fluorescamine.

An antibody can also be detectably labeled using fluorescence emitting metals such as $^{152}$Eu, or others of the lanthanide series. These metals can be attached to the antibody using such metal chelating groups as diethylenetriaminepentaacetic acid (DTPA) or ethylenediaminetetraacetic acid (EDTA).

An antibody also can be detectably labeled by coupling it to a chemiluminescent compound. The presence of the chemiluminescent-tagged antibody is then determined by detecting the presence of luminescence that arises during the course of a chemical reaction. Examples of particularly useful chemiluminescent labeling compounds are luminol, luciferin, isoluminol, theromatic acridinium ester, imidazole, acridinium salt and oxalate ester.

Likewise, a bioluminescent compound may be used to label an antibody of the present invention. Bioluminescence is a type of chemiluminescence found in biological systems in which a catalytic protein increases the efficiency of the chemiluminescent reaction. The presence of a bioluminescent protein is determined by detecting the presence of luminescence. Important bioluminescent compounds for purposes of labeling are luciferin, luciferase and aequorin.

In the diagnostic and prognostic assays of the invention, the amount of binding of the antibody to the biological sample can be determined by the intensity of the signal emitted by the labeled antibody and/or by the number cells in the biological sample bound to the labeled antibody.

Antibodies directed toward a protein of interest can also be connected to magnetic beads and used to enrich a cell population. Immunomagnetic selection has been used previously for this purpose and examples of this method can be found, for example, at U.S. Pat. No. 5,646,001; Ree et al (2002) *Int. J. Cancer* 97:28-33; Molnar et al. (2001) *Clin. Cancer Research* 7:4080-4085; and Kasimir-Bauer et al. (2001) *Breast Cancer Res. Treat.* 69:123-32. An antibody, either polyclonal or monoclonal, that is specific for a cell surface protein on a cell of interest is attached to a magnetic substrate thereby allowing selection of only those cells that express the surface protein of interest. Once a population of cells is selected, the following assays, can be performed to test for the presence of CaR2.

Antibodies of the present invention can be used as for therapeutic administration. Antibodies can be administered to a subject alone or in combination with one or more other substances, i.e., in a pharmaceutical composition.

C. CaR2 Nucleic Acids

The invention further provides methods and uses for the nucleotide sequence in SEQ ID NO:1. The specifically disclosed cDNA comprises the coding region and 5' and 3' untranslated sequences in SEQ ID NO:1. The expression vector comprising the nucleotide sequence of SEQ ID NO:1 has been deposited with the ATCC and given deposit number: ATCC_____.

The deposits will be maintained under the terms of the Budapest Treaty on the International Recognition of the Deposit of Microorganisms. The deposits are provided as a convenience to those of skill in the art and is not an admission that a deposit is required under 35 U.S.C. §112. The deposited sequence, as well as the polypeptides encoded by the sequence, are incorporated herein by reference and controls in the event of conflict, such as a sequencing error, with description in this invention.

The invention provides isolated polynucleotides encoding CaR2. The term "CaR2 polynucleotide" or "CaR2 nucleic acid" refers to the sequences shown in SEQ ID NO:1. The term "CaR2 polynucleotide" or "CaR2 nucleic acid" further includes variants and fragments of the CaR2 polynucleotides.

An "isolated" CaR2 nucleic acid is one that is separated from other nucleic acid present in the natural source of the CaR2 nucleic acid. Preferably, an "isolated" nucleic acid is free of sequences which naturally flank the CaR2 nucleic acid (i.e., sequences located at the 5' and 3' ends of the nucleic acid) in the genomic DNA of the organism from which the nucleic acid is derived. However, there can be some flanking nucleotide sequences, for example up to about 5KB. The important point is that the CaR2 nucleic acid is isolated from flanking sequences such that it can be subjected to the specific manipulations described herein, such as recombinant expression, preparation of probes and primers, and other uses specific to the CaR2 nucleic acid sequences.

Moreover, an "isolated" nucleic acid molecule, such as a cDNA or RNA molecule, can be substantially free of other cellular material, or culture medium when produced by recombinant techniques, or chemical precursors or other chemicals when chemically synthesized. However, the nucleic acid molecule can be fused to other coding or regulatory sequences and still be considered isolated.

In some instances, the isolated material will form part of a composition (for example, a crude extract containing other substances), buffer system or reagent mix. In other circumstances, the material may be purified to essential homogeneity, for example as determined by PAGE or column chromatography such as HPLC. Preferably, an isolated nucleic acid comprises at least about 50, 80 or 90% (on a molar basis) of all macromolecular species present.

For example, recombinant DNA molecules contained in a vector are considered isolated. Further examples of isolated DNA molecules include recombinant DNA molecules maintained in heterologous host cells or purified (partially or substantially) DNA molecules in solution. Isolated RNA molecules include in vivo or in vitro RNA transcripts of the isolated DNA molecules of the present invention. Isolated nucleic acid molecules according to the present invention further include such molecules produced synthetically.

In some instances, the isolated material will form part of a composition (for example, a crude extract containing other substances), buffer system or reagent mix. In other circumstances, the material may be purified to essential homogeneity, for example as determined by PAGE or column chromatography such as HPLC. Preferably, an isolated nucleic acid comprises at least about 50, 80 or 90% (on a molar basis) of all macromolecular species present.

The CaR2 polynucleotides can encode the mature protein plus additional amino or carboxyterminal amino acids, or amino acids interior to the mature polypeptide (when the mature form has more than one polypeptide chain, for instance). Such sequences may play a role in processing of a protein from precursor to a mature form, facilitate protein trafficking, prolong or shorten protein half-life or facilitate manipulation of a protein for assay or production, among other things. As generally is the case in situ, the additional amino acids may be processed away from the mature protein by cellular enzymes.

The CaR2 polynucleotides include, but are not limited to, the sequence encoding the mature polypeptide alone, the sequence encoding the mature polypeptide and additional coding sequences, such as a leader or secretory sequence (e.g., a pre-pro or pro-protein sequence), the sequence encoding the mature polypeptide, with or without the additional coding sequences, plus additional non-coding sequences, for example introns and non-coding 5' and 3' sequences such as transcribed but non-translated sequences that play a role in transcription, mRNA processing (including splicing and polyadenylation signals), ribosome binding and stability of mRNA. In addition, the polynucleotide may be fused to a marker sequence encoding, for example, a peptide that facilitates purification.

CaR2 polynucleotides can be in the form of RNA, such as mRNA, or in the form DNA, including cDNA and genomic DNA obtained by cloning or produced by chemical synthetic techniques or by a combination thereof. The nucleic acid, especially DNA, can be double-stranded or single-stranded. Single-stranded nucleic acid can be the coding strand (sense strand) or the non-coding strand (anti-sense strand).

In one embodiment, the CaR2 nucleic acid comprises only the coding region.

The invention further provides variant CaR2 polynucleotides, and fragments thereof, that differ from the nucleotide sequence shown in SEQ ID NO:1 due to degeneracy of the genetic code and thus encode the same protein as that encoded by the nucleotide sequence shown in SEQ ID NO:1.

The invention also provides CaR2 nucleic acid molecules encoding the variant polypeptides described herein. Such polynucleotides may be naturally occurring, such as allelic variants (same locus), homologs (different locus), and orthologs (different organism), or may be constructed by recombinant DNA methods or by chemical synthesis. Such non-naturally occurring variants may be made by mutagenesis techniques, including those applied to polynucleotides, cells, or organisms. Accordingly, as discussed above, the variants can contain nucleotide substitutions, deletions, inversions and insertions.

Typically, variants have a substantial identity with a nucleic acid molecule of SEQ ID NO:1, and the complements thereof. Variation can occur in either or both the coding and non-coding regions. The variations can produce both conservative and non-conservative amino acid substitutions.

Orthologs, homologs, and allelic variants can be identified using methods well known in the art. These variants comprise a nucleotide sequence encoding a CaR2 that is at least about 60-65%, 65-70%, typically at least about 70-75%, more typically at least about 80-85%, and most typically at least about 90-95%, 96%, 97%, 98%, 99% or more homologous to the nucleotide sequence shown in SEQ ID NO:1 or a fragment of this sequence. Such nucleic acid molecules can readily be identified as being able to hybridize, under stringent conditions, to the nucleotide sequence shown in SEQ ID NO:1 or a fragment of the sequence. It is understood that stringent hybridization does not indicate substantial homology where it is due to general homology, such as poly A sequences, or sequences common to all or most proteins, or all cyclic nucleotide CaR2.

As used herein, the term "hybridizes under stringent conditions" is intended to describe conditions for hybridization and washing under which nucleotide sequences encoding a polypeptide at least about 60-65% homologous to each other typically remain hybridized to each other. The conditions can be such that sequences at least about 65%, at least about 70%, at least about 75%, at least about 80%, at least about 90%, at least about 95%, 96%, 97%, 98%, 99% or more identical to each other remain hybridized to one another. Such stringent conditions are known to those skilled in the art and can be found in *Current Protocols in Molecular Biology*, John Wiley & Sons, N.Y. (1989), 6.3.1-6.3.6, incorporated by reference. One example of stringent hybridization conditions are hybridization in 6× sodium chloride/sodium citrate (SSC) at about 45° C., followed by one or more washes in 0.2×SSC, 0.1% SDS at 50°, 55°, 60°, 62° or 65° C. In another non-limiting example, nucleic acid molecules are allowed to hybridize in 6× sodium chloride/sodium citrate (SSC) at about 45° C., followed by one or more low stringency washes in 0.2×SSC/0.1% SDS at room temperature, or by one or more moderate stringency washes in 0.2×SSC/0.1% SDS at 42° C., or washed in 0.2×SSC/0.1% SDS at 65° C. for high stringency. In one embodiment, an isolated nucleic acid molecule that hybridizes under stringent conditions to the sequence of SEQ ID NO:1.

As used herein, a "naturally-occurring" nucleic acid molecule refers to an RNA or DNA molecule having a nucleotide sequence that occurs in nature (e.g., encodes a natural protein).

As understood by those of ordinary skill, the exact conditions can be determined empirically and depend on ionic strength, temperature and the concentration of destabilizing agents such as formamide or denaturing agents such as SDS. Other factors considered in determining the desired hybridization conditions include the length of the nucleic acid sequences, base composition, percent mismatch between the hybridizing sequences and the frequency of occurrence of subsets of the sequences within other non-identical sequences. Thus, equivalent conditions can be determined by varying one or more of these parameters while maintaining a similar degree of identity or similarity between the two nucleic acid molecules.

The present invention also provides isolated nucleic acids that contain a single or double stranded fragment or portion that hybridizes under stringent conditions to the nucleotide sequence of SEQ ID NO:1 or the complement of SEQ ID NO:1. In one embodiment, the nucleic acid consists of a portion of the nucleotide sequence of SEQ ID NO 2 and the complement of SEQ ID NO:1. The nucleic acid fragments of the invention are at least about 15, preferably at least about 18, 20, 23 or 25 nucleotides, and can be 50, 100, 150, 200, 300, 400, 500, 600, 700, 800, 900, 1000, 1500, 2000, 2500, 2600, 2700, 2800, or 2900 or more nucleotides in length. Longer fragments, for example, 1000 or more nucleotides in length, which encode antigenic proteins or polypeptides described herein are useful.

Furthermore, the invention provides polynucleotides that comprise a fragment of the full-length CaR2 polynucleotide. The fragment can be single or double-stranded and can comprise DNA or RNA The fragment can be derived from either the coding or the non-coding sequence.

In another embodiment an isolated CaR2 nucleic acid encodes the entire coding region. In another embodiment the isolated CaR2 nucleic acid encodes a sequence corresponding to the mature protein. Other fragments include nucleotide sequences encoding the amino acid fragments described herein.

Thus, CaR2 nucleic acid fragments further include sequences corresponding to the domains described herein, subregions also described, and specific functional sites. CaR2 nucleic acid fragments also include combinations of the domains, segments, and other functional sites described above. A person of ordinary skill in the art would be aware of the many permutations that are possible.

Where the location of the domains or sites have been predicted by computer analysis, one of ordinary skill would appreciate that the amino acid residues constituting these domains can vary depending on the criteria used to define the domains.

However, it is understood that a CaR2 fragment includes any nucleic acid sequence that does not include the entire gene.

The invention also provides CaR2 nucleic acid fragments that encode epitope bearing regions of the CaR2 proteins described herein.

The nucleic acid fragments useful to practice the invention provide probes or primers in assays, such as those described herein. "Probes" are oligonucleotides that hybridize in a base-specific manner to a complementary strand of nucleic acid. Such probes include polypeptide nucleic acids, as described in Nielsen et al. (1991) *Science* 254: 1497-1500. Typically, a probe comprises a region of nucleotide sequence that hybridizes under highly stringent conditions to at least about 15, typically about 20-25, and more typically about 40, 50, 75 or 100 or more consecutive nucleotides of the nucleic acid sequence shown in SEQ ID NO:1 and the complements thereof. More typically, the probe further comprises a label, e.g., radioisotope, fluorescent compound, enzyme, or enzyme co-factor.

As used herein, the term "primer" refers to a single-stranded oligonucleotide which acts as a point of initiation of template-directed DNA synthesis using well-known methods (e.g., PCR, LCR) including, but not limited to those described herein. The appropriate length of the primer depends on the particular use, but typically ranges from about 15 to 30 nucleotides. The term "primer site" refers to the area of the target DNA to which a primer hybridizes. The term "primer pair" refers to a set of primers including a 5' (upstream) primer that hybridizes with the 5' end of the nucleic acid sequence to be amplified and a 3' (downstream) primer that hybridizes with the complement of the sequence to be amplified.

The CaR2 polynucleotides are thus useful for probes, primers and biological assays.

Where the polynucleotides are used to assess CaR2 properties or functions, such as in the assays described herein, all or less than all of the entire cDNA can be useful. Assays specifically directed to CaR2 functions, such as assessing agonist or antagonist activity, encompass the use of known fragments. Further, diagnostic methods for assessing CaR2 function can also be practiced with any fragment, including those fragments that may have been known prior to the invention. Similarly, in methods involving treatment of CaR2 dysfunction, all fragments are encompassed including those, which may have been known in the art.

The invention utilizes the CaR2 polynucleotides as a hybridization probe for cDNA and genomic DNA to isolate a full-length cDNA and genomic clones encoding variant polypeptides and to isolate cDNA and genomic clones that correspond to variants producing the same polypeptides shown in SEQ ID NO:2 or the other variants described herein. This method is useful for isolating variant genes and cDNA that are expressed in the cells, tissues, and conditions disclosed herein.

The probe can correspond to any sequence along the entire length of the gene encoding CaR2. Accordingly, it could be derived from 5' noncoding regions, the coding region, and 3' noncoding regions.

The nucleic acid probe can be, for example, the full-length cDNA of SEQ ID NO:1, or a fragment thereof such as an oligonucleotide of at least 12, 15, 30, 50, 100, 250 or 500 nucleotides in length and sufficient to specifically hybridize under stringent conditions to mRNA or DNA.

Fragments of the polynucleotides can also be used to synthesize larger fragments or full-length polynucleotides described herein. For example, a fragment can be hybridized to any portion of an mRNA and a larger or full-length cDNA can be produced.

Fragments can also be used to synthesize antisense molecules of desired length and sequence.

Antisense nucleic acids, useful in treatment and diagnosis, can be designed using the nucleotide sequences of SEQ ID NO:1, and constructed using chemical synthesis and enzymatic ligation reactions using procedures known in the art. For example, an antisense nucleic acid (e.g., an antisense oligonucleotide) can be chemically synthesized using naturally occurring nucleotides or variously modified nucleotides designed to increase the biological stability of the molecules or to increase the physical stability of the duplex formed between the antisense and sense nucleic acids, e.g., phosphorothioate derivatives and acridine substituted nucleotides can be used. Examples of modified nucleotides which can be used to generate the antisense nucleic acid include 5-fluorouracil, 5-bromouracil, 5-chlorouracil, 5-iodouracil, hypoxanthine, xanthine, 4-acetylcytosine, 5-(carboxyhydroxylmethyl) uracil, 5-carboxymethylaminomethyl-2-thiouridine, 5-carboxymethylaminomethyl uracil, dihydrouracil, beta-D-galactosylqueosine, inosine, N6-isopentenyladenine, 1-methylguanine, 1-methylinosine, 2,2-dimethylguanine, 2-methyladenine, 2-methylguanine, 3-methylcytosine, 5-methylcytosine, N6-adenine, 7-methylguanine, 5-methyl aminomethyl uracil, 5-methoxyaminomethyl-2-thiouracil, beta-D-mannosylqueosine, 5'-methoxycarboxymethyluracil, 5-methoxyuracil, 2-methylthio-N6-isopentenyladenine, uracil-5-oxyacetic acid (v), wybutoxosine, pseudouracil, queosine, 2-thiocytosine, 5-methyl-2-thiouracil, 2-thiouracil, 4-thiouracil, 5-methyluracil, uracil-5-oxyacetic acid methylester, uracil-5-oxyacetic acid (v), 5-methyl-2-thiouracil, 3-(3-amino-3-N-2-carboxypropyl)uracil, (acp3)w, and 2,6-diaminopurine. Alternatively, the antisense nucleic acid can be produced biologically using an expression vector into which a nucleic acid has been subcloned in an antisense orientation (i.e., RNA transcribed from the inserted nucleic acid will be of an antisense orientation to a target nucleic acid of interest).

Additionally, the nucleic acid molecules useful to practice the invention can be modified at the base moiety, sugar moiety or phosphate backbone to improve, e.g., the stability, hybridization, or solubility of the molecule. For example, the deoxyribose phosphate backbone of the nucleic acids can be modified to generate peptide nucleic acids (see Hyrup et al. (1.996) *Bioorganic & Medicinal Chemistry* 4:5). As used herein, the terms "peptide nucleic acids" or "PNAs" refer to nucleic acid mimics, e.g., DNA mimics, in which the deoxyribose phosphate backbone is replaced by a pseudopeptide backbone and only the four natural nucleobases are retained. The neutral backbone of PNAs has been shown to allow for specific hybridization to DNA and RNA under conditions of low ionic strength. The synthesis of PNA oligomers can be performed using standard solid phase peptide synthesis protocols as described in Hyrup et al. (1996), supra; Perry-O'Keefe et al. (1996) *Proc. Natl. Acad Sci. USA* 93: 14670. PNAs can be further modified, e.g., to enhance their stability, specificity or cellular uptake, by attaching lipophilic or other helper groups to PNA, by the formation of PNA-DNA chimeras, or by the use of liposomes or other techniques of drug delivery known in the art. The synthesis of PNA-DNA chimeras can be performed as described in Hyrup (1996), supra, Finn et al. (1996)

*Nucleic Acids Res.* 24(17):3357-63, Mag et al. (1989) *Nucleic Acids Res.* 17:5973, and Peterser et al. (1975) *Bioorganic Med. Chem. Lett.* 5: 1119.

The nucleic acid molecules and fragments useful to practice the invention can also include other appended groups such as peptides (e.g., for targeting host cell CaR2 in vivo), or agents facilitating transport across the cell membrane (see, e.g., Letsinger et al. (1989) *Proc. Natl. Acad. Sci. USA* 86:6553-6556; Lemaitre et al. (1987) *Proc. Natl. Acad Sci. USA* 84:648-652; PCT Publication No. WO 88/0918) or the blood brain barrier (see, e.g., PCT Publication No. WO 89/10134). In addition, oligonucleotides can be modified with hybridization-triggered cleavage agents (see, e.g., Krol et al. (1988) *Bio-Techniques* 6:958-976) or intercalating agents (see, e.g., Zon (1988) *Pharm Res.* 5:539-549).

D. Vectors and Host Cells

The invention also provides methods using vectors containing the CaR2 polynucleotides. The term "vector" refers to a vehicle, preferably a nucleic acid molecule that can transport the CaR2 polynucleotides. When the vector is a nucleic acid molecule, the CaR2 polynucleotides are covalently linked to the vector nucleic acid. With this aspect of the invention, the vector includes a plasmid, single or double stranded phage, a single or double stranded RNA or DNA viral vector, or artificial chromosome, such as a BAC, PAC, YAC, OR MAC.

A vector can be maintained in the host cell as an extrachromosomal element where it replicates and produces additional copies of the CaR2 polynucleotides. Alternatively, the vector may integrate into the host cell genome to produce additional copies of the CaR2 polynucleotides when the host cell replicates, or to increase or activate expression of the endogenous CaR2 coding sequences.

The invention provides vectors for the maintenance (cloning vectors) or vectors for expression (expression vectors) of the CaR2 polynucleotides. The vectors can function in procaryotic or eukaryotic cells or in both (shuttle vectors).

Expression vectors contain cis-acting regulatory regions that are operably linked in the vector to the CaR2 polynucleotides such that transcription of the polynucleotides is allowed in a host cell. The polynucleotides can be introduced into the host cell with a separate polynucleotide capable of affecting transcription. Thus, the second polynucleotide may provide a trans-acting factor interacting with the cis-regulatory control region to allow transcription of the CaR2 polynucleotides from the vector. Alternatively, a trans-acting factor may be supplied by the host cell. Finally, a trans-acting factor can be produced from the vector itself.

It is understood, however, that in some embodiments, transcription and/or translation of the CaR2 polynucleotides can occur in a cell-free system.

The regulatory sequence to which the polynucleotides described herein can be operably linked include promoters for directing mRNA transcription. These include, but are not limited to, the left promoter from bacteriophage λ, the lac, TRP, and TAC promoters from *E. coli*, the early and late promoters from SV40, the CMV immediate early promoter, the adenovirus early and late promoters, and retrovirus long-terminal repeats.

In addition to control regions that promote transcription, expression vectors may also include regions that modulate transcription, such as repressor binding sites and enhancers. Examples include the SV 40 enhancer, the cytomegalovirus immediate early enhancer, polyoma enhancer, adenovirus enhancers, and retrovirus LTR enhancers.

In addition to containing sites for transcription initiation and control, expression vectors can also contain sequences necessary for transcription termination and, in the transcribed region a ribosome binding site for translation. Other regulatory control elements for expression include initiation and termination codons as well as polyadenylation signals. The person of ordinary skill in the art would be aware of the numerous regulatory sequences that are useful in expression vectors. Such regulatory sequences are described, for example, in Sambrook et al. (1989) *Molecular Cloning: A Laboratory Manual* 2nd ed., Cold Spring Harbor Laboratory Press, Cold Spring Harbor, N.Y.).

A variety of expression vectors can be used to express a CaR2 polynucleotide. Such vectors include chromosomal, episomal, and virus-derived vectors, for example vectors derived from bacterial plasmids, from bacteriophage) from yeast episomes, from yeast chromosomal elements, including yeast artificial chromosomes, from viruses such as baculoviruses, papovaviruses such as SV 40, Vaccinia viruses, adenoviruses, poxviruses, pseudorabies viruses, and retroviruses. Vectors may also be derived from combinations of these sources such as those derived from plasmid and bacteriophage genetic elements, e.g. cosmids and phagemids. Appropriate cloning and expression vectors for prokaryotic and eukaryotic hosts are described in Sambrook et al. (1989) *Molecular Cloning: A Laboratory Manual* 2nd ed., Cold Spring Harbor Laboratory Press, Cold Spring Harbor, N.Y.

The regulatory sequence may provide constitutive expression in one or more host cells (i.e., tissue specific) or may provide for inducible expression in one or more cell types such as by temperature, nutrient additive, or exogenous factor such as a hormone or other ligand. A variety of vectors providing for constitutive and inducible expression in prokaryotic and eukaryotic hosts are well known to those of ordinary skill in the art.

The CaR2 polynucleotides can be inserted into the vector nucleic acid by well-known methodology. Generally, the DNA sequence that will ultimately be expressed is joined to an expression vector by cleaving the DNA sequence and the expression vector with one or more restriction enzymes and then ligating the fragments together. Procedures for restriction enzyme digestion and ligation are well known to those of ordinary skill in the art.

The vector containing the appropriate polynucleotide can be introduced into an appropriate host cell for propagation or expression using well-known techniques. Bacterial cells include, but are not limited to, *E. coli*, *Streptomyces*, and *Salmonella typhimurium*. Eukaryotic cells include, but are not limited to, yeast, insect cells such as *Drosophila*, animal cells such as HT1080, HEK293, COS and CHO cells, and plant cells.

As described herein, it may be desirable to express the polypeptide as a fusion protein. Accordingly, the invention provides fusion vectors that allow for the production of the CaR2 polypeptides. Fusion vectors can increase the expression of a recombinant protein, increase the solubility of the recombinant protein, and aid in the purification of the protein by acting for example as a ligand for affinity purification. A proteolytic cleavage site may be introduced at the junction of the fusion moiety so that the desired polypeptide can ultimately be separated from the fusion moiety. Proteolytic enzymes include, but are not limited to, factor Xa, TEY, thrombin, and enterokinase. Typical fusion expression vectors include pGEX (Smith et al. (1988) *Gene* 67:31-40), pMAL (New England Biolabs, Beverly, Mass.) and pRIT5 (Pharmacia, Piscataway, N.J.) which fuse glutathione S-transferase (GST), maltose E binding protein, or protein A, respectively, to the target recombinant protein. Examples of suitable inducible non-fusion *E. coli* expression vectors include pTrc (Amann et al. (1988) *Gene* 69:301-315) and pET 11d (Studier et al. (1990) *Gene Expression Technology: Methods in Enzymology* 185:60-89).

Recombinant protein expression can be maximized in a host bacteria by providing a genetic background wherein the host cell has an impaired capacity to proteolytically cleave the recombinant protein. (Gottesman, S. (1990) *Gene Expression Technology Methods in Enzymology* 185, Academic Press, San Diego, Calif. 119-128). Alternatively, the sequence of the polynucleotide of interest can be altered to provide preferential codon usage for a specific host cell, for example *E. coli.* (Wada et al. (1992) *Nucleic Acids Res.* 20:2111-2118).

The CaR2 polynucleotides can also be expressed by expression vectors that are operative in yeast. Examples of vectors for expression in yeast e.g., *S. cerevisiae* include pYepSec1 (Baldari et al. (1987) *EMBO J:* 6:229-234), pMFa (Kurjan et al. (1982) *Cell* 30:933-943), pJRY88 (Schultz et al. (1987) *Gene* 54:113-123), and pYES2 (Invitrogen Corporation, San Diego, Calif.).

The CaR2 polynucteotides can also be expressed in insect cells using, for example, baculovirus expression vectors. Baculovirus vectors available for expression of proteins in cultured insect cells (e.g., Sf9 cells) include the pAc series (Smith et al. (1983) *Mol. Cell. Biol.* 3:2156-2165) and the pVL series (Lucklow et al. (1989) *Virology* 170:31-39).

In certain embodiments of the invention, the polynucleotides described herein are expressed in mammalian cells using mammalian expression vectors. Examples of mammalian expression vectors include pCDM8 (Seed, B. (1987) *Nature* 329:840) and pMT2PC (Kaufman et al. (1987) *EMBO J:* 6:187-195).

The expression vectors listed herein are provided by way of example only of the well-known vectors available to those of ordinary skill in the art that would be useful to express the CaR2 polynucleotides. The person of ordinary skill in the art would be aware of other vectors suitable for maintenance propagation or expression of the polynucleotides described herein. These are found for example in Sambrook et al. (1989) *Molecular Cloning: A Laboratory Manual* 2nd; ed, Cold Spring Harbor Laboratory, Cold Spring Harbor Laboratory Press, Cold Spring Harbor, N.Y.

The invention also encompasses vectors in which the nucleic acid sequences described herein are cloned into the vector in reverse orientation, but operably linked to a regulatory sequence that permits transcription of antisense RNA. Thus, an antisense transcript can be produced to all, or to a portion, of the polynucleotide sequences described herein, including both coding and non-coding regions. Expression of this antisense RNA is subject to each of the parameters described above in relation to expression of the sense RNA (regulatory sequences, constitutive or inducible expression, tissue-specific expression).

The invention also relates to recombinant host cells containing the vectors described herein. Host cells therefore include prokaryotic cells, lower eukaryotic cells such as yeast, other eukaryotic cells such as insect cells, and higher eukaryotic cells such as mammalian cells.

The recombinant host cells are prepared by introducing the vector constructs described herein into the cells by techniques readily available to the person of ordinary skill in the art. These include, but are not limited to, calcium phosphate transfection, DEAE-dextran-mediated transfection, cationic lipid-mediated transfection, electroporation, transduction, infection, lipofection, and other techniques such as those found in Sambrook et al. (*Molecular Cloning: A Laboratory Manual,* 2d ed., Cold Spring Harbor Laboratory, Cold Spring Harbor Laboratory Press, Cold Spring Harbor, N.Y.). Host cells can contain more than one vector. Thus, different nucleotide sequences can be introduced on different vectors of the same cell. Similarly, the CaR2 polynucleotides can be introduced either alone or with other polynucleotides that are not related to the CaR2 polynucleotides such as those providing trans-acting factors for expression vectors. When more than one vector is introduced into a cell, the vectors can be introduced independently, co-introduced or joined to the CaR2 polynucleotide vector.

In the case of bacteriophage and viral vectors, these can be introduced into cells as packaged or encapsulated virus by standard procedures for infection and transduction. Viral vectors can be replication-competent or replication-defective. In the case in which viral replication is defective, replication will occur in host cells providing functions that complement the defects.

Vectors generally include selectable markers that enable the selection of the subpopulation of cells that contain the recombinant vector constructs. The marker can be contained in the same vector that contains the polynucleotides described herein or may be on a separate vector. Markers include tetracycline or ampicillin-resistance genes for prokaryotic host cells and dihydrofolate reductase or neomycin resistance for eukaryotic host cells. However, any marker that provides selection for a phenotypic trait will be effective.

While the mature proteins can be produced in bacteria, yeast, mammalian cells, and other cells under the control of the appropriate regulatory sequences, cell-free transcription and translation systems can also be used to produce these proteins using RNA derived from the DNA constructs described herein.

Where secretion of the polypeptide is desired, appropriate secretion signals are incorporated into the vector. The signal sequence can be endogenous to the CaR2 polypeptides or heterologous to these polypeptides.

Where the polypeptide is not secreted into the medium, the protein can be isolated from the host cell by standard disruption procedures, including freeze thaw, sonication, mechanical disruption, use of lysing agents and the like. The polypeptide can then be recovered and purified by well-known purification methods including ammonium sulfate precipitation, acid extraction, anion or cationic exchange chromatography, phosphocellulose chromatography, hydrophobic-interaction chromatography, affinity chromatography, hydroxylapatite chromatography, lectin chromatography, or high performance liquid chromatography.

It is also understood that depending upon the host cell in recombinant production of the polypeptides described herein, the polypeptides can have various glycosylation patterns, depending upon the cell, or maybe non-glycosylated as when produced in bacteria. In addition, the polypeptides may include an initial modified methionine in some cases as a result of a host-mediated process.

In another embodiment, the endogenous CaR2 is expressed. In one embodiment the cells of the present invention are cells that do not produce CaR2 naturally but which have been modified to over produce the CaR2 polypeptide. This can be done, for example, by the technology known as RAGE, described in WO 99/15650 and WO 00/49162. RAGE involves randomly incorporating a transcriptional activator in the genome by non-homologous recombination, leading to activation or increased expression of genes down stream of the activator. Unlike other cloning methods the artisan needs no knowledge about the gene sequences. Further, the gene is expressed in cells that normally produce it rather than a host cell, e.g., *E. coli.* Once a RAGE modified cell has been selected, e.g., by activity, or phenotype, that cell can be cultured and used as an expression vector for the CaR2 polypeptide. This can also be done by a technology that relies on homologous recombination to incorporate a transcriptional activator into the genome, as described in WO 94//12650, WO 95/31560, and WO 96/29411, U.S. Pat. No. 5,733,761 and U.S. Pat. No. 6,270,985.

In addition to the vectors and host cells described above, the invention is intended to include cells in which CaR2 is naturally expressed, e.g., normal cells such as kidney, prostate and osteoblasts, cancerous cells, or cells involved with osteoporosis.

The cells can disclosed herein be used in assays to determine the effectiveness of potential CaR2 modulators with regard to the ability of modulators to inhibit or activate CaR2.

II Diagnostic and Prognostic Assays of the Invention

The diagnostic and prognostic methods of the present invention can be used to identify various types of conditions, such as the conditions disclosed herein, mediated by CaR2. For example, CaR2 has been identified in bone (osteoblasts), kidney and prostate cells. It has also been observed that OC increases the sensitivity of CaR2 to calcium.

The CaR2 polypeptides also are useful to provide a target for diagnosing a conditions or predisposition to conditions mediated by the CaR2, including, but not limited to, conditions involving tissues in which the CaR2 are expressed as disclosed herein. Accordingly, methods are provided for detecting the presence, or levels of, CaR2 in a cell, tissue, or organism.

CaR2 has been found to be expressed in environments where there are high levels of calcium. Immunohistochemical analysis has shown expression of CaR2 in bone, kidney, prostate, salivary, glands, testis, thymus, brain, trachea and thyroid. The present invention shows that OC synergistically activates CaR2.

Accordingly, OC is a novel drug target for conditions associated with CaR2. Therefore, the methods disclosed herein are useful for treatment of conditions associated with the above-mentioned tissues, including, but not limited to, extracellular calcium concentration, metabolic conditions associated with CaR2 or OC, osteoporosis, sperm motility and viability, regulation of calcium flux in the kidneys, kidney stone formation, regulation of calcium flux in the prostate, promotion of osteoblast proliferation, e.g., for the production of osteoblasts for medical use, metastasis of cancers, cancers, e.g., breast, renal, prostate and bone cancers, regulation of bone mineralization, bone overgrowth modulation of bone healing, e.g., dental caries, osteoporosis, and other bone formation diseases, and detection of a subset of cells, e.g., for forensic analysis.

As used herein, the term "cancer" refers to conditions characterized by deregulated or uncontrolled cell growth, for example, carcinomas, sarcomas, lymphomas. The term "cancer" includes benign tumors, primary malignant tumors (e.g., those whose cells have not migrated to sites in the subject's body other than the site of the original tumor) and secondary malignant tumors (e.g., those arising from metastasis, the migration of tumor cells to secondary sites that are different from the site of the original tumor).

The term "metastasis" as used herein refers to the condition of spread of cancer from the organ of origin to additional distal sites in the patient. The process of tumor metastasis is a multistage event involving local invasion and destruction of intercellular and extracellular matrix, intravasation into blood vessels, lymphatics or other channels of transport, survival in the circulation, extravasation out of the vessels in the secondary site and growth in the new location (Fidler, et al., Adv. Cancer Res. 28, 149-250 (1978), Liotta, et al., Cancer Treatment Res. 40, 223-238 (1988), Nicolson, Biochim. Biophy. Acta 948, 175-224 (1988) and Zetter, N. Eng. J. Med. 322, 605-612 (1990)). Increased malignant cell motility has been associated with enhanced metastatic potential in animal as well as human tumors (Hosaka, et al., Gann 69, 273-276 (1978) and Haemmerlin, et al., Int. J. Cancer 27, 603-610 (1981)).

As used herein, the term "subject" includes living organisms, e.g., prokaryotes and eukaryotes. Examples of subjects include mammals, e.g., humans, dogs, cows, horses, kangaroos, pigs, sheep, goats, cats, mice, rabbits, rats, and transgenic non-human animals. Most preferably the subject is a human.

"Biological samples" include solid and body fluid samples. The biological samples of the present invention may include cells, protein or membrane extracts of cells, blood or biological fluids such as ascites fluid or brain fluid (e.g., cerebrospinal fluid). Examples of solid biological samples include samples taken from feces, the rectum, central nervous system, bone, breast tissue, renal tissue, the uterine cervix, the endometrium, the head/neck, the gallbladder, parotid tissue, the metastatic, the brain, the pituitary gland, kidney tissue, muscle, the esophagus, the stomach, the small intestine, the colon, the liver, the spleen, the pancreas, thyroid tissue, heart tissue, lung tissue, the bladder, adipose tissue, lymph node tissue, the uterus, ovarian tissue, adrenal tissue, testis tissue, the tonsils, and the thymus. Examples of "body fluid samples" include samples taken from the blood, serum, semen, metastatic fluid, seminal fluid, urine, saliva, sputum, mucus, bone marrow, lymph, and tears. For amplifying CaR2 RNA, the preferred samples include peripheral venous blood samples and metastatic tissue samples. Samples for use in the assays of the invention can be obtained by standard methods including venous puncture and surgical biopsy. In one embodiment, the biological sample is a metastatic tissue sample obtained by needle biopsy.

"Pharmacogenomics", as used herein, refers to the application of genomics technologies such as gene sequencing, statistical genetics, and gene expression analysis to drugs in clinical development and on the market. More specifically, the term refers the study of how a patient's genes determine a subject's response to a drug (e.g., a patient's "drug response phenotype", or "drug response genotype."

A. Antibody-Based Immunoassays

Methods for using antibodies as disclosed herein are particularly applicable to the cells, tissues and conditions that differentially express CaR2, or that are involved in CaR2 mediated conditions and as otherwise discussed herein.

The invention provides methods using antibodies that selectively bind to CaR2 and its variants and fragments. An antibody is considered to selectively bind, even if it also binds to other proteins that are not substantially homologous with CaR2. These other proteins share homology with a fragment or domain of the CaR2. This conservation in specific regions gives rise to antibodies that bind to both proteins by virtue of the homologous sequence. In this case, it would be understood that antibody binding to CaR2 is still selective.

Antibodies accordingly can be used diagnostically to monitor protein levels or activity in tissue as part of a clinical testing procedure, for example, to determine the efficacy of a given treatment regimen.

Additionally, antibodies are useful in pharmacogenomic analysis. Thus, antibodies prepared against polymorphic CaR2 can be used to identify individuals that require modified treatment modalities.

Antibodies can also be used in diagnostic procedures as an immunological marker for aberrant CaR2 analyzed by electrophoretic mobility, isoelectric point, tryptic peptide digest, and other physical assays known to those in the art.

The antibodies are also useful for tissue typing. Thus, where a specific CaR2 has been correlated with expression in a specific tissue, antibodies that are specific for this CaR2 can be used to identify a tissue type.

The antibodies are also useful in forensic identification. Accordingly, where an individual has been correlated with a specific genetic polymorphism resulting in a specific polymorphic protein, an antibody specific for the polymorphic protein can be used as an aid in identification.

Antibody detection of circulating fragments of the full length CaR2 can be used to identify CaR2 turnover.

Further, the antibodies can be used to assess CaR2 expression in disease states such as in active stages of the condition or in an individual with a predisposition toward a condition related to CaR2 function. When a disorder is caused by an inappropriate tissue distribution, developmental expression, or level of expression of CaR2 protein, the antibody can be prepared against the normal CaR2 protein. If a disorder is characterized by a specific mutation in CaR2, antibodies specific for this mutant protein can be used to assay for the presence of the specific mutant CaR2. However, intracellularly made antibodies ("intrabodies") are also encompassed, which would recognize intracellular CaR2 peptide regions.

The antibodies can also be used to assess normal and aberrant subcellular localization in cells in the various tissues in an organism. Antibodies can be developed against the whole CaR2 or portions of CaR2.

The amount of an antigen (i.e. CaR2) in a biological sample may be determined by a radioimmunoassay, an immunoradiometric assay, and/or an enzyme immunoassay.

"Radioimmunoassay" is a technique for detecting and measuring the concentration of an antigen using a labeled (i.e. radioactively labeled) form of the antigen. Examples of radioactive labels for antigens include $^3H$, $^{14}C$, and 125. The concentration of antigen (i.e. CaR2) in a sample (i.e. biological sample) is measured by having the antigen in the sample compete with a labeled (i.e. radioactively) antigen for binding to an antibody to the antigen. To ensure competitive binding between the labeled antigen and the unlabeled antigen, the labeled antigen is present in a concentration sufficient to saturate the binding sites of the antibody. The higher the concentration of antigen in the sample, the lower the concentration of labeled antigen that will bind to the antibody.

In a radioimmunoassay, to determine the concentration of labeled antigen bound to antibody, the antigen-antibody complex must be separated from the free antigen. One method for separating the antigen-antibody complex from the free antigen is by precipitating the antigen-antibody complex with an anti-isotype antiserum. Another method for separating the antigen-antibody complex from the free antigen is by precipitating the antigen-antibody complex with formalin-killed *S. aureus*. Yet another method for separating the antigen-antibody complex from the free antigen is by performing a "solid-phase radioimmunoassay" where the antibody is linked (i.e. covalently) to Sepharose beads, polystyrene wells, polyvinylchloride wells, or microtiter wells. By comparing the concentration of labeled antigen bound to antibody to a standard curve based on samples having a known concentration of antigen, the concentration of antigen in the biological sample can be determined.

A "Immunoradiometric assay" (IRMA) is an immunoassay in which the antibody reagent is radioactively labeled. An IRMA requires the production of a multivalent antigen conjugate, by techniques such as conjugation to a protein e.g., rabbit serum albumin (RSA). The multivalent antigen conjugate must have at least 2 antigen residues per molecule and the antigen residues must be of sufficient distance apart to allow binding by at least two antibodies to the antigen. For example, in an IRMA the multivalent antigen conjugate can be attached to a solid surface such as a plastic sphere. Unlabeled "sample" antigen and antibody to antigen which is radioactively labeled are added to a test tube containing the multivalent antigen conjugate coated sphere. The antigen in the sample competes with the multivalent antigen conjugate for antigen antibody binding sites. After an appropriate incubation period, the unbound reactants are removed by washing and the amount of radioactivity on the solid phase is determined. The amount of bound radioactive antibody is inversely proportional to the concentration of antigen in the sample.

The most common enzyme immunoassay is the "Enzyme-Linked Immunosorbent Assay (ELISA)." The "Enzyme-Linked Immunosorbent Assay (ELISA)" is a technique for detecting and measuring the concentration of an antigen using a labeled (i.e. enzyme linked) form of the antibody.

In a "sandwich ELISA", an antibody (i.e. to CaR2) is linked to a solid phase (i.e. a microtiter plate) and exposed to a biological sample containing antigen (i.e. CaR2). The solid phase is then washed to remove unbound antigen. A labeled (i.e. enzyme linked) is then bound to the bound-antigen (if present) forming an antibody-antigen-antibody sandwich. Examples of enzymes that can be linked to the antibody are alkaline phosphatase, horseradish peroxidase, luciferase, urease, and α-galactosidase. The enzyme linked antibody reacts with a substrate to generate a colored reaction product that can be assayed for.

In a "competitive ELISA", antibody is incubated with a sample containing antigen (i.e. CaR2). The antigen-antibody mixture is then contacted with an antigen-coated solid phase (i.e. a microtiter plate). The more antigen present in the sample, the less free antibody that will be available to bind to the solid phase. A labeled (i.e. enzyme linked) secondary antibody is then added to the solid phase to determine the amount of primary antibody bound to the solid phase.

In a "immunohistochemistry assay" a section of tissue for is tested for specific proteins by exposing the tissue to antibodies that are specific for the protein that is being assayed. The antibodies are then visualized by any of a number of methods to determine the presence and amount of the protein present. Examples of methods used to visualize antibodies are, for example, through enzymes linked to the antibodies (e.g., luciferase, alkaline phosphatase, horseradish peroxidase, or β-galactosidase), or chemical methods (e.g., DAB/Substrate chromagen).

Antibody based assays can be used to determine the levels of OC a given subject produces. As the calcium-sensing receptor of the present invention is activated by OC, aberrant levels of OC manifest the same CaR2 mediated conditions. OC levels can be measured using techniques that are standard in the art. For example, a kit for measuring OC is available from Biomedical Technologies Inc. (Stoughton, Mass.). OC assays are described in U.S. Pat. Nos. 5,866,364 and 5,681,707 and by Delmas P. D., 1990, Endocrinol. Clin. North Am. 19: 1-18; Koyama et al (1991) J. Immunol. Meth. 139, 17-23; and Grunhaberg et al. (1984) Meth. Enzymology, 207, 516.

B. CaR2 Nucleic Acid-Based Diagnostic and Prognostic Methods

Also encompassed by this invention is a method of diagnosing CaR2 related conditions in a subject, comprising: detecting a level of CaR2 nucleic acid in a biological sample; and comparing the level of CaR2 in the biological sample with a level of CaR2 in a control sample, wherein an elevation or reduction in the level of CaR2 in the biological sample compared to the control sample is indicative of CaR2 disorder.

In addition, this invention pertains to a method of diagnosing a CaR2 disorder in a subject, comprising the steps of: detecting a level of CaR2 nucleic acid in a biological sample; and comparing the level of CaR2 in the biological sample with a level of CaR2 in a control sample, wherein an elevation in the level of CaR2 in the biological sample compared to the control sample is indicative of an CaR2 condition. In preferred embodiments the CaR2 disorder is the metastasis of cancer, or other CaR2 mediated conditions such as the conditions disclosed herein.

In an embodiment of the above methods, the detecting a level of CaR2 nucleic acid in a biological sample includes amplifying CaR2 RNA. In another embodiment of the above methods, the detecting a level of CaR2 nucleic acid in a biological sample includes hybridizing the CaR2 RNA with a probe.

As an alternative to making determinations based on the absolute expression level of the CaR2 marker, determinations may be based on the normalized expression level of the marker. Expression levels are normalized by correcting the absolute expression level of a marker by comparing its expression to the expression of a gene that is not a marker, e.g., a housekeeping gene that is constitutively expressed. Suitable genes for normalization include housekeeping genes such as the actin gene, or epithelial cell-specific genes. This normalization allows the comparison of the expression level in one sample, e.g., a patient sample, to another sample, e.g., a non-metastatic cancer sample, or between samples from different sources.

Alternatively, the expression level can be provided as a relative expression level. To determine a relative expression level of a marker, the level of expression of the marker is determined for 10 or more samples of normal versus cancer cell isolates, preferably 50 or more samples, prior to the determination of the expression level for the sample in question. The mean expression level of each of the genes assayed in the larger number of samples is determined and this is used as a baseline expression level for the marker. The expression level of the marker determined for the biological sample (absolute level of expression) is then divided by the mean expression value obtained for that marker. This provides a relative expression level.

One preferred diagnostic method for the detection of mRNA levels involves contacting the isolated mRNA with a nucleic acid molecule (probe) that can hybridize to the mRNA encoded by the gene being detected. Probes based on the sequence of a nucleic acid molecule of the invention can be used to detect transcripts corresponding to CaR2. The nucleic acid probe can be, for example, a full-length cDNA, or a portion thereof, such as an oligonucleotide of at least 7, 15, 30, 50, 100, 250 or 500 nucleotides in length and sufficient to specifically hybridize under stringent conditions to a mRNA or genomic DNA encoding a marker of the present invention. Hybridization of an mRNA with the probe indicates that the marker in question is being expressed. In an embodiment, the probe includes a label group attached thereto, e.g., a radioisotope, a fluorescent compound, an enzyme, or an enzyme co-factor.

In one format, the mRNA is immobilized on a solid surface and contacted with a probe, for example by running the isolated mRNA on an agarose gel and transferring the mRNA from the gel to a membrane, such as nitrocellulose. In an alternative format, the probe(s) are immobilized on a solid surface and the mRNA is contacted with the probe(s), for example, in an Affymetrix gene chip array. A skilled artisan can readily adapt known mRNA detection methods for use in detecting the level of mRNA encoded by the markers of the present invention.

"Amplifying" refers to template-dependent processes and vector-mediated propagation which result in an increase in the concentration of a specific nucleic acid molecule relative to its initial concentration, or in an increase in the concentration of a detectable signal. As used herein, the term template-dependent process is intended to refer to a process that involves the template-dependent extension of a primer molecule. The term template dependent process refers to nucleic acid synthesis of an RNA or a DNA molecule wherein the sequence of the newly synthesized strand of nucleic acid is dictated by the well-known rules of complementary base pairing (see, for example, Watson, J. D. et al., In: Molecular Biology of the Gene, 4th Ed., W. A. Benjamin, Inc., Menlo Park, Calif. (1987). Typically, vector mediated methodologies involve the introduction of the nucleic acid fragment into a DNA or RNA vector, the clonal amplification of the vector, and the recovery of the amplified nucleic acid fragment. Examples of such methodologies are provided by Cohen et al. (U.S. Pat. No. 4,237,224), Maniatis, T. et al., Molecular Cloning (A Laboratory Manual), Cold Spring Harbor Laboratory, 1982.

A number of template dependent processes are available to amplify the target sequences of interest present in a sample. One of the best known amplification methods is the polymerase chain reaction (PCR) which is described in detail in Mullis, et al., U.S. Pat. No. 4,683,195, Mullis, et al., U.S. Pat. No. 4,683,202, and Mullis, et al., U.S. Pat. No. 4,800,159, and in Innis et al., PCR Protocols, Academic Press, Inc., San Diego Calif., 1990. Briefly, in PCR, two primer sequences are prepared which are complementary to regions on opposite complementary strands of the target sequence. An excess of deoxynucleoside triphosphates are added to a reaction mixture along with a DNA polymerase (e.g., Taq polymerase). If the target sequence is present in a sample, the primers will bind to the target and the polymerase will cause the primers to be extended along the target sequence by adding on nucleotides. By raising and lowering the temperature of the reaction mixture, the extended primers will dissociate from the target to form reaction products, excess primers will bind to the target and to the reaction products and the process is repeated. Preferably a reverse transcriptase PCR amplification procedure may be performed in order to quantify the amount of mRNA amplified. Polymerase chain reaction methodologies are well known in the art.

Another method for amplification is the ligase chain reaction (LCR), disclosed in European Patent No. 320,308B1. In LCR, two complementary probe pairs are prepared, and in the presence of the target sequence, each pair will bind to opposite complementary strands of the target such that they abut. In the presence of a ligase, the two probe pairs will link to form a single unit. By temperature cycling, as in PCR, bound ligated units dissociate from the target and then serve as "target sequences" for ligation of excess probe pairs. Whiteley, et al., U.S. Pat. No. 4,883,750 describes an alternative method of amplification similar to LCR for binding probe pairs to a target sequence.

Qbeta Replicase, described in PCT Application No. PCT/US87/00880 may also be used as still another amplification method in the present invention. In this method, a replicative sequence of RNA which has a region complementary to that of a target is added to a sample in the presence of an RNA polymerase. The polymerase will copy the replicative sequence which can then be detected.

Strand Displacement Amplification (SDA) is another method of carrying out isothermal amplification of nucleic acids which involves multiple rounds of strand displacement and synthesis, i.e. nick translation. A similar method, called Repair Chain Reaction (RCR) is another method of amplification which may be useful in the present invention and is involves annealing several probes throughout a region targeted for amplification, followed by a repair reaction in which only two of the four bases are present. The other two bases can be added as biotinylated derivatives for easy detection. A similar approach is used in SDA.

CaR2 specific sequences can also be detected using a cyclic probe reaction (CPR). In CPR, a probe having a 3' and 5' sequences of non-metastatic specific DNA and middle sequence of metastatic specific RNA is hybridized to DNA which is present in a sample. Upon hybridization, the reaction is treated with RNaseH, and the products of the probe identified as distinctive products generating a signal which are released after digestion. The original template is annealed to another cycling probe and the reaction is repeated. Thus, CPR involves amplifying a signal generated by hybridization of a probe to a metastatic cancer specific expressed nucleic acid.

Still other amplification methods described in GB Application No. 2 202 328, and in PCT Application No. PCT/US89/01025 may be used in accordance with the present invention. In the former application, "modified" primers are used in a PCR like, template and enzyme dependent synthesis. The primers may be modified by labeling with a capture moiety (e.g., biotin) and/or a detector moiety (e.g., enzyme). In the latter application, an excess of labeled probes are added to a sample. In the presence of the target sequence, the probe binds and is cleaved catalytically. After cleavage, the target sequence is released intact to be bound by excess probe. Cleavage of the labeled probe signals the presence of the target sequence.

Other nucleic acid amplification procedures include transcription-based amplification systems (TAS) (Kwoh D., et al., Proc. Natl. Acad. Sci. (U.S.A.) 1989, 86:1173, Gingeras T. R., et al., PCT Application WO 88/1D315), including nucleic acid sequence based amplification (NASBA) and 3SR. In NASBA, the nucleic acids can be prepared for amplification by standard phenol/chloroform extraction, heat denaturation of a clinical sample, treatment with lysis buffer and minispin columns for isolation of DNA and RNA or guanidinium chloride extraction of RNA. These amplification techniques involve annealing a primer which has metastatic specific sequences. Following polymerization, DNA/RNA hybrids are digested with RNase H while double stranded DNA molecules are heat denatured again. In either case the single stranded DNA is made fully double stranded by addition of second metastatic specific primer, followed by polymerization. The double stranded DNA molecules are then multiply transcribed by a polymerase such as T7 or SP6. In an isothermal cyclic reaction, the RNAs are reverse transcribed into double stranded DNA, and transcribed once against with a polymerase such as T7 or SP6. The resulting products, whether truncated or complete, indicate metastatic cancer specific sequences.

Davey, C., et al., European Patent No. 329,822B1 disclose a nucleic acid amplification process involving cyclically synthesizing single-stranded RNA ("ssRNA"), ssDNA, and double-stranded DNA (dsDNA), which may be used in accordance with the present invention. The ssRNA is a first template for a first primer oligonucleotide, which is elongated by reverse transcriptase (RNA-dependent DNA polymerase). The RNA is then removed from resulting DNA:RNA duplex by the action of ribonuclease H(RNase H, an RNase specific for RNA in a duplex with either DNA or RNA). The resultant ssDNA is a second template for a second primer, which also includes the sequences of an RNA polymerase promoter (exemplified by T7 RNA polymerase) 5' to its homology to its template. This primer is then extended by DNA polymerase (exemplified by the large "Klenow" fragment of E. coli DNA polymerase I), resulting as a double-stranded DNA ("dsDNA") molecule, having a sequence identical to that of the original RNA between the primers and having additionally, at one end, a promoter sequence. This promoter sequence can be used by the appropriate RNA polymerase to make many RNA copies of the DNA. These copies can then re-enter the cycle leading to very swift amplification. With proper choice of enzymes, this amplification can be done isothermally without addition of enzymes at each cycle. Because of the cyclical nature of this process, the starting sequence can be chosen to be in the form of either DNA or RNA.

Miller, H. I., et al., PCT Application WO 89/06700 discloses a nucleic acid sequence amplification scheme based on the hybridization of a promoter/primer sequence to a target single-stranded DNA ("ssDNA") followed by transcription of many RNA copies of the sequence. This scheme is not cyclic; i.e. new templates are not produced from the resultant RNA transcripts. Other amplification methods include "race" disclosed by Frohman, M. A., In: PCR Protocols: A Guide to Methods and Applications 1990, Academic Press, New York) and "one-sided PCR" (Ohara, O., et al., Proc. Natl. Acad. Sci. (U.S.A.) 1989, 86:5673-5677).

Alternative amplification methods include: self sustained sequence replication (Guatelli et al. (1990) Proc. Natl. Acad. Sci. USA 87:1874-1878), transcriptional amplification system (Kwoh et al. (1989) Proc. Natl. Acad. Sci. USA 86:1173-1177), Q-Beta Replicase (Lizardi, et al. (1989) Bio Technology 6:1197) or any other nucleic acid amplification method, followed by the detection of the amplified molecules using techniques well-known to those of skill in the art. These detection schemes are especially useful for the detection of nucleic acid molecules if such molecules are present in very low numbers.

Methods based on ligation of two (or more) oligonucleotides in the presence of nucleic acid having the sequence of the resulting "di-oligonucleolide", thereby amplifying the di-oligonucleotide (Wu, D. Y. et al., Genomics 1989, 4:560), may also be used in the amplification step of the present invention.

Following amplification, the presence or absence of the amplification product may be detected. The amplified product may be sequenced by any method known in the art, including and not limited to the Maxam and Gilbert method. The sequenced amplified product is then compared to a sequence known to be in a metastatic cancer specific sequence. Alternatively, the nucleic acids may be fragmented into varying sizes of discrete fragments. For example, DNA fragments may be separated according to molecular weight by methods such as and not limited to electrophoresis through an agarose gel matrix. The gels are then analyzed by Southern hybridization. Briefly, DNA in the gel is transferred to a hybridization substrate or matrix such as and not limited to a nitrocellulose sheet and a nylon membrane. A labeled probe is applied to the matrix under selected hybridization conditions so as to hybridize with complementary DNA localized on the matrix. The probe may be of a length capable of forming a stable duplex. The probe may have a size range of about 200 to about 10,000 nucleotides in length, preferably about 200 nucleotides in length. Various labels for visualization or detection are known to those of skill in the art, such as and not limited to fluorescent staining, ethidium bromide staining for example, avidin/biotin, radioactive labeling such as $^{32}$P labeling, and the like. Preferably, the product, such as the PCR product, may be run on an agarose gel and visualized using a stain such as ethidium bromide. The matrix may then be analyzed by autoradiography to locate particular fragments which hybridize to the probe.

The CaR2 polynucleotides are also useful for monitoring the effectiveness of modulating compounds on the expression or activity of the CaR2 gene in clinical trials or in a treatment regimen. Thus, the gene expression pattern can serve as a barometer for the continuing effectiveness of treatment with the compound, particularly with compounds to which a patient can develop resistance. The gene expression pattern can also serve as a marker indicative of a physiological response of the affected cells to the compound. Accordingly, such monitoring would allow either increased administration of the compound or the administration of alternative compounds to which the patient has not become resistant. Similarly, if the level of nucleic acid expression falls below a desirable level, administration of the compound could be commensurately decreased.

Monitoring can be, for example, as follows: (i) obtaining a pre-administration sample from a subject prior to administration of the agent; (ii) detecting the level of expression of a specified mRNA or genomic DNA of the invention in the pre-administration sample; (iii) obtaining one or more post-administration samples from the subject; (iv) detecting the level of expression or activity of the mRNA or genomic DNA in the post-administration samples; (v) comparing the level of expression or activity of the mRNA or genomic DNA in the pre-administration sample with the mRNA or genomic DNA in the post-administration sample or samples; and (vi) increasing or decreasing the administration of the agent to the subject accordingly.

The CaR2 polynucleotides can be used in diagnostic assays for qualitative changes in CaR2 nucleic acid, and particularly in qualitative changes that lead to pathology. The polynucleotides can be used to detect mutations in CaR2 genes and gene expression products such as mRNA. The polynucleotides can be used as hybridization probes to detect naturally-occurring genetic mutations in the CaR2 gene and thereby to determine whether a subject with the mutation is at risk for a disorder caused by the mutation. Mutations include deletion, addition, or substitution of one or more nucleotides in the gene, chromosomal rearrangement, such as inversion or transposition, modification of genomic DNA, such as aberrant methylation patterns or changes in gene copy number, such as amplification. Detection of a mutated form of the CaR2 gene associated with a dysfunction provides a diagnostic tool for an active condition or susceptibility to a condition when the condition results from overexpression, underexpression, or altered expression of CaR2.

Mutations in the CaR2 gene can be detected at the nucleic acid level by a variety of techniques. Genomic DNA can be analyzed directly or can be amplified by using PCR prior to analysis. RNA or cDNA can be used in the same way.

In certain embodiments, detection of the mutation involves the use of a probe/primer in a polymerase chain reaction (PCR) (see, e.g. U.S. Pat. Nos. 4,683,195 and 4,683,202), such as anchor PCR or RACE PCR, or, alternatively, in a ligation chain reaction (LCR) (see, e.g., Landegran et al. (1988) *Science* 241: 1077-1080; and Nakazawa et al. (1994) *PNAS* 91:360-364), the latter of which can be particularly useful for detecting point mutations in the gene (see Abravaya et al. (1995) *Nucleic Acids Res.* 23:675-682). This method can include the steps of collecting a sample of cells from a patient, isolating nucleic acid (e.g., genomic, mRNA or both) from the cells of the sample, contacting the nucleic acid sample with one or more primers which specifically hybridize to a gene under conditions such that hybridization and amplification of the gene (if present) occurs, and detecting the presence or absence of an amplification product, or detecting the size of the amplification product and comparing the length to a control sample. Deletions and insertions can be detected by a change in size of the amplified product compared to the normal genotype. Point mutations can be identified by hybridizing amplified DNA to normal RNA or antisense DNA sequences.

Alternatively, mutations in a CaR2 gene can be directly identified, for example, by alterations in restriction enzyme digestion patterns determined by gel electrophoresis.

Further, sequence-specific ribozymes (U.S. Pat. No. 5,498,531) can be used to score for the presence of specific mutations by development or loss of a ribozyme cleavage site.

Perfectly matched sequences can be distinguished from mismatched sequences by nuclease cleavage digestion assays or by differences in melting temperature.

Sequence changes at specific locations can also be assessed by nuclease protection assays such as RNase and SI protection or the chemical cleavage method.

Furthermore, sequence differences between a mutant CaR2 gene and a wild-type gene can be determined by direct DNA sequencing. A variety of automated sequencing procedures can be utilized when performing the diagnostic assays ((1995) *Biotechniques* 19:448), including sequencing by mass spectrometry (see, e.g., PCT International Publication No. WO 94/16101; Cohen et al (1996) *Adv. Chromatogr.* 36:127-162; and Griffin et al. (1993) *Appl. Biochem. Biotechnol.* 38:147-159).

Other methods for detecting mutations in the gene include methods in which protection from cleavage agents is used to detect mismatched bases in RNA/RNA or RNA/DNA duplexes (Myers et al. (1985) Science 230: 1242); Cotton et al. (1988) *PNAS* 85:4397; Saleeba et al. (1992) *Meth. Enzymol.* 217:286-295), electrophoretic mobility of mutant and wild type nucleic acid is compared (Orita et al. (1989) *PNAS* 86:2766; Cotton et al. (1993) *Mutat. Res.* 285:125-144; and Hayashi et al. (1992) *Genet Anal. Tech. Appl* 9:73-79), and movement of mutant or wild-type fragments in polyacrylamide gels containing a gradient of denaturant is assayed using denaturing gradient gel electrophoresis (Myers et al. (1985) *Nature* 313:495). The sensitivity of the assay may be enhanced by using RNA (rather than DNA), in which the secondary structure is more sensitive to a change in sequence. In one embodiment, the subject method utilizes heteroduplex analysis to separate double stranded heteroduplex molecules on the basis of changes in electrophoretic mobility (Keen et al. (1991) *Trends Genet.* 7: 5). Examples of other techniques for detecting point mutations include, selective oligonucleotide hybridization, selective amplification, and selective primer extension.

In other embodiments, genetic mutations can be identified by hybridizing a sample and control nucleic acids, e.g., DNA or RNA, to high density arrays containing hundreds or thousands of oligonucleotide probes (Cronin et (1996) *Human Mutation* 7:244-255; Kozal et al. (1996) *Nature Medicine* 2:753-759). For example, genetic mutations can be identified in two dimensional arrays containing light-generated DNA probes as described in Cronin et al. supra. Briefly, a first hybridization array of probes can be used to scan through long stretches of DNA in a sample and control to identify base changes between the sequences by making linear arrays of sequential overlapping probes. This step allows the identification of point mutations. This step is followed by a second hybridization array that allows the characterization of specific mutations by using smaller, specialized probe arrays complementary to all variants or mutations detected. Each mutation array is composed of parallel probe sets, one complementary to the wild-type gene and the other complementary to the mutant gene.

The CaR2 polynucleotides can also be used for testing an individual for a genotype that while not necessarily causing the condition, nevertheless affects the treatment modality. Thus, the polynucleotides can be used to study the relationship between an individual's genotype and the individual's response to a compound used for treatment (pharmacogenomic relationship). In the present case, for example, a mutation in the CaR2 gene that results in altered affinity for substrate could result in an excessive or decreased drug effect with standard concentrations substrate. Accordingly, the CaR2 polynucleotides described herein can be used to assess the mutation content of the gene in an individual in order to select an appropriate to compound or dosage regimen for treatment.

Thus polynucleotides displaying genetic variations that affect treatment provide a diagnostic target that can be used to tailor treatment in an individual. Accordingly, the production of recombinant cells or animals containing these polymorphisms allow effective clinical design of treatment compounds and dosage regimens.

The methods can involve obtaining a control biological sample from a control subject, contacting the control sample with a compound or agent capable of detecting mRNA, or genomic DNA, such that the presence of mRNA or genomic DNA is detected in the biological sample, and comparing the presence of mRNA or genomic DNA in the control sample with the presence of mRNA or genomic DNA in the test sample.

The CaR2 polynucleotides are also useful for chromosome identification when the sequence is identified with an individual chromosome and to a particular location on the chromosome. First, the DNA sequence is matched to the chromosome by in situ or other chromosome-specific hybridization. Sequences can also be correlated to specific chromosomes by preparing PCR primers that can be used for PCR screening of somatic cell hybrids containing individual chromosomes from the desired species. Only hybrids containing the chromosome containing the gene homologous to the primer will yield an amplified fragment. Sublocalization can be achieved using chromosomal fragments. Other strategies include pre-screening with labeled flow-sorted chromosomes and preselection by hybridization to chromosome-specific libraries. Further mapping strategies include fluorescence in situ hybridization, which allows hybridization with probes shorter than those traditionally used. Reagents for chromosome mapping can be used individually to mark a single chromosome or a single site on the chromosome, or panels of reagents can be used for marking multiple sites and/or multiple chromosomes. Reagents corresponding to noncoding regions of the genes actually are preferred for mapping purposes. Coding sequences are more likely to be conserved within gene families, thus increasing the chance of cross hybridizations during chromosomal mapping.

The CaR2 polynucleotides can also be used to identify individuals from small biological samples. This can be done for example using restriction fragment-length polymorphism (RFLP) to identify an individual. Thus, the polynucleotides described herein are useful as DNA markers for RIJLP (See U.S. Pat. No. 5,272,057).

Furthermore, the CaR2 sequence can be used to provide an alternative technique, which determines the actual DNA sequence of selected fragments in the genome of an individual. Thus, the CaR2 sequences described herein can be used to prepare two PCR primers from the 5' and 3' ends of the sequences. These primers can then be used to amplify DNA from an individual for subsequent sequencing.

Panels of corresponding DNA sequences from individuals prepared in this manner can provide unique individual identifications, as each individual will have a unique set of such DNA sequences. It is estimated that allelic variation in humans occurs with a frequency of about once per each 500 bases. Allelic variation occurs to some degree in the coding regions of these sequences, and to a greater degree in the noncoding regions. The CaR2 sequences can be used to obtain such identification sequences from individuals and from tissue. The sequences represent unique fragments of the human genome. Each of the sequences described herein can, to some degree, be used as a standard against which DNA from an individual can be compared for identification purposes.

If a panel of reagents from the sequences is used to generate a unique identification database for an individual, those same reagents can later be used to identify tissue from that individual. Using the unique identification database, positive identification of the individual, living or dead, can be made from extremely small tissue samples.

The CaR2 polynucleotides can also be used in forensic identification procedures. PCR technology can be used to amplify DNA sequences taken from very small biological samples, such as a single hair follicle, body fluids (e.g. blood, saliva, or semen). The amplified sequence can then be compared to a standard allowing identification of the origin of the sample.

The CaR2 polynucleotides can thus be used to provide polynucleotide reagents, e.g., PCR primers, targeted to specific loci in the human genome, which can enhance the reliability of DNA-based forensic identifications by, for example, providing another "identification marker" (i.e. another DNA sequence that is unique to a particular individual). As described above, actual base sequence information can be used for identification as an accurate alternative to patterns formed by restriction enzyme generated fragments. Sequences targeted to the noncoding region are particularly useful since greater polymorphism occurs in the noncoding regions, making it easier to differentiate individuals using this technique.

The CaR2 polynucleotides can further be used to provide polynucleotide reagents, e.g., labeled or labelable probes which can be used in, for example, an in situ hybridization technique, to identify a specific tissue. This is useful in cases in which a forensic pathologist is presented with a tissue of unknown origin. Panels of CaR2 probes can be used to identify tissue by species and/or by organ type.

In a similar fashion, these primers and probes can be used to screen tissue culture for contamination (i.e. screen for the presence of a mixture of different types of cells in a culture).

Alternatively, the CaR2 polynucleotides can be used directly to block transcription or translation of CaR2 gene sequences by means of antisense or ribozyme constructs. Thus, in a disorder characterized by abnormally high or undesirable CaR2 gene expression, nucleic acids can be directly used for treatment.

The CaR2 polynucleotides are thus useful as antisense constructs to control CaR2 gene expression in cells, tissues, and organisms. A DNA antisense polynucleotide is designed to be complementary to a region of the gene involved in transcription, preventing transcription and hence production of CaR2 protein. An antisense RNA or DNA polynucleotide would hybridize to the mRNA and thus block translation of mRNA into CaR2 protein.

Examples of antisense molecules useful to inhibit nucleic acid expression include antisense molecules complementary to a fragment of the 5' untranslated region of SEQ ID NO:2 or SEQ ID NO:4 which also includes the start codon and antisense molecules which are complementary to a fragment of the 3' untranslated region of SEQ ID NO:2 or SEQ ID NO:4.

Alternatively, a class of antisense molecules can be used to inactivate mRNA in order to decrease expression of CaR2 nucleic acid. Accordingly, these molecules can treat a disorder characterized by abnormal or undesired CaR2 nucleic acid expression. This technique involves cleavage by means of ribozymes containing nucleotide sequences complementary to one or more regions in the mRNA that attenuate the ability of the mRNA to be translated. Possible regions include coding regions and particularly coding regions corresponding to the catalytic and other functional activities of the CaR2 protein.

The CaR2 polynucleotides also provide vectors for gene therapy in patients containing cells that are aberrant in CaR2 gene expression. Thus, recombinant cells, which include the patient's cells that have been engineered ex vivo and returned to the patient, are introduced into an individual where the cells produce the desired CaR2 protein to treat the individual.

The invention also encompasses kits for detecting the presence of a CaR2 nucleic acid in a biological sample. For example, the kit can comprise reagents such as a labeled or labelable nucleic acid or agent capable of detecting CaR2 nucleic acid in a biological sample; means for determining the amount of CaR2 nucleic acid in the sample; and means for comparing the amount of CaR2 nucleic acid in the sample with a standard. The compound or agent can be packaged in a suitable container. The kit can further comprise instructions for using the kit to detect phosphodiesterase mRNA or DNA.

C. OC Nucleic Acid-Based Diagnostic and Prognostic Methods

The methods described above for CaR2 nucleic acid based diagnostic and prognostic methods can be used in similar fashion to determine the presence and amount of OC in a biological sample.

The determination of OC abundance can be used to diagnose conditions associated with aberrant OC expression.

III. Methods for Identifying Modulators

A. CaR2 Modulators

Determining the ability of the calcium receptor to bind to a target molecule can be accomplished using a technology such as real-time Bimolecular Interaction Analysis (BIA). Sjolander et al. (1991) *Anal. Chem.* 63:2338-2345 and Szabo et al. (1995) *Curr. Opin. Struct. Biol.* 5:699-705. As used herein, "BIA" is a technology for studying biospecific interactions in real time, without labeling any of the interactants (e.g., BIAcore™). Changes in the optical phenomenon surface plasmon resonance (SPR) can be used as an indication of real-time reactions between biological molecules.

The test compounds of the present invention can be obtained using any of the numerous approaches in combinatorial library methods known in the art, including: biological libraries; spatially addressable parallel solid phase or solution phase libraries; synthetic library methods requiring deconvolution; the one-bead one-compound library method; and synthetic library methods using affinity chromatography selection. The biological library approach is limited to polypeptide libraries, while the other four approaches are applicable to polypeptide, non-peptide oligomer or small molecule libraries of compounds (Lam, K. S. (1997) *Anticancer Drug Des.* 12:145).

Examples of methods for the synthesis of molecular libraries can be found in the art, for example in DeWitt et al. (1993) *Proc. Natl. Acad. Sci. USA* 90:6909; Erb et al. (1994) *Proc. Natl. Acad. Sci. USA* 91:11422; Zuckerman et al. (1994) *J. Med. Chem.* 37:2678; Cho et al. (1993) *Science* 261:1303; Carell et al. (1994) *Angew. Chem. Int. Ed. Engl.* 33:2059; Carell et al. (1994) *Angew. Chem. Int. Ed. Engl.* 33:2061; and in Gallop et al. (1994) *J. Med. Chem.* 37:1233. Libraries of compounds may be presented in solution (e.g., Houghten (1992) *Biotechniques* 13: 412-421), or on beads (Lam (1991) *Nature* 354:82-84), chips (Fodor (1993) *Nature* 364:555-556), bacteria (Ladner U.S. Pat. No. 5,223,409), spores (Ladner U.S. Pat. No. '409), plasmids (Cull et al. (1992) *Proc. Natl. Acad. Sci. USA* 89:1865-1869) or on phage (Scott and Smith (1990) *Science* 249:386-390); (Devlin (1990) *Science* 249:404-406); (Cwirla et al. (1990) *Proc. Natl. Acad. Sci. U.S.A.* 97:6378-6382); Felici (1991) *J. Mol. Biol.* 222:301-310); (Ladner supra).

Candidate compounds include, for example, 1) peptides such as soluble peptides, including Ig-tailed fusion peptides and members of random peptide libraries (see, e.g., Lam et al. (1991) *Nature* 354:82-84; Houghten et al. (1991) *Nature* 354: 84-86) and combinatorial chemistry-derived molecular libraries made of D- and/or L-configuration amino acids; 2) phosphopeptides (e.g., members of random and partially degenerate, directed phosphopeptide libraries, see, e.g., Songyang et al. (1993) *Cell* 72:767-778); 3) antibodies (e.g., polyclonal, monoclonal, humanized, anti-idiotypic, chimeric, and single chain antibodies as well as Fab, F(ab')$_2$, Fab expression library fragments, and epitope-binding fragments of antibodies); and 4) small organic and inorganic molecules (e.g., molecules obtained from combinatorial and natural product libraries).

One candidate compound is a soluble full-length calcium receptor or fragment that competes for ligand. Other candidate compounds include mutant calcium receptor or approaching fragments containing mutations that affect calcium receptor function and thus compete for ligand. Accordingly, a fragment that competes for ligand, for example with a higher affinity, or a fragment that binds ligand, is encompassed by the invention.

Other candidate compounds are OC, OC-like molecules or a fragment of OC that competes with CaR2 for binding. Other candidate compounds include mutant OC or mutant OC fragments that affect the ability of OC to bind to CaR2.

Protein inhibitors of the present invention can be selected using the RNA-protein fusion method that was developed by Szostak, J. W., et al. This method relies on a covalent fusion between an mRNA and a protein or peptide that it encodes through a puromycin at the 3' end of the RNA molecule. Fusion of the polypeptide to the RNA that encodes it allows for the skilled artisan to isolate a protein of interest while also isolating the nucleic acid that encodes the protein. The technology is described in Roberts, R. W. and Szostak, J. W. (1997) *Prot. Natl. Acad. Sci. USA* 11:12297-302 and Liu, R. et al. (2000) *Methods Enzymol.* 318:268-93, and in U.S. Pat. Nos. 6,207,446, 6,214,553, 6,261,804, 6,258,558, and 6,281,344.

The invention provides other end points to identify compounds that modulate (stimulate or inhibit) CaR2 activity. The assays typically involve an assays that indicate CaR2 activity. Thus, the expression of genes that are up- or down-regulated in response to the calcium receptor dependent signal cascade can be assayed. In one embodiment, the regulatory region of such genes can be operably linked to a marker that is easily detectable, such as luciferase. Alternatively, cleavage of the calcium receptor target could also be measured.

Any of the biological or biochemical functions mediated by the calcium receptor can be used as an endpoint assay. These include all of the biochemical or biochemical/biological events described herein, in the references cited herein, incorporated by reference for these endpoint assay targets, and other functions known to those of ordinary skill in the art.

Assays for calcium receptors are common in the field and have been previously described. For example, the activity of a calcium receptor can be conveniently measured using a Xenopus expression assay to detect increases in intracellular Ca++ due to receptor activation. Increases in intracellular Ca++ can be measured by different techniques such as by measuring current through the endogenous Ca++-activated Cl-channel; loading oocytes with $^{45}$Ca++ and measuring mobilization of $^{45}$Ca++ from intracellular stores; and using fluorescent Ca++ indicators.

The invention provides competition binding assays designed to discover compounds that interact with the calcium receptor. Thus, a compound is exposed to a calcium receptor polypeptide under conditions that allow the compound to bind or to otherwise interact with the polypeptide. Soluble CaR2 polypeptide is also added to the mixture. If the test compound interacts with the soluble CaR2 polypeptide, it decreases the amount of complex formed or activity from the CaR2 target. This type of assay is particularly useful in cases in which compounds are sought that interact with specific regions of the calcium receptor. Thus, the soluble polypeptide that competes with the target calcium receptor region is designed to contain peptide sequences corresponding to the region of interest.

Another type of competition-binding assay can be used to discover compounds that interact with specific functional sites. Accordingly, compounds can be discovered that directly interact with CaR2 and compete with substrate. Such assays can involve any other component that interacts with CaR2.

To perform cell-free drug screening assays, it is desirable to immobilize either the CaR2, or fragment, or its target molecule to facilitate separation of complexes from uncomplexed forms of one or both of the proteins, as well as to accommodate automation of the assay.

Techniques for immobilizing proteins on matrices can be used in the drug screening assays. In one embodiment, a fusion protein can be provided which adds a domain that allows the protein to be bound to a matrix. For example, glutathione-S-transferase/CaR2 fusion proteins can be absorbed onto glutathione sepharose beads (Sigma Chemical, St. Louis, Mo.) or glutathione derivatized microtitre plates, which are then combined with the cell lysates (e.g., $^{35}$S-labeled) and the candidate compound, and the mixture incubated under conditions conducive to complex formation (e.g., at physiological conditions for salt and pH). Following incubation, the beads are washed to remove any unbound label, and the matrix immobilized and radiolabel determined directly, or in the supernatant after the complexes is dissociated. Alternatively, the complexes can be dissociated from the matrix, separated by SDS-PAGE, and the level of CaR2-binding protein found in the bead fraction quantitated from the gel using standard electrophoretic techniques. For example, either the polypeptide or its target molecule can be immobilized utilizing conjugation of biotin and streptavidin using techniques well known in the art. Alternatively, antibodies reactive with the protein but which do not interfere with binding of the protein to its target molecule can be derivatized to the wells of the plate, and the protein trapped in the wells by antibody conjugation. Preparations of a CaR2-binding target component, and a candidate compound are incubated in the to CaR2-presenting wells and the amount of complex trapped in the well can be quantitated. Methods for detecting such complexes, in addition to those described above for the GST-immobilized complexes, include immunodetection of complexes using antibodies reactive with the CaR2 target molecule, or which are reactive with CaR2 and compete with the target molecule; as well as enzyme-linked assays which rely on detecting an enzymatic activity associated with the target molecule.

Nucleic acid expression assays are also useful for drug screening to identify compounds that modulate CaR2 nucleic acid expression (e.g., antisense, polypeptides, peptidomimetics, small molecules or other drugs). A cell is contacted with a candidate compound and the expression of mRNA determined. The level of expression of the mRNA in the presence of the candidate compound is compared to the level of expression of the mRNA in the absence of the candidate compound. The candidate compound can then be identified as a modulator of nucleic acid expression based on this comparison and be used, for example to treat a disorder characterized by aberrant nucleic acid expression. The modulator can bind to the nucleic acid or indirectly modulate expression, such as by interacting with other cellular components that affect nucleic acid expression.

Modulatory methods can be performed in vitro (e.g., by culturing the cell with the agent) or, alternatively, in vivo (e.g., by administering the gene to a subject) in patients or in transgenic animals.

The invention thus provides a method for identifying a compound that can be used to treat a disorder associated with expression of the CaR2 gene. The method typically includes assaying the ability of the compound to modulate the expression of the CaR2 nucleic acid and thus identifying a compound that can be used to treat a disorder characterized by excessive or deficient CaR2 nucleic acid expression.

The assays can be performed in cell-based and cell-free systems, such as systems using the tissues described herein, in which the gene is expressed or in model systems for the conditions to which the invention pertains. Cell-based assays include cells naturally expressing the CaR2 nucleic acid or recombinant cells genetically engineered to express specific nucleic acid sequences.

Alternatively, candidate compounds can be assayed in vivo in patients or in transgenic animals. The assay for CaR2 nucleic acid expression can involve direct assay of nucleic acid levels, such as mRNA levels.

Thus, modulators of CaR2 gene expression can be identified in a method wherein a cell is contacted with a candidate compound and the expression of mRNA determined. The level of expression of CaR2 mRNA in the presence of the candidate compound is compared to the level of expression of CaR2 mRNA in the absence of the candidate compound. The candidate compound can then be identified as a modulator of nucleic acid expression based on this comparison and be used, for example, to treat a disorder characterized by aberrant nucleic acid expression. When expression of mRNA is statistically significantly greater in the presence of the candidate compound than in its absence, the candidate compound is identified as a stimulator of nucleic acid expression. When nucleic acid expression is statistically significantly less in the presence of the candidate compound than in its absence, the candidate compound is identified as an inhibitor of nucleic acid expression.

B. Osteocalcin Modulators

The present invention is based on, in part, that OC activation of CaR2 when pre-incubated with Ca++ in a dose-dependent manner. This study, for the first time, identifies a regulatory role for OC. Accordingly, modulators that effect the ability of OC to activate CaR2, e.g., agonists or antagonists, are useful therapeutically.

The methods disclosed above to screen compounds for the ability to bind and/or modulate CaR2 are also useful for screening compounds for the ability to bind and/or modulate OC activation of CaR2. Compounds can be tested according to the methods disclosed herein for the ability to bind to OC, or the DNA that encodes OC and either increase or decrease the ability of OC to activate CaR2.

IV. CaR2 Cell Assays and Transgenic Animal Models

The methods using vectors and cells described herein are useful where the cells are those that naturally express the gene or a recombinant cell expressing the gene. The cells of the present invention are useful for identifying compounds that modulate CaR2 activity, as well as for testing the toxicity of compounds identified to modulate CaR2.

It is understood that "cells", "host cells" and "recombinant host cells" refer not only to the particular subject cell but also to the progeny or potential progeny of such a cell. Because certain modifications may occur in succeeding generations due to either mutation or environmental influences, such progeny may not, in fact, be identical to the parent cell, but are still included within the scope of the term as used herein.

The host cells expressing the polypeptides described herein, and particularly recombinant host cells, have a variety of uses. First, the cells are useful for producing CaR2 proteins or polypeptides that can be further purified to produce desired amounts of CaR2 protein or fragments. Thus, host cells containing expression vectors or cells expressing the endogenous CaR2 are useful for polypeptide production, as well as cells producing significant amounts of the polypeptide.

In one embodiment, host cells of the invention include cells that naturally produce CaR2, e.g., a kidney, prostate or bone cell. CaR2 has been shown to be produced in kidney, skeletal muscle, spleen, fetal liver, heart, stomach, uterus, salivary gland, adipose and prostate. CaR2 has been shown to be overproduced in gastrointestinal tumors and may be overexpressed in other cancer cells. Experiments have shown (see the Examples) that expression of CaR2 results in cells that are more invasive, e.g., more likely to be metastatic. Accordingly, assays can be performed using cancerous cells, e.g., biopsied cells, to determine the aggressiveness of the cancer. Invasiveness assays are common in the field and examples are presented below.

Host cells can be natural cells which naturally contain the CaR2 gene and have been modified using the Random Activation of Gene Expression (RAGE) technology to over express CaR2 (for details on the RAGE technology see WO 00/49162 and WO 99/15650, incorporated herein by reference). The RAGE technology provides methods of expressing an endogenous gene at levels higher than normally found in the cell without having to clone the gene. RAGE is based on the introduction of a transcriptional activator in to a genome by non-homologous recombination. Host cells can be modified by the introduction of a transcriptional activator by homologous recombination as described in WO 94//12650, WO 95/31560, WO 96/29411, U.S. Pat. No. 5,733,761 and U.S. Pat. No. 6,270,985.

Host cells are also useful for conducting cell-based assays involving the CaR2 or CaR2 fragments. Thus, a recombinant host cell expressing CaR2 is useful to assay for compounds that stimulate or inhibit CaR2 function.

Host cells are also useful for identifying CaR2 mutants in which these functions are affected. If the mutants naturally occur and give rise to a pathology, host cells containing the mutations are useful to assay compounds that have a desired effect on the mutant CaR2 (for example, stimulating or inhibiting function) which may not be indicated by their effect on the native CaR2.

Recombinant host cells are also useful for expressing the chimeric polypeptides described herein to assess compounds that activate or suppress activation by means of a heterologous domain, segment, site, and the like, as disclosed herein.

Further, mutant CaR2 can be designed in which one or more of the various functions is engineered to be increased or decreased and used to augment or replace CaR2 proteins in an individual. Thus, host cells can provide a therapeutic benefit by replacing an aberrant CaR2 or providing an aberrant CaR2 that provides a therapeutic result. In one embodiment, the cells provide CaR2 that are abnormally active.

In another embodiment, the cells provide CaR2 that is abnormally inactive. This CaR2 can compete with endogenous CaR2 in the individual.

In a related embodiment, the cell of the invention can produce abnormally low levels of CaR2. This can be done, for example, by a method called RNA interference (RNAi). The best developed RNAi method is one that employs the siRNA technology developed by Tuschl, et al. The siRNA technique is a method of post translational gene silencing that is initiated by double stranded RNA that is homologous to the sequence of the gene to be silenced. The siRNA methodology is described in Elbashir, S. M., et al. (2001) *Nature* 411:494-8 and Elbashir, S. M., et al. (2001) *EMBO J.* 3:6877-88. siRNAs have been used, for example, to silence genes in Xenopus embryos (Zhou, Y. et al. (2002) *Nucleic Acids Res.* 30:1664-9) and to silence human tissue factor expression (Holen, T, et al. (2002) *Nucleic Acids Res.* 30:1757-66).

In another embodiment, cells expressing CaR2 that cannot be activated are introduced into an individual in order to compete with endogenous CaR2.

Homologously recombinant host cells can also be produced that allow the in situ alteration of endogenous CaR2 polynucleotide sequences in a host cell genome. The host cell includes, but is not limited to, a stable cell line, cell in vivo, or cloned microorganism. This technology is more fully described in WO 93/09222, WO 91/12650, WO 91/06667, U.S. Pat. No. 5,272,071, and U.S. Pat. No. 5,641,670. Briefly, specific polynucleotide sequences corresponding to the CaR2 polynucleotides or sequences proximal or distal to a CaR2 gene are allowed to integrate into a host cell genome by homologous recombination where expression of the gene can be affected. In one embodiment, regulatory sequences are introduced that either increase or decrease expression of an endogenous sequence. Accordingly, a CaR2 protein can be produced in a cell not normally producing it. Alternatively, increased expression of CaR2 protein can be effected in a cell normally producing the protein at a specific level. Further, expression can be decreased or eliminated by introducing a specific regulatory sequence. The regulatory sequence can be heterologous to the CaR2 protein sequence or can be a homologous sequence with a desired mutation that affects expression. Alternatively, the entire gene can be deleted. The regulatory sequence can be specific to the host cell or capable of functioning in more than one cell type. Still further, specific mutations can be introduced into any desired region of the gene to produce mutant CaR2 proteins. Such mutations could be introduced, for example, into the specific functional regions such as the OC, calcium or G-protein binding site.

In one embodiment, the host cell can be a fertilized oocyte or embryonic stem cell that can be used to produce a transgenic animal containing the altered CaR2 gene. Alternatively, the host cell can be a stem cell or other early tissue precursor that gives rise to a specific subset of cells and can be used to produce transgenic tissues in an animal. See also Thomas et al., *Cell* 51:503 (1987) for a description of homologous recombination vectors. The vector is introduced into an embryonic stem cell line (e.g., by electroporation) and cells in which the introduced gene has homologously recombined with the endogenous CaR2e gene is selected (see e.g., Li, E. et al. (1992) *Cell* 69:915). The selected cells are then injected into a blastocyst of an animal (e.g., a mouse) to form aggregation chimeras (see e.g., Bradley, A. in *Teratocarcinornas and Embryonic Stem Cells: A Practical Approach*, E. J. Robertson, ed. (IRL, Oxford, 1987) pp. 113-152). A chimeric embryo can then be implanted into a suitable pseudopregnant female foster animal and the embryo brought to term. Progeny harboring the homologously recombined DNA in their germ cells can be used to breed animals in which all cells of the animal contain the homologously recombined DNA by germline transmission of the transgene. Methods for constructing homologous recombination vectors and homologous recombinant animals are described further in Bradley, A. (1991) *Current Opinion in Biotechnology* 2:823-829 and in PCT International Publication Nos. WO 90/11354; WO 91/01140; and WO 93/04169.

The genetically engineered host cells can be used to produce non-human transgenic animals. A transgenic animal is preferably a mammal, for example a rodent, such as a rat or mouse, in which one or more of the cells of the animal include a transgene. A transgene is exogenous DNA which is integrated into the genome of a cell from which a transgenic animal develops and which remains in the genome of the mature animal in one or more cell types or tissues of the transgenic animal. These animals are useful for studying the function of a CaR2 protein and identifying and evaluating modulators of CaR2 protein activity.

Other examples of transgenic animals include non-human primates, sheep, dogs, cows, goats, chickens, and amphibians.

In one embodiment, a host cell is a fertilized oocyte or an embryonic stem cell into which CaR2 polynucleotide sequences have been introduced.

A transgenic animal can be produced by introducing nucleic acid into the male pronuclei of a fertilized oocyte, e.g., by microinjection, retroviral infection, and allowing the oocyte to develop in a pseudopregnant female foster animal. Any of the CaR2 nucleotide sequences can be introduced as a transgene into the genome of a non-human animal, such as a mouse.

Animal based models for studying cancer in vivo are well known in the art (reviewed in Animal Models of Cancer Predisposition Syndromes, Hiai, H. and Hino, O. (eds.) 1999, *Progress in Experimental Tumor Research*, Vol. 35; Clarke, A. R. (2000) *Carcinogenesis* 21:435-41) and include, for example, carcinogen-induced tumors (Rithidech, K. et al. (1999) *Mutat. Res.* 428:33-39; Miller, M. L. et al. (2000) *Environ. Mol. Mutagen.* 35:319-327), injection and/or transplantation of tumor cells into an animal, as well as animals bearing mutations in growth regulatory genes, for example, oncogenes (e.g., ras) (Arbeit, J. M. et al. (1993) *Am. J. Pathol.* 142:1187-1197; Sinn, E. et al. (1987) *Cell* 49:465-475; Thorgeirsson, S S et al. (2000) *Toxicol. Lett.* 112-113:553-555) and tumor suppressor genes (e.g., p53) (Vooijs, M. et al. (1999) *Oncogene* 18:5293-5303; Clark A. R. (1995) *Cancer Metast. Rev.* 14:125-148; Kumar, T. R. et al. (1995) *J. Intern. Med.* 238:233-238; Donehower, L. A. et al. (1992) *Nature* 356215-221). Furthermore, experimental model systems are available for the study of, for example, ovarian cancer (Hamilton, T. C. et al. (1984) *Semin. Oncol.* 11:285-298; Rahman, N. A. et al. (1998) *Mol. Cell. Endocrinol.* 145:167-174; Beamer, W. G. et al. (1998) *Toxicol. Pathol.* 26:704-710), gastric cancer (Thompson, J. et al. (2000) *Int. J. Cancer* 86:863-869; Fodde, R. et al. (1999) *Cytogenet. Cell Genet.* 86:105-111), breast cancer (Li, M. et al. (2000) *Oncogene* 19:1010-1019; Green, J. E. et al. (2000) *Oncogene* 19:1020-1027), melanoma (Satyamoorthy, K. et al. (1999) *Cancer Metast. Rev.* 18:401-405); lung cancer (Malkinson, A. M. (2001) *Lung Cancer* 32(3):265-79; Zhao, B. et al. (2001) *Exp. Lung Res.* 26(8):567-79); colon cancer (Taketo, M. M. and Takaku (2000) *Hum. Cell* 13(3):85-95; Fodde, R. and Smits, R. (2001) *Trends. Mol. Med.* 7(8):369-73); and prostate cancer (Shirai, T. et al. (2000) *Mutat. Res.* 462:219-226; Bostwick, D. C. et al. (2000) *Prostate* 43:286-294).

Any of the regulatory or other sequences useful in expression vectors can form part of the transgenic sequence. This includes intronic sequences and polyadenylation signals, if not already included. A tissue-specific regulatory sequence(s) can be operably linked to the transgene to direct expression of the CaR2 protein to particular cells.

Methods for generating transgenic animals via embryo manipulation and microinjection, particularly animals such as mice, have become conventional in the art and are described, for example, in U.S. Pat. Nos. 4,736,866 and 4,870,009, both by Leder et al., U.S. Pat. No. 4,873,191 by Wagner et al. and in Hogan, B., *Manipulating the Mouse Embryo*, (Cold Spring Harbor Laboratory Press, Cold Spring Harbor, N.Y., 1986). Similar methods are used for production of other transgenic animals. A transgenic founder animal can be identified based upon the presence of the transgene in its genome and/or expression of transgenic mRNA in tissues or cells of the animals. A transgenic founder animal can then be used to breed additional animals carrying the transgene. Moreover, transgenic animals carrying a transgene can further be bred to other transgenic animals carrying other transgenes. A transgenic animal also includes animals in which the entire animal or tissues in the animal have been produced using the homologously recombinant host cells described herein.

In another embodiment, transgenic non-human animals can be produced which contain selected systems, which allow for regulated expression of the transgene. One example of such a system is the cre/loxP recombinase system of bacteriophage PI. For a description of the cre/loxP recombinase system, see, e.g., Lakso et al. (1992) *PNAS* 89:6232-6236. Another example of a recombinase system is the FLP recombinase system of *S. cerevisiae* (O'Gorman et al. (1991) *Science* 251:1351-1355. If a cre/loxP recombinase system is used to regulate expression of the transgene, animals containing transgenes encoding both the Cre recombinase and a selected protein is required. Such animals can be provided through the construction of "double" transgenic animals, e.g., by mating two transgenic animals, one containing a transgene encoding a selected protein and the other containing a transgene encoding a recombinase.

Clones of the non-human transgenic animals described herein can also be produced according to the methods described in Wilmut et al. (1997) *Nature* 385: 810-813 and PCT International Publication Nos. WO 97/07668 and WO 97/07669. In brief, a cell, e.g., a somatic cell, from the transgenic animal can be isolated and induced to exit the growth cycle and enter $G_o$ phase. The quiescent cell can then be fused, e.g., through the use of electrical pulses, to an enucleated oocyte from an animal of the same species from which the quiescent cell is isolated. The reconstructed oocyte is then cultured such that it develops to morula or blastocyst and then transferred to a pseudopregnant female foster animal. The offspring born of this female foster animal will be a clone of the animal from which the cell, e.g., the somatic cell, is isolated.

Transgenic animals containing recombinant cells that express the polypeptides described herein are useful to conduct the assays described herein in an in vivo context. Accordingly, it is useful to provide non-human transgenic animals to assay in vivo CaR2 function, including cAMP interaction, the effect of specific mutant CaR2 on CaR2 function and cAMP interaction, and the effect of chimeric CaR2. It is also possible to assess the effect of null mutations, that is mutations that substantially or completely eliminate one or more CaR2 functions.

In general, methods for producing transgenic animals include introducing a nucleic acid sequence according to the present invention, the nucleic acid sequence capable of expressing the protein in a transgenic animal, into a cell in culture or in vivo. When introduced in vivo, the nucleic acid is introduced into an intact organism such that one or more cell types and, accordingly, one or more tissue types, express the nucleic acid encoding the protein. Alternatively, the nucleic acid can be introduced into virtually all cells in an organism by transfecting a cell in culture, such as an embryonic stem cell, as described herein for the production of transgenic animals, and this cell can be used to produce an entire transgenic organism. As described, in a further embodiment, the host cell can be a fertilized oocyte. Such cells are then allowed to develop in a female foster animal to produce the transgenic organism.

V. Methods of Using CaR2 and OC Modulators

The identification of CaR2 as a high concentration calcium sensor that is expressed in the epithelial ducts in kidney and prostate, as well as in bone tissue, allows for predictions of the physiological consequences expected to result from CaR2 hypo- and hyper-activity. Normocalcemia in mammals and other tetrapods is believed to be maintained primarily through actions of CaR. Specific activating and inactivating mutations in CaR lead to hyper- and hypocalcemic disease states. In analogy with CaR, such mutations in CaR2 would be expected to strongly influence its specific microenvironments, such as kidney and bone. In kidney, CaR2 is expected to respond to the $Ca^{++}$ concentration in fluids passing through the kidney tubules, resulting in either reabsorbtion of $Ca^{++}$ or its secretion in urine. Dysregulation could lead to excessive calcium loss or the formation of kidney stones. Similarly, osteoblast CaR2 activation might be expected to affect bone formation and bone mass. Accordingly, using drugs to modulate CaR2 activity may have therapeutic benefit for conditions such as the conditions disclosed herein.

Modulators of CaR2 level or activity identified according to these assays can be used to test the effects of modulation of expression or activity of the receptor on the outcome of clinically relevant conditions. This can be accomplished in vitro, in vivo, such as in human clinical trials, and in test models derived from other organisms, such as non-human transgenic subjects. Modulation in such subjects includes, but is not limited to, modulation of the cells, tissues, and conditions particularly disclosed herein. Modulators of CaR2 activity identified according to these drug screening assays can be used to treat a subject with a disorder mediated by CaR2 or OC, by treating cells that express the calcium receptor, such as those disclosed herein. In one embodiment, the cells that are treated are derived from cancerous tissue or tumors.

Accordingly, conditions in which modulation is particularly relevant can include the tissues disclosed herein. These methods of treatment include the steps of administering the modulators of CaR2 activity or OC binding in a pharmaceutical composition as described herein, to a subject in need of such treatment.

The invention thus provides methods for treating a disorder characterized by aberrant expression or activity of a calcium receptor, e.g., CaR2 or OC. In one embodiment, the method involves administering an agent (e.g., an agent identified by a screening assay described herein), or combination of agents that modulates (e.g., upregulates or downregulates) expression or activity of the proteins. In another embodiment, the method involves administering the calcium receptor or OC as therapy to compensate for reduced or aberrant expression or activity of the proteins.

Methods for treatment include but are not limited to the use of soluble CaR2 or OC or fragments of CaR2 or OC that compete for ligand. CaR2, OC, or fragments thereof, can have a higher affinity for the target so as to provide effective competition.

Stimulation of activity is desirable in situations in which the protein is abnormally downregulated and/or in which increased activity is likely to have a beneficial effect. Likewise, inhibition of activity is desirable in situations in which the protein is abnormally upregulated and/or in which decreased activity is likely to have a beneficial effect. In one example of such a situation, a subject has a disorder characterized by metastasis of cancer to a bone, or the formation of kidney stones. In another example, the subject has osteoporosis.

In another aspect, the invention pertains to using CaR2 modulators to treat subjects that have aberrant expression of OC. Individuals who express aberrant levels, or mutated, OC can be treated using modulators of CaR2 disclosed herein.

Pharmaceutical Compositions

The invention encompasses use of the polypeptides, nucleic acids, and other agents in pharmaceutical compositions to administer to the cells in which expression of the calcium receptor (CaR2) or OC is relevant and in conditions as disclosed herein. Uses are both diagnostic and therapeutic. The CaR2 and OC nucleic acid molecules, protein, modulators of the protein, and antibodies (also referred to herein as "active compounds") can be incorporated into pharmaceutical compositions suitable for administration to a subject, e.g., a human. Such compositions typically comprise the nucleic acid molecule, protein, modulator, or antibody and a pharmaceutically acceptable carrier. It is understood however, that administration can also be to cells in vitro as well as to in vivo model systems such as non-human transgenic animals.

The term "administer" is used in its broadest sense and includes any method of introducing the compositions of the present invention into a subject. This includes producing polypeptides or polynucleotides in vivo as by transcription or translation, in vivo, of polynucleotides that have been exogenously introduced into a subject. Thus, polypeptides or nucleic acids produced in the subject from the exogenous compositions are encompassed in the term "administer."

As used herein the language "pharmaceutically acceptable carrier" is intended to include any and all solvents, dispersion media, coatings, antibacterial and antifungal agents, isotonic and absorption delaying agents, and the like, compatible with pharmaceutical administration. The use of such media and agents for pharmaceutically active substances is well known in the art. Except insofar as any conventional media or agent is incompatible with the active compound, such media can be used in the compositions of the invention. Supplementary active compounds can also be incorporated into the compositions. A pharmaceutical composition of the invention is formulated to be compatible with its intended route of administration. Examples of routes of administration include parenteral, e.g., intravenous, intradermal, subcutaneous, oral (e.g., inhalation), transdermal (topical), transmucosal, and rectal administration. Solutions or suspensions used for parenteral, intradermal, or subcutaneous application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. pH can be adjusted with acids or bases, such as hydrochloric acid or sodium hydroxide. The parenteral preparation can be enclosed in ampules, disposable syringes or multiple dose vials made of glass or plastic.

Pharmaceutical compositions suitable for injectable use include sterile aqueous solutions (where water soluble) or dispersions and sterile powders for the extemporaneous preparation of sterile injectable solutions or dispersion. For intravenous administration, suitable carriers include physiological saline, bacteriostatic water, Cremophor ELTM (BASF, Parsippany, N.J.) or phosphate buffered saline (PBS). In all cases, the composition must be sterile and should be fluid to the extent that easy syringability exists. It must be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyethylene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, polyalcohols such as mannitol, sorbitol, sodium chloride in the composition. Prolonged absorption of the injectable compositions can be brought about by including in the composition an agent which delays absorption, for example, aluminum monostearate and gelatin.

Sterile injectable solutions can be prepared by incorporating the active compound (e.g., a CaR2 protein or anti-CaR2 antibody) in the required amount in an appropriate solvent with one or a combination of ingredients enumerated above, as required, followed by filtered sterilization. Generally, dispersions are prepared by incorporating the active compound into a sterile vehicle which contains a basic dispersion medium and the required other ingredients from those enumerated above. In the case of sterile powders for the preparation of sterile injectable solutions, the preferred methods of preparation are vacuum drying and freeze-drying which yields a powder of the active ingredient plus any additional desired ingredient from a previously sterile-filtered solution thereof.

Oral compositions generally include an inert diluent or an edible carrier. They can be enclosed in gelatin capsules or compressed into tablets. For oral administration, the agent can be contained in enteric forms to survive the stomach or further coated or mixed to be released in a particular region of the GI tract by known methods. For the purpose of oral therapeutic administration, the active compound can be incorporated with excipients and used in the form of tablets, troches, or capsules. Oral compositions can also be prepared using a fluid carrier for use as a mouthwash, wherein the compound in the fluid carrier is applied orally and swished and expectorated or swallowed. Pharmaceutically compatible binding agents, and/or adjuvant materials can be included as part of the composition. The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring.

For administration by inhalation, the compounds are delivered in the form of an aerosol spray from pressured container or dispenser, which contains a suitable propellant, e.g. a gas such as carbon dioxide, or a nebulizer.

Systemic administration can also be by transmucosal or transdermal means. For transmucosal or transdermal administration, penetrants appropriate to the barrier to be permeated are used in the formulation. Such penetrants are generally known in the art, and include, for example, for transmucosal administration, detergents, bile salts, and fusidic acid derivatives. Transmucosal administration can be accomplished through the use of nasal sprays or suppositories. For transdermal administration, the active compounds are formulated into ointments, salves, gels, or creams as generally known in the art.

The compounds can also be prepared in the form of suppositories (e.g., with conventional suppository bases such as cocoa butter and other glycerides) or retention enemas for rectal delivery.

In one embodiment, the active compounds are prepared with carriers that will protect the compound against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art. The materials can also be obtained commercially from Alza Corporation and Nova Pharmaceuticals, Inc. Liposomal suspensions (including liposomes targeted to infected cells with monoclonal antibodies to viral antigens) can also be used as pharmaceutically acceptable carriers. These can be prepared according to methods known to those skilled in the art, for example, as described in U.S. Pat. No. 4,522,811.

It is especially advantageous to formulate oral or parenteral compositions in dosage unit form for ease of administration and uniformity of dosage. "Dosage unit form" as used herein refers to physically discrete units suited as unitary dosages for the subject to be treated; each unit containing a predetermined quantity of active compound calculated to produce the desired therapeutic effect in association with the required pharmaceutical carrier. The specification for the dosage unit forms of the invention are dictated by and directly dependent on the unique characteristics of the active compound and the particular therapeutic effect to be achieved, and the limitations inherent in the art of compounding such an active compound for the treatment of individuals.

The nucleic acid molecules of the invention can be inserted into vectors and used as gene therapy vectors. Gene therapy vectors can be delivered to a subject by, for example, intravenous injection, local administration (U.S. Pat. No. 5,328,470) or by stereotactic injection (see e.g., Chen et al. (1994) *PNAS* 91:3054-3057). The pharmaceutical preparation of the gene therapy vector can include the gene therapy vector in an acceptable diluent, or can comprise a slow release matrix in which the gene delivery vehicle is imbedded. Alternatively, where the complete gene delivery vector can be produced intact from recombinant cells, e.g. retroviral vectors, the pharmaceutical preparation can include one or more cells which produce the gene delivery system. The pharmaceutical compositions can be included in a container, pack, or dispenser together with instructions for administration.

As defined herein, a therapeutically effective amount of protein or polypeptide (i.e., an effective dosage) ranges from about 0.001 to 30 mg/kg body weight, preferably about 0.01 to 25 mg/kg body weight, more preferably about 0.1 to 20 mg/kg body weight, and even more preferably about 1 to 10 mg/kg, 2 to 9 mg/kg, 3 to 8 mg/kg, 4 to 7 mg/kg, or 5 to 6 mg/kg body weight.

The skilled artisan will appreciate that certain factors may influence the dosage required to effectively treat a subject, including but not limited to the severity of the condition, previous treatments, the general health and/or age of the subject, and other conditions present. Moreover, treatment of a subject with a therapeutically effective amount of a protein, polypeptide, or antibody can include a single treatment or, preferably, can include a series of treatments. In a preferred example, a subject is treated with antibody, protein, or polypeptide in the range of between about 0.1 to 20 mg/kg body weight, one time per week for between about 1 to 10 weeks, preferably between 2 to 8 weeks, more preferably between about 3 to 7 weeks, and even more preferably for about 4, 5, or 6 weeks. It will also be appreciated that the effective dosage of antibody, protein, or polypeptide used for treatment may increase or decrease over the course of a particular treatment. Changes in dosage may result and become apparent from the results of diagnostic assays as described herein.

The present invention encompasses agents which modulate expression or activity. An agent may, for example, be a small molecule. For example, such small molecules include, but are not limited to, peptides, peptidomimetics, amino acids, amino acid analogs, polynucleotides, polynucleotide analogs, nucleotides, nucleotide analogs, organic or inorganic compounds (i.e., including heteroorganic and organometallic compounds) having a molecular weight less than about 10,000 grams per mole, organic or inorganic compounds having a molecular weight less than about 5,000 grams per mole, organic or inorganic compounds having a molecular weight less than about 1,000 grams per mole, organic or inorganic compounds having a molecular weight less than about 500 grams per mole, and salts, esters, and other pharmaceutically acceptable forms of such compounds.

It is understood that appropriate doses of small molecule agents depends upon a number of factors within the ken of the ordinarily skilled physician, veterinarian, or researcher. The dose(s) of the small molecule will vary, for example, depending upon the identity, size, and condition of the subject or sample being treated, further depending upon the route by which the composition is to be administered, if applicable, and the effect which the practitioner desires the small molecule to have upon the nucleic acid or polypeptide of the invention. Exemplary doses include milligram or microgram amounts of the small molecule per kilogram of subject or sample weight (e.g., about 1 microgram per kilogram to about 500 milligrams per kilogram, about 100 micrograms per kilogram to about 5 milligrams per kilogram, or about 1 microgram per kilogram to about 50 micrograms per kilogram. It is furthermore understood that appropriate doses of a small molecule depend upon the potency of the small molecule with respect to the expression or activity to be modulated. Such appropriate doses may be determined using the assays described herein. When one or more of these small molecules is to be administered to an animal (e.g., a human) in order to modulate expression or activity of a polypeptide or nucleic acid of the invention, a physician, veterinarian, or researcher may, for example, prescribe a relatively low dose at first, subsequently increasing the dose until an appropriate response is obtained. In addition, it is understood that the specific dose level for any particular animal subject will depend upon a variety of factors including the activity of the specific compound employed, the age, body weight, general health, gender, and diet of the subject, the time of administration, the route of administration, the rate of excretion, any drug combination, and the degree of expression or activity to be modulated.

Accordingly, the invention provides methods of treatment, with the nucleic acid as a target, using a compound identified through drug screening as a gene modulator to modulate CaR2 nucleic acid expression. Modulation includes both upregulation (i.e. activation or agonization) or down-regulation (suppression or antagonization) or effects on nucleic acid activity (e.g. when nucleic acid is mutated or improperly modified). Conditions characterized by aberrant expression or activity of the nucleic acid can be treated.

The gene is particularly relevant for the treatment of conditions involving the cells and tissues that differentially express CaR2, cells that are involved in cell proliferative conditions, and metastasis of those cells, and cells and tissues that are involved in conditions such as the conditions disclosed herein.

Alternatively, a modulator for CaR2 nucleic acid expression can be a small molecule or drug identified using the screening assays described herein as long as the drug or small molecule inhibits the CaR2 nucleic acid expression.

Computer Readable Means

The nucleotide or amino acid sequences of the invention are also provided in a variety of mediums to facilitate use thereof. As used herein, "provided" refers to a manufacture, other than an isolated nucleic acid or amino acid molecule, which contains a nucleotide or amino acid sequence of the present invention. Such a manufacture provides the nucleotide or amino acid sequences, or a subset thereof (e.g., a subset of open reading frames (ORFs)) in a form which allows a skilled artisan to examine the manufacture using means not directly applicable to examining the nucleotide or amino acid sequences, or a subset thereof, as they exists in nature or in purified form.

In one application of this embodiment, a nucleotide or amino acid sequence of the present invention can be recorded on computer readable media. As used herein, "computer readable media" refers to any medium that can be read and accessed directly by a computer. Such media include, but are not limited to: magnetic storage media, such as floppy discs, hard disc storage medium, and magnetic tape; optical storage media such as CD-ROM; electrical storage media such as RAM and ROM; and hybrids of these categories such as magnetic/optical storage media. The skilled artisan will readily appreciate how any of the presently known computer readable mediums can be used to create a manufacture comprising computer readable medium having recorded thereon a nucleotide or amino acid sequence of the present invention.

As used herein, "recorded" refers to a process for storing information on computer readable medium. The skilled artisan can readily adopt any of the presently known methods for recording information on computer readable medium to generate manufactures comprising the nucleotide or amino acid sequence information of the present invention.

A variety of data storage structures are available to a skilled artisan for creating a computer readable medium having recorded thereon a nucleotide or amino acid sequence of the present invention. The choice of the data storage structure will generally be based on the means chosen to access the stored information. In addition, a variety of data processor programs and formats can be used to store the nucleotide sequence information of the present invention on computer readable medium. The sequence information can be represented in a word processing text file, formatted in commercially-available software such as WordPerfect and Microsoft Word, or represented in the form of an ASCII file, stored in a database application, such as DB2, Sybase, Oracle, or the like. The skilled artisan can readily adapt any number of dataprocessor structuring formats (e.g., text file or database) in order to obtain computer readable medium having recorded thereon the nucleotide sequence information of the present invention.

By providing the nucleotide or amino acid sequences of the invention in computer readable form, the skilled artisan can routinely access the sequence information for a variety of purposes. For example, one skilled in the art can use the nucleotide or amino acid sequences of the invention in computer readable form to compare a target sequence or target structural motif with the sequence information stored within the data storage means. Search means are used to identify fragments or regions of the sequences of the invention which match a particular target sequence or target motif.

As used herein, a "target sequence" can be any DNA or amino acid sequence of six or more nucleotides or two or more amino acids. A skilled artisan can readily recognize that the longer a target sequence is, the less likely a target sequence will be present as a random occurrence in the database. The most preferred sequence length of a target sequence is from about 10 to 100 amino acids or from about 30 to 300 nucleotide residues. However, it is well recognized that commercially important fragments, such as sequence fragments involved in gene expression and protein processing, may be of shorter length.

As used herein, "a target structural motif," or "target motif," refers to any rationally selected sequence or combination of sequences in which the sequencers) are chosen based on a three-dimensional configuration which is formed upon the folding of the target motif. There are a variety of target motifs known in the art. Protein target motifs include, but are not limited to, enzyme active sites and signal sequences. Nucleic acid target motifs include, but are not limited to, promoter sequences, hairpin structures and inducible expression elements (protein binding sequences).

Computer software is publicly available which allows a skilled artisan to access sequence information provided in a computer readable medium for analysis and comparison to other sequences. A variety of known algorithms are disclosed publicly and a variety of commercially available software for conducting search means are and can be used in the computer-based systems of the present invention. Examples of such software includes, but is not limited to, MacPattern (EMBL), BLASTN and BLASTX (NCBIA).

For example, software which implements the BLAST (Altschul et al. (1990) J. Mol. Biol. 215:403-410) and BLAZE (Brutlag et al. (1993) Comp. Chem. 17:203-207) search algorithms on a Sybase system can be used to identify open reading frames (ORFs) of the sequences of the invention which contain homology to ORFs or proteins from other libraries. Such ORFs are protein encoding fragments and are useful in producing commercially important proteins such as enzymes used in various reactions and in the production of commercially useful metabolites.

The invention is further illustrated by the following examples, which should not be construed as further limiting. The contents of all references, pending patent applications and published patents, cited throughout this application are hereby expressly incorporated by reference. Those skilled in the art will understand that this invention may be embodied in many different forms and should not be construed as limited to the embodiments set forth herein; rather, these embodiments are provided so that this disclosure will fully convey the invention to those skilled in the art. Many modifications and other embodiments of the invention will come to mind in one skilled in the art to which this invention pertains having the benefit of the teachings presented in the foregoing description. Although specific terms are employed, they are used as in the art unless otherwise indicated.

EXAMPLES

Example 1

Identification and Characterization of a Novel Family C Group II G-Protein Coupled Receptor RAGE (Random Activation of Gene Expression) libraries were created and screened for novel sequences as previously described. From the resulting gene sequence database, one RAGE sequence-tagged product (167B12) was predicted to encode a partial protein that showed similarity to the extracellular ligand-binding domain of the metabotropic neurotransmitter receptor family C subfamily of GPCRs-167B 12, renamed CaR2, was found to be distributed over two exons of a novel gene located on chromosome 6 and molecular acquisition of the full-length cDNA led to the identification of the six coding exons. This cDNA contains a deduced open reading frame encoding a 926 amino acid protein (SEQ ID NO:2).

Example 2

CaR2 Protein Structure

CaR2 has the typical protein structure of members of the family C subfamily of GPCRs; a large N-terminal extracellular domain (ECD) and a C-terminal seven transmembrane (7TM) domain (for a review see, Hermans E. & Challiss R A (2001) Biochem J 359 465-484). Pfam analysis identifies two structural domains; an ANF domain in the ECD that indicates the region of the protein that is similar to the bacterial periplasmic binding proteins and the 7TM domain. Sequence comparisons indicate that CaR2 is a Group I or Group II receptor (identity to human metabotropic glutamate receptor is 27%, human calcium-sensing receptor is 32%, and human $GABA_B$ receptor is less than 5%). The highest overall identity (43%) was observed to a goldfish (*Cassius auratus*) receptor, termed 5.24. Receptor 5.24 functionally responds to positively charged amino acids and is classified as a fish odorant receptor (Speca D J et al. (1999) Neuron 23, 487-498).

Recently, the CaR2/167B12 gene was entered into the public protein database at NCBI and annotated as the human homolog of the Goldfish receptor 5.24 gene (XP_069224). This designation was based on bioinformatic and not functional considerations. As discussed below, the data indicate that receptor 5.24 is not the Goldfish ortholog of CaR2. CaR2 is not activated by the amino acids that activate receptor 5.24 and secondarily, the expression pattern determined for receptor 5.24 (olfactory epithelium but not kidney, liver, brain, muscle, ovary, intestine and testis) is qualitatively different from the CaR2 expression pattern.

Example 3

CaR2 mRNA Expression Profiling

To determine the tissue distribution of CaR2, an RT-PCR based expression profiling experiment was performed with primer pairs targeted to the 5'-end of the CaR2 mRNA, using first strand cDNA corresponding to twenty major organ systems. The results of this experiment indicated that CaR2 mRNA was produced in kidney, prostate, adrenal gland, salivary gland, testis, thymus, thyroid gland and trachea. RNA samples were treated with DNAse I (RNAse free) before use in first strand cDNA synthesis. A negative control (no Reverse Transcriptase) was included for all RNA samples. Following first strand cDNA synthesis the reaction mix was diluted from 20 µl to 100 µl. 1 µl of this mix was used per expression profiling PCR. In the first PCR reaction primers PP 315-PP 321 were utilized using Advantage 2 in a 50 µl volume with 36 cycles of PCR. 10 µl of this sample was analyzed on an agarose gel which invariably produced no visible fragments. Subsequently, 1 µl of this sample was diluted into 100 µl of water and a second round of PCR was performed using PP 315-PP 320. This time 28 cycles of PCR were performed. 10 µl of this sample was analyzed on an agarose gel and tissues were scored as positive or negative based on the pattern observed. A control PCR was performed using β-actin primers which produced a robust positive signal in plus Reverse transcriptase sample in a single round of 30 cycles.

Immunohistochemical studies performed with antibodies developed to this receptor indicated that CaR2 is most highly expressed in kidney, prostate and osteoblasts.

Example 4

Immunohistochemical Profiling of CaR2

Antibodies were prepared to peptides corresponding to 20-amino acid regions within the amino-terminal extracellular domain of CaR2, and these were used to study the expression of the receptor. Anti-CaR2 antibodies were prepared using the extracellular N-terminus domain of CaR2. Potential antigenic sequences were compared with sequences from mouse to ensure 100% homology. Two sequences were identified as potential antigenic epitopes, and synthetic peptides were made for these sequences and conjugated to KLH. The peptide sequences were: (1) [100] SKFNCS-RETVEFKCDYSSYM and (2) [473] MAEYDLQNDVFIIP-DQETKN. The peptides were injected in rabbits with complete Freund's adjuvant, boosted twice in incomplete Freund's adjuvant and bled at 6 and 8 weeks. The rabbits were boosted again and bled at 10 and 12 weeks. Antisera were titered by enzyme-linked immunosorbent assay (ELISA).

The receptor was immunohistochemically localized in bone (osteoblasts), kidney tubules, prostate, cerebellum, and hippocampus.

Example 5

Identification of CaR2 Ligands

To facilitate pharmacological experimentation, CaR2 cDNA was cloned into the mammalian expression vector pcDNA 3.1 (+) Neo with or without a COOH-terminal FLAG epitope. The transgene was introduced into the HEK293 cell line and stable transfectants were identified. These clones were analyzed for CaR2 expression by qPCR and Western blotting to identify those clones that were suitable for ligand identification. The clone HEK-167B12-2.1 was chosen for further experimentation.

Based on the homology to the characterized goldfish odorant receptor 5.24, initial studies investigated the ability of 18 naturally occurring amino acids to trigger changes of intracellular $Ca^{++}$ levels in the transfected cells, as measured with a fluorescent imaging plate reader (FLIPR).

FLIPR Assay

Intracellular $Ca^{++}$ was measured using a fluorometric imaging plate reader (FLIPR) [Molecular Devices]. Cells were seeded at a density of $1\times10^5$/well (96-well plate) or $1\times10^4$/well (384-well plate) in collagen coated plates and incubated overnight at 36.9° C. with 5% $CO_2$. Medium was aspirated from the plates and replaced with equal volumes of a no wash calcium dye (Molecular Devices) and modified Hank's buffered saline solution [$Ca^{2+}$-free, $Mg^{2+}$-free] (140 mM NaCl, 5.4 mM KCl, 0.64 mM $KH_2PO_4$, 3 mM $NaHCO_3$, 5.5 mM $C_6H_{12}O_6$, 20 mM HEPES, 2.5 mM Caprylic acid (or 2.5 mM probenecid)). The plates were incubated for 1 hour at 36.9° C. with 5% $CO_2$. FLIPR was used to measure changes in intracellular calcium as relative fluorescence upon activation by ligand.

None of the potential ligands caused a measurable effect, suggesting either that these molecules were not binding to 167B12 or that activation of the receptor did not elicit changes in intracellular $Ca^{++}$. Additional ligands that might activate a family C group I/II receptor (NMDA, $Ca^{++}$ and GABA) were tested next but also failed to elicit a positive FLIPR response. Upon re-examination of the expression profiling results it was realized that at least one 167B12 microenvironment, the residence of osteoblasts in bone, had a demonstrated high $Ca^{++}_o$. Also, the apical side of cells lining tubules in Henle's loop in kidney and in epithelial cells lining prostate ducts are microenvironments where a higher than standard extracellular $Ca^{++}$ can be expected. These deductions led to the further testing of $Ca^{++}$ as the activating ligand and showed that high calcium levels (>20 mM) caused a marked increase in fluorescence signal, and hence intracellular $Ca^{++}$, in the clone expressing CaR2 (FIG. 2). This effect was not observed in the parental cell line, indicating that CaR2 acts as a low-affinity $Ca^{++}$ receptor with pharmacology that is profoundly distinct from CaR as evidenced by an $EC_{50}$ of 85 mM for CaR2 as compared to an $EC_{50}$ of 4.1 mM for CaR in transfected HEK 293 cells.

Figure 3:
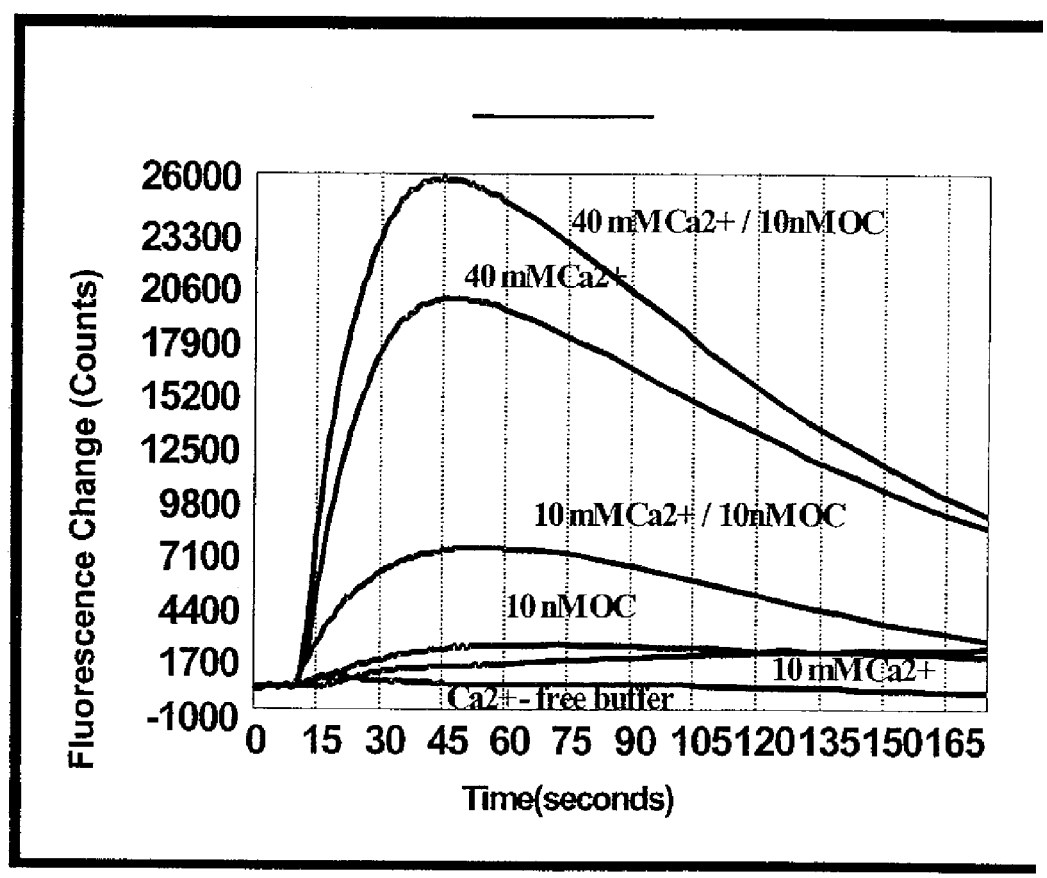
FIG. 3 shows OC(OC) dependent potentiation of the activation of CaR2 by $Ca^{++}$.

Having shown that high calcium levels activate CaR2, the effects of several agents known to modulate bone metabolism were determined. In the presence of OC (OC), CaR2 was activated at lower calcium levels and the activation by high mM calcium was potentiated (FIG. 3). This synergistic effect is only witnessed when calcium is pre-incubated with OC, but not when both ligands are added separately. Moreover, the effect was not observed when OC and $Ca^{++}$ were added to the parental HEK293 cells that do not express CaR2 or to HEK293 cells that express the previously characterized CaR.

When the $Ca^{++}$ concentration is held at a fixed value, there is a dose-dependent effect of OC, with the apparent $EC_{50}$ value for OC being between 1 nM and 10 nM (FIG. 4). The effect of combined OC and $Ca^{++}$ on receptor activation is blocked in the presence of $Pb^{++}$, which is known to prevent the formation of OC/Ca$^{++}$ complexes. These data suggest that CaR2 can bind free Ca$^{++}$ when the concentrations exceed ~20 mM. Moreover, the receptor can bind OC/Ca$^{++}$ complexes.

Figure 5A:
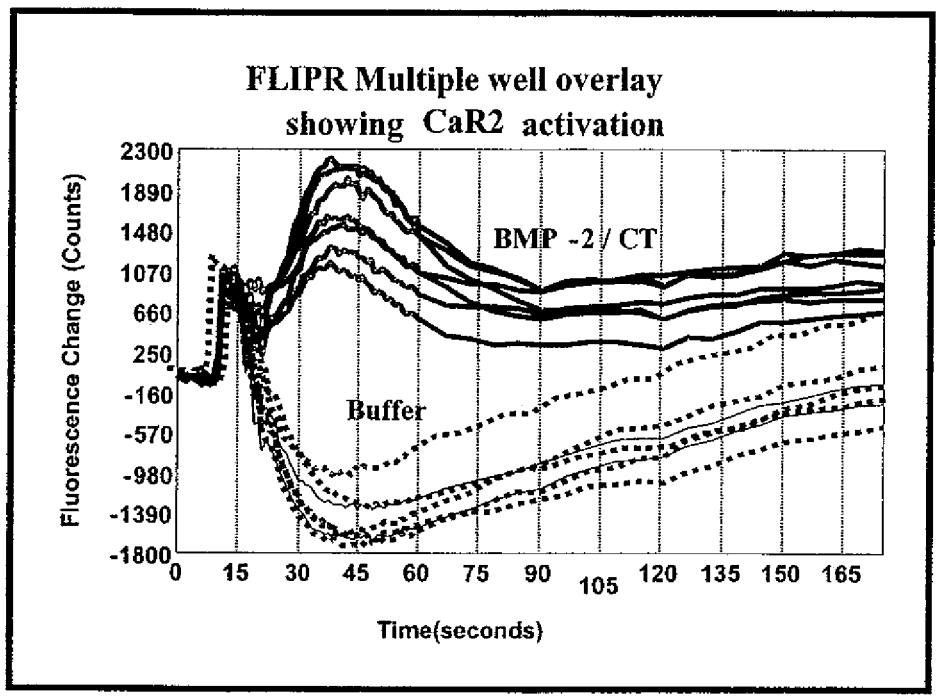
FIGS. 5A-B show activation of CaR2 by bone morphogenic peptide (BMP-2) and calcitonin (CT).
Figure 5B:
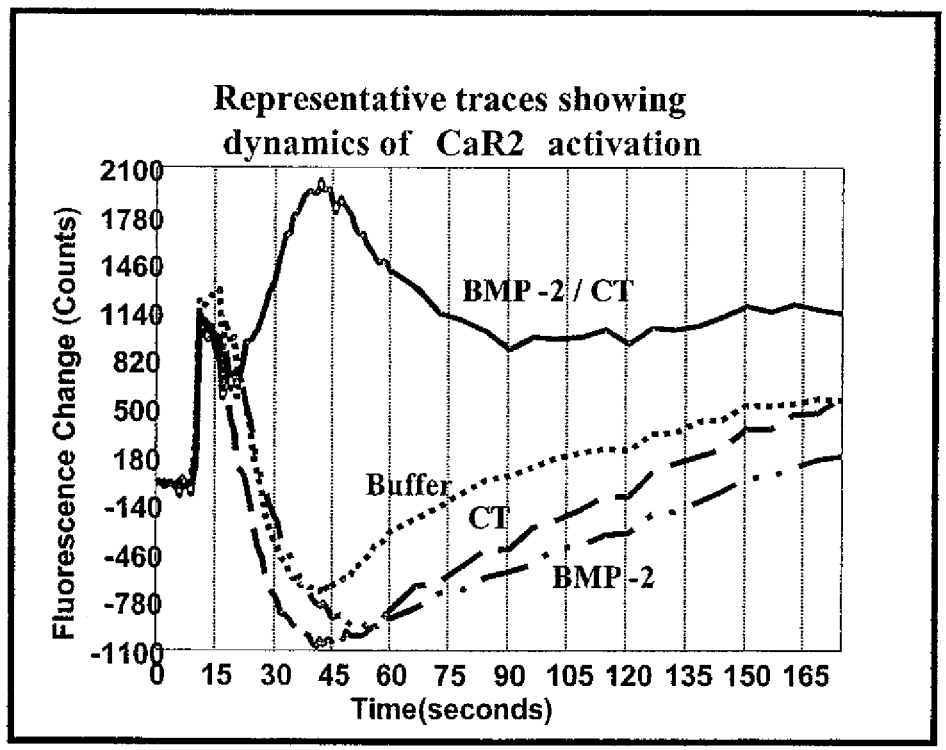

In the absence of calcium, the combination of bone morphogenic peptide (BMP-2) and calcitonin (CT) causes a modest increase in intracellular Ca$^{++}$ in the CaR2 clone, and not in the parental cells (FIG. 5). This effect is not seen when either ligand is added alone. The increased fluorescent signal is delayed relative to that seen when CaR2 is triggered by Ca$^{++}$ suggesting that CaR2 is being activated by an unknown mechanism in response to CT and BMP-2 binding to their cognate receptors.

Example 6

Osteoblast Survival in High mM Ca$^{2++}$

Saos-2 osteoblasts (ATCC-HTB-85) express CaR2 as determined by Western Blotting. Whereas these cells grew in buffer containing 2 mM Ca$^{++}$, they did not proliferate in medium containing 10 mM Ca$^{++}$ concentration and survived only a couple of days in culture before dying. In contrast, the Saos-2 cells survived and proliferated normally in medium containing 40 mM Ca$^{2+}$. These data suggest that activation of CaR2 by high calcium concentrations promotes osteoblast proliferation, and is consistent with the high calcium concentration found in the bone matrix.

Example 7

Physiology of CaR2

The characterization of a novel GPCR that is functionally activated by elevated concentrations of Ca$^{++}$ and physically located in the cellular microenvironments where high Ca$^{++}_0$ is expected (kidney epithelial cells lining tubules in the thick ascending limb of Henle's loop and in the skeletal osteoblasts) suggests that CaR2 is responsible for regulation of Ca$^{++}_0$ in these extreme Ca$^{++}$ environments.

This analysis suggests that OC may function as a signal to help regulate aspects of bone remodeling and mineralization that are mediated by CaR2. The fact that OC is an active participant in stimulating CaR2 is shown by the ability of OC to potentiate the activation of CaR2 in the presence of Ca$^{++}$. The existence of newly synthesized and catabolically generated soluble OC in remodeling bone matrix suggests that OC could be the proximal signal detected by CaR2 to integrate osteoblast function with the process of bone remodeling and mineralization. This premise is supported by data showing a significant linkage between osteoporosis and both the OC and vitamin D receptor genes (Deng H W, et al. (2002) J Bone Miner Res (4):678-86).

Example 8

CaR2 and Disease

CaR2 and OC expressing osteoblastic cells have a survival and proliferative advantage when challenged with the high concentration of free Ca++ that activates CaR2 and that is normally present in mineralizing bone.

In support of the relevance of CaR2 activity to conditions disclosed herein, some genetic predisposition to diseases of bone and kidney, as well as to cancer, have been mapped to human chromosome 6q22 in the vicinity of CaR2. Mapped diseases include two distinct bone dysplasias, craniometaphyseal dysplasia and oculodentodigital dysplasia, both of which map to this region of chromosome 6. In addition, a genetic cause for IgA nephropathy, a form of degenerative kidney disease, also maps to human chromosome 6q22-q23. A major factor in the progression of this disease is thought to be defects in the function of uteroglobin, a gene that is normally expressed in lung and that maps to chromosome 11. Uteroglobin hypomorphic mutations have been shown to promote the glomerular protein deposits that are a major part of IgA nephropathy. However, the genetic predisposition to this disease also maps to 6q, and an alteration of CaR2 function in the kidney may modify the progression of IgA nephropathy by altering kidney Ca$^{++}$ homeostasis and the ability of specialized kidney cells to survive or function.

Other human diseases have been mapped less precisely to the general region of chromosome 6q. Relevant diseases fall into three groups: diseases of bone, parathyroid and calcium homeostasis; factors affecting the development and progression of prostate, renal and bone cancer; and factors affecting the incidence of a variety of leukemias. Association of one or more of these diseases with CaR2 is plausible based upon overlap of disease pathology with CaR2 tissue distribution, and the demonstration of a calcium link to some of these diseases.

Genes for calcium receptors have been implicated in the development of hyperparathyroidism and parathyroid tumors, and factors increasing the propensity to develop primary hyperparathyroidism and parathyroid tumors have been mapped to 6q. Another genetic syndrome with a potential calcium link that has also been mapped to 6q is the Shwachman-Diamond syndrome. This disease is characterized by exocrine pancreatic insufficiency and hematological and skeletal abnormalities. Factors that promote the development and progression of prostate, renal and bone and blood cancers have also been mapped to 6q, and the fact that CaR2 is normally expressed in many of these tissues and might promote cell proliferation in high calcium environments suggests that CaR2 might play at least a supportive role in the development of these cancers.

It is not expected that these mapped diseases will represent a complete list of all 6q and 6q22 genes that are important in determining bone, prostate and kidney biology, cancer metastatic tissue tropism, and calcium homeostasis. Genes relevant to these processes may have been missed because the current mapping of human diseases has not yet been completed.

As mentioned, CaR2 may modify the progression of renal, prostate and bone cancer. In addition, CaR2 may influence the tissue tropism of metastases of these and other cancers. Breast cancers also often undergo metastasis to bone. If CaR2 does indeed play a role in promoting the colonization of bone by primary cancer cells from the prostate and kidney, then CaR2 expression in breast cancer cells may also promote the ability of these cells to proliferate in bone. In light of the bone tropism of breast cancers, it is interesting to consider that lactating mammary gland epithelium is an additional high calcium environment that might require a high threshold calcium receptor to regulate milk Ca$^{++}$ concentration. Although the induction of CaR2 expression during lactation has not yet been tested in lactating mammary gland, calcium concentration in human and other mammalian milks ranges from 8-40 mM, a range that is within the physiological detection limits of CaR2. Since Ca$^{++}$ concentration in milk seems to be regulated during lactation, CaR2 is an ideal candidate to help maintain appropriate Ca$^{++}$ levels, and the hypothesized presence of CaR2 in lactating mammary cells could link the mechanism driving the skeletal metastases of breast with those of prostate and kidney.

What is claimed:

1. An isolated nucleic acid molecule which encodes a polypeptide comprising the amino acid sequence set forth in SEQ ID NO:2.

2. A vector comprising the nucleic acid molecule of claim 1.

3. The vector of claim 2, which is an expression vector.

4. A host cell transfected with the vector of claim 3.

5. An isolated nucleic acid molecule comprising the nucleotide sequence set forth in SEQ ID NO:1.

6. An isolated nucleic acid molecule which hybridizes to the nucleic acid molecule set forth in SEQ ID NO:1 in 6×SSC at 45° C., followed by one or more washes in 0.2×SSC, 0.1% SDS at 65° C. under stringent conditions.

7. An isolated nucleic acid molecule which encodes a polypeptide comprising the sequence set forth in SEQ ID NO:2, wherein the nucleic acid molecule further comprises a nucleotide sequence encoding a heterologous polypeptide.

8. An isolated nucleic acid comprising a nucleotide sequence which is at least 97% identical to the nucleotide sequence of SEQ ID NO:1.

9. The isolated nucleic acid of claim 8, comprising a nucleotide sequence which is at least 98% identical to the nucleotide sequence of SEQ ID NO:1.

10. The isolated nucleic acid of claim 8, comprising a nucleotide sequence which is at least 99% identical to the nucleotide sequence of SEQ ID NO:1.

11. A host cell comprising a recombinant nucleic acid molecule comprising the nucleotide sequence set forth in SEQ ID NO:1, operably linked to a heterologous promoter.

* * * * *